United States Patent
Yue et al.

(10) Patent No.: US 12,108,660 B2
(45) Date of Patent: Oct. 1, 2024

(54) ORGANIC COMPOUND, ELECTRONIC COMPONENT, AND ELECTRONIC APPARATUS

(71) Applicant: SHAANXI LIGHTE OPTOELECTRONICS MATERIAL CO., LTD., Shaanxi (CN)

(72) Inventors: Fumin Yue, Shaanxi (CN); Tiantian Ma, Shaanxi (CN); Lei Yang, Shaanxi (CN); Yuanbao Zhang, Shaanxi (CN)

(73) Assignee: SHAANXI LIGHTE OPTOELECTRONICS MATERIAL CO., LTD., Shaanxi (CN)

( * ) Notice: Subject to any disclaimer, the term of this patent is extended or adjusted under 35 U.S.C. 154(b) by 0 days.

(21) Appl. No.: 18/552,951

(22) PCT Filed: Sep. 9, 2022

(86) PCT No.: PCT/CN2022/118041
§ 371 (c)(1),
(2) Date: Sep. 28, 2023

(87) PCT Pub. No.: WO2023/142492
PCT Pub. Date: Aug. 3, 2023

(65) Prior Publication Data
US 2024/0206327 A1 Jun. 20, 2024

(30) Foreign Application Priority Data
Jan. 28, 2022 (CN) .......................... 202210107822.4

(51) Int. Cl.
*H10K 85/60* (2023.01)
*C07C 211/61* (2006.01)
(Continued)

(52) U.S. Cl.
CPC .......... *H10K 85/633* (2023.02); *C07C 211/61* (2013.01); *C07D 209/86* (2013.01);
(Continued)

(58) Field of Classification Search
CPC .. H10K 85/633; H10K 85/636; C07C 211/60; C07C 211/61
See application file for complete search history.

(56) References Cited

FOREIGN PATENT DOCUMENTS

| CN | 111777517 A | * | 10/2020 | ........... C07B 59/001 |
| CN | 111995533 A | * | 11/2020 | ........... C07C 211/54 |

(Continued)

OTHER PUBLICATIONS

International Search Report w/English translation for PCT/CN2022/118041, mailed Nov. 29, 2022, 6 pages.
(Continued)

*Primary Examiner* — Vu A Nguyen
(74) *Attorney, Agent, or Firm* — Nixon & Vanderhye P.C.

(57) ABSTRACT

The present application relates to the field of organic light-emitting materials, and in particular to an organic compound, an electronic component, and an electronic apparatus. The structure of the organic compound is as represented by formula 1. The nitrogen-containing compound is used in an electronic component and can improve the performance of the component.

(Continued)

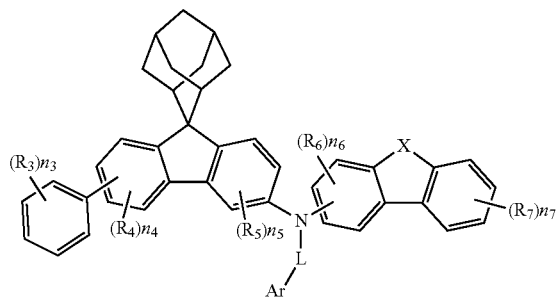

7 Claims, 1 Drawing Sheet

(51) Int. Cl.
| | | |
|---|---|---|
| C07D 209/86 | (2006.01) | |
| C07D 307/91 | (2006.01) | |
| C07D 333/76 | (2006.01) | |
| C09K 11/06 | (2006.01) | |
| H10K 50/15 | (2023.01) | |

(52) U.S. Cl.
CPC ......... *C07D 307/91* (2013.01); *C07D 333/76* (2013.01); *C09K 11/06* (2013.01); *H10K 85/636* (2023.02); *C07B 2200/05* (2013.01); *C07C 2603/18* (2017.05); *C07C 2603/26* (2017.05); *C07C 2603/97* (2017.05); *C09K 2211/1011* (2013.01); *C09K 2211/1014* (2013.01); *C09K 2211/1018* (2013.01); *H10K 50/156* (2023.02); *H10K 85/624* (2023.02); *H10K 85/626* (2023.02); *H10K 85/6572* (2023.02); *H10K 85/6574* (2023.02); *H10K 85/6576* (2023.02)

(56) References Cited

FOREIGN PATENT DOCUMENTS

| | | |
|---|---|---|
| CN | 112110825 A | 12/2020 |
| CN | 112209840 A | 1/2021 |
| CN | 113121408 A | 7/2021 |
| CN | 114591183 A | 6/2022 |
| WO | 2021136006 A1 | 7/2021 |

OTHER PUBLICATIONS

Written Opinion of the ISA for PCT/CN2022/118041, mailed Nov. 29, 2022, 4 pages.
Notification to Grant Patent Right for Invention w/English translation for CN202210107822.4 dated May 29, 2023, 7 pages.

* cited by examiner

ORGANIC COMPOUND, ELECTRONIC COMPONENT, AND ELECTRONIC APPARATUS

CROSS-REFERENCE TO RELATED APPLICATIONS

This application is the U.S. national phase of International Application No. PCT/CN2022/118041 filed Sep. 9, 2022, which designated the U.S. and claims the priority of Chinese patent application CN202210107822.4 submitted to China National Intellectual Property Administration on Jan. 28, 2022, each disclosure of which is incorporated herein by reference in its entirety.

TECHNICAL FIELD

The present disclosure relates to the technical field of organic luminescent materials, and in particular to an organic compound, an electronic component, and an electronic apparatus.

BACKGROUND

Organic light-emitting diode (OLED), as a new generation of display technology, have advantages of self-illumination, wide viewing angle, low power consumption, high response time, and full color, and are therefore of high research and development values and wide application prospects. An organic light-emitting device typically consists of a cathode, an anode, and an organic functional layer disposed between the cathode and the anode. The device comprises an anode, a hole transport layer, an emissive layer, an electron transport layer, a cathode, etc. The luminescence principle of organic electroluminescent devices is as follows: By applying a voltage, holes and electrons are injected from the anode and the cathode respectively under the influence of a direct-current electric field. These charge carriers are transported through the hole transport layer and the electron transport layer respectively, and finally meet and combine in the emissive layer to form excitons. During the process that the excitons in excited states return to ground states, light is emitted.

A series of breakthroughs and successes have been made so far in the development of OLED display technology, but there are still many obstacles in the development. For example, the development of OLED organic materials is facing great difficulties and challenges. Although many organic materials have been developed and are well known to us, there is a great imbalance in the development of the various organic materials. In order to remove current constraints on organic materials of organic electroluminescent devices, it is of critical importance to develop highly efficient organic electroluminescent materials so as to improve the performance of organic electroluminescent devices.

SUMMARY

Directed against the above problems with the existing technologies, the present disclosure aims at providing an organic compound, an electronic component, and an electronic apparatus. The organic compound, when used in electronic components, can improve the performance of the components and the devices.

To achieve the above objective, a first aspect of the present disclosure provides an organic compound having a structure as shown in Formula 1:

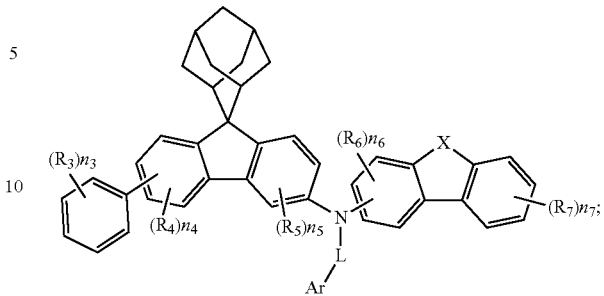

Formula 1 wherein X represents O, S, or $C(R_1R_2)$, $R_1$ and $R_2$ are identical or different, and are each independently selected from an alkyl with 1 to 4 carbon atoms or an aryl with 6 to 12 carbon atoms;

L is selected from a single bond, or a substituted or unsubstituted arylene with 6 to 25 carbon atoms;

Ar is selected from a substituted or unsubstituted aryl with 6 to 30 carbon atoms, or a substituted or unsubstituted heteroaryl with 5 to 30 carbon atoms;

substituents of L and Ar are each independently selected from deuterium, halogen, cyano, an alkyl with 1 to 10 carbon atoms, a haloalkyl with 1 to 10 carbon atoms, a deuterated alkyl with 1 to 10 carbon atoms, a cycloalkyl with 3 to 10 carbon atoms, a trialkylsilyl with 3 to 12 carbon atoms, an aryl with 6 to 18 carbon atoms, or a heteroaryl with 5 to 15 carbon atoms;

$R_3$, $R_4$, $R_5$, $R_6$, and $R_7$ are identical or different, and are each independently selected from deuterium, halogen, cyano, an alkyl with 1 to 4 carbon atoms, a haloalkyl with 1 to 4 carbon atoms, a deuterated alkyl with 1 to 4 carbon atoms, or an aryl with 6 to 12 carbon atoms;

$n_3$ represents the number of $R_3$, and is selected from 0, 1, 2, 3, 4, or 5, and when $n_3$ is greater than 1, each $R_3$ is identical or different;

$n_4$ represents the number of $R_4$, and is selected from 0, 1, 2, or 3, and when $n_4$ is greater than 1, each $R_4$ is identical or different;

$n_5$ represents the number of $R_5$, and is selected from 0, 1, 2, or 3, and when $n_5$ is greater than 1, each $R_5$ is identical or different;

$n_6$ represents the number of $R_6$, and is selected from 0, 1, 2, or 3, and when $n_6$ is greater than 1, each $R_6$ is identical or different;

$n_7$ represents the number of $R_7$, and is selected from 0, 1, 2, 3, or 4, and when $n_7$ is greater than 1, each $R_7$ is identical or different.

A second aspect of the present disclosure provides an electronic component comprising an anode and a cathode that are disposed opposite to each other, and a functional layer disposed between the anode and the cathode, where the functional layer comprises the organic compound described in the first aspect of the present disclosure.

A third aspect of the present disclosure provides an electronic apparatus comprising the electronic component described in the second aspect of the present disclosure.

In the present disclosure, a benzene ring is introduced onto a benzene ring structure on one side of amantadine spirofluorene, which can increase the conjugated plane of spirofluorene, thereby enhancing the structural stability of the material and improving the glass-transition temperature thereof. On this planar structure, diarylamine substituted with a dibenzo 5-membered-ring is directly linked to the 3-position of a benzene ring on the other side of adamantane spirofluorene

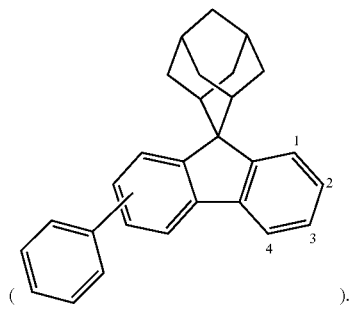

Thus, in the structure of the organic compound of the present disclosure formed, the three aryl groups conjugated with nitrogen atom include at least two planar structures, which can ensure fast mobility of molecules, and promote the transport of carriers between a hole transport layer and an organic emissive layer, thereby improving the luminescence efficiency of a device. Besides, the whole molecular structure has a suitable torque in space, which renders the structure of the material more stable, ensuring that the material can have good heat resistance during evaporation, and improving service life of devices comprising the organic compound.

REFERENCE NUMERALS

Figure 1:
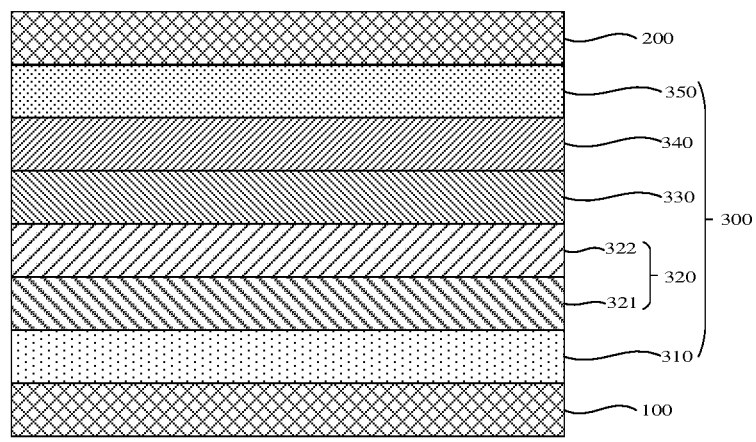
FIG. 1 is a schematic structural diagram of an organic electroluminescent device according to an embodiment of the present disclosure.

100: anode; 200: cathode; 300: functional layer; 310: hole injection layer; 320: hole transport layer; 321: first hole transport layer; 322: second hole transport layer; 330: organic emissive layer; 340: electron transport layer; 350: electron injection layer; 360: photoelectric conversion layer; 400: first electronic apparatus; 500: second electronic apparatus.

DETAILED DESCRIPTION

Specific embodiments of the present disclosure are described in detail below with reference to the accompanying drawings. It should be appreciated that the specific embodiments described herein are intended only to illustrate and explain, rather than limiting, the present disclosure.

Exemplary embodiments will now be described more comprehensively with reference to the accompanying drawings. The exemplary embodiments, however, can be implemented in a variety of forms and should not be interpreted as being limited to the examples set forth herein. On the contrary, these embodiments are provided to make the present disclosure more comprehensive and complete, and to communicate the concepts of these exemplary embodiments fully to those of ordinary skill in the art. Features, structures, or characteristics described herein can be combined in one or more embodiments in any suitable manner. In the following description, many specific details are provided to give a full understanding of the embodiments of the present disclosure.

In the present disclosure, the expression "each . . . independently" may be used interchangeably with the expressions " . . . each independently" and " . . . independently", and all these expressions should be interpreted in a broad sense. They can not only mean that, for same symbols in a same group, the selection of a specific option for one of the symbols and the selection of a specific option for another one of the symbols do not affect each other, but also mean that for same symbols in different groups, the selection of a specific option for one of the symbols and the selection of a specific option for another one of the symbols do not affect each other. For example,

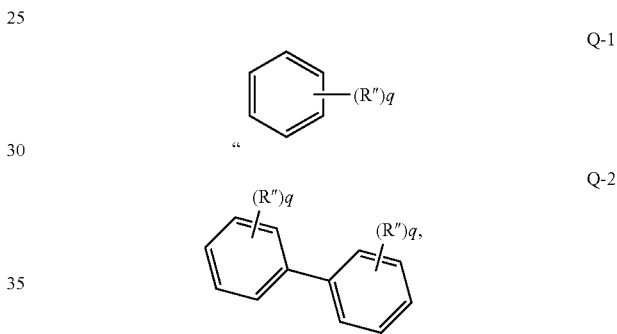

where each q is independently 0, 1, 2 or 3, and each R" is independently selected from hydrogen, deuterium, a fluorine or a chlorine", which means: in Formula Q-1, there are q substituents R" on the benzene ring, wherein each of the substituents R" may be identical or different, with the selection of an option for one of the substituents R" and the selection of an option for another one of the substituents R" not affecting each other; and in Formula Q-2, there are q substituents R" on each of the two benzene rings of biphenyl, wherein the number q of the substituent R" on one benzene ring and the number q of the substituent R" on the other benzene ring may be the same or different, and each substituent R" may be identical or different, with the selection of an option for one of the substituents R" and the selection of an option for another one of the substituents R" not affecting each other.

In the present disclosure, the term "substituted or unsubstituted" means that the functional group defined by the term may or may not have a substituent (hereinafter referred to as Rc for ease of description). For example, "substituted or unsubstituted aryl" refers to an aryl group with the substituent Rc or an unsubstituted aryl group. The above-mentioned substituents, namely Rc, may be, for example, deuterium, halogen, cyano, heteroaryl, aryl, alkyl, haloalkyl, deuterated alkyl, cycloalkyl, trialkylsilyl, etc. In the present disclosure, a "substituted" functional group may be substituted by one or more than two of the above substituent Rc.

In the present disclosure, the number of carbon atoms of a substituted or unsubstituted functional group refers to the number of all carbon atoms. As an example, if L is a substituted arylene having 12 carbon atom, then the number of all carbon atoms of the arylene group and substituents thereon is 12. As another example, if Ar is

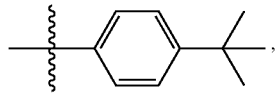

then the number of its carbon atoms is 10; and if L is

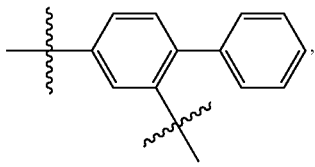 [SMILES: *c1ccc(-c2ccccc2)c(*)c1]

then the number of its carbon atoms is 12.

In the present disclosure, "aryl" refers to any functional group or substituent group derived from an aromatic carbon ring. An aryl group may be a monocyclic aryl group (e.g., phenyl) or a polycyclic aryl group. In other words, an aryl group may be a monocyclic aryl group, a fused cycloaryl group, two or more monocyclic aryl groups linked by carbon-carbon bond conjugation, a monocyclic aryl group and a fused cycloaryl group linked by carbon-carbon bond conjugation, or two or more fused cycloaryl groups linked by carbon-carbon bond conjugation. That is, unless otherwise specified, two or more aromatic groups linked by carbon-carbon bond conjugation may also be regarded as an aryl group in the present disclosure. Among them, fused cycloaryl groups may include, for example, bicyclic fused aryl groups (e.g., naphthyl), tricyclic fused aryl groups (e.g., phenanthryl, fluorenyl, anthryl), etc. An aryl group does not contain a heteroatom such as B, N, O, S, P, Se, and Si, etc. It should be noted that biphenyl and fluorenyl are considered as aryl groups in the present disclosure. Examples of aryl groups may include, but are not limited to, phenyl, naphthyl, fluorenyl, anthryl, phenanthryl, biphenyl, terphenyl, benzo[9,10]phenanthryl, pyrenyl, benzofluoranthryl, chrysenyl, etc.

In the present disclosure, "substituted aryl" may mean that one or more than two hydrogen atoms of the aryl group are substituted by a group such as deuterium, halogen, cyano, aryl, heteroaryl, trialkylsilyl, haloalkyl, alkyl, cycloalkyl, etc. It should be appreciated that the number of carbon atoms of a substituted aryl group refers to the number of all carbon atoms of the aryl group and the substituents on the aryl group. For example, a substituted aryl having 18 carbon atoms means that the number of all carbon atoms of the aryl group and substituents thereon is 18. Further, in the present disclosure, a fluorenyl group may be substituted, specific examples of substituted fluorenyl groups include, but are not limited to:

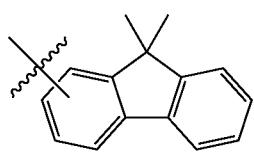

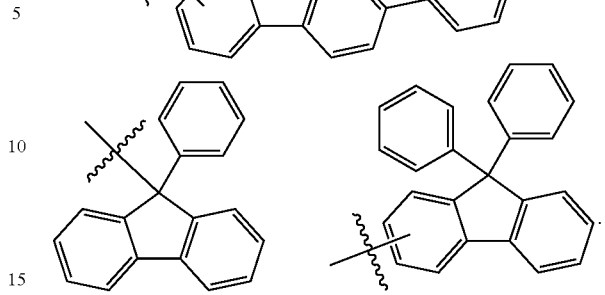

In the present disclosure, "arylene" refers to a divalent group formed by further removing one hydrogen atom from an aryl group.

In the present disclosure, the number of carbon atoms of a substituted or unsubstituted aryl group may be 6 to 30. Specifically, the number of carbon atoms of a substituted or unsubstituted aryl group may be 6, 7, 8, 9, 10, 11, 12, 13, 14, 15, 16, 17, 18, 19, 20, 21, 22, 23, 24, 25, 26, 27, 28, 29, or 30.

In the present disclosure, "heteroaryl" refers to a monovalent aromatic ring containing 1, 2, 3, 4, 5, or more heteroatoms or a derivative thereof. The heteroatoms may be one or more selected from B, O, N, P, Si, Se, and S. A heteroaryl group may be a monocyclic heteroaryl group or polycyclic heteroaryl group. In other words, a heteroaryl group may be a single aromatic ring system, or a plurality of aromatic ring systems linked by carbon-carbon bond conjugation, with any of the aromatic ring systems being an aromatic monocyclic ring or a fused aromatic ring. For example, heteroaryl groups may include, but are not limited to, thienyl, furyl, pyrrolyl, imidazolyl, thiazolyl, oxazolyl, oxadiazolyl, triazolyl, pyridyl, dipyridyl, pyrimidinyl, triazinyl, acridinyl, pyridazinyl, pyrazinyl, quinolyl, quinazolinyl, quinoxalinyl, phenoxazinyl, phthalazinyl, pyridopyrimidinyl, pyridopyrazinyl, pyrazinopyrazinyl, isoquinolyl, indolyl, carbazolyl, benzoxazolyl, benzimidazolyl, benzothiazolyl, benzocarbazolyl, benzothienyl, dibenzothienyl, thienothienyl, benzofuranyl, phenanthrolinyl, isoxazolyl, thiadiazolyl, phenothiazinyl, silafluorenyl, dibenzofuranyl, N-phenylcarbazolyl, N-pyridylcarbazolyl, N-methylcarbazolyl, etc. Among them, thienyl, furyl, phenanthrolinyl, and the like are each a heteroaryl group of a single aromatic ring system; and N-phenylcarbazolyl is a heteroaryl group of polycyclic systems linked by carbon-carbon bond conjugation. In the present disclosure, a heteroarylene group is a divalent group formed by further removing one or more hydrogen atoms from a heteroaryl group.

In the present disclosure, "substituted heteroaryl" may mean that one or more than two hydrogen atoms in the heteroaryl group are substituted by a group such as deuterium, halogen, cyano, aryl, heteroaryl, trialkylsilyl, alkyl, cycloalkyl, etc. It should be appreciated that the number of carbon atoms of a substituted heteroaryl group is the number of all carbon atoms of the heteroaryl group and substituents on the heteroaryl group.

In the present disclosure, the number of carbon atoms of a substituted or unsubstituted heteroaryl group may be 5-30. For example, the number of carbon atoms of a substituted or unsubstituted heteroaryl group may be 5, 6, 7, 8, 9, 10, 11, 12, 13, 14, 15, 16, 17, 18, 19, 20, 21, 22, 23, 24, 25, 26, 27, 28, 29, or 30.

In the present disclosure, a non-positioned connecting bond refers to a single bond "$-\xi-$" extending out from a ring system, which means that one end of the connecting bond can be connected to any position in the ring system through which the bond penetrates, and the other end of the connecting bond is connected to the rest part of a compound molecule structure. For example, as shown in Formula (f) below, the naphthyl group represented by Formula (f) is linked to other positions of the molecule through two non-positioned connecting bonds penetrating through the two rings, which indicates any of possible connecting mode shown in Formulae (f-1) to (f-10):

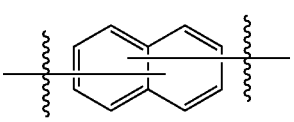
(f)

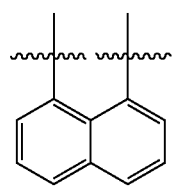
(f-1)

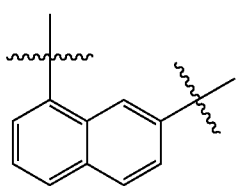
(f-2)

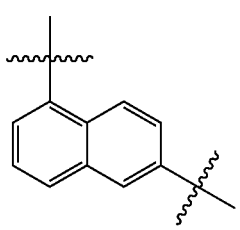
(f-3)

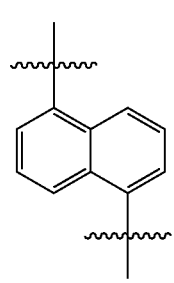
(f-4)

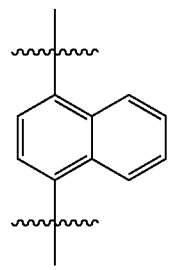
(f-5)

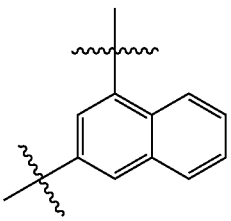
(f-6)

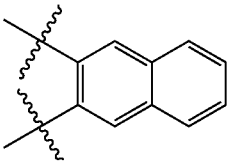
(f-7)

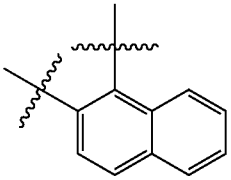
(f-8)

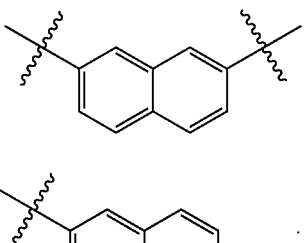
(f-9)

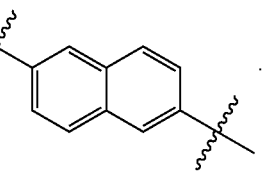
(f-10)

As another example, as shown in Formula (X') below, the dibenzofuranyl group represented by Formula (X') is linked to other positions of the molecule via a non-positioned connecting bond extending from the middle of a side benzene ring, which indicates any of possible connecting mode shown in Formulae (X'-1) to (X'-4):

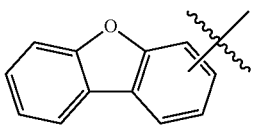
(X')

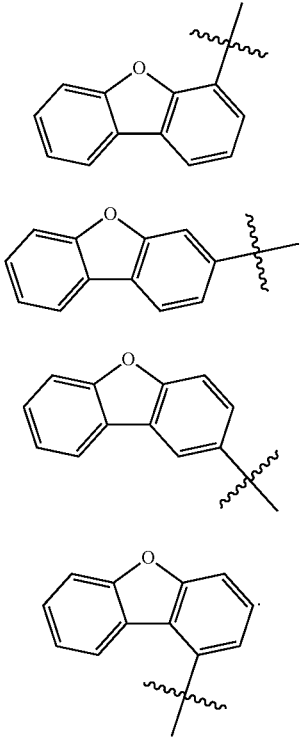

(X'-1)

(X'-2)

(X'-3)

(X'-4)

A non-positioned substituent in the present disclosure refers to a substituent linked via single bond extending from the center of a ring system, and it means that the substituent may be linked to any possible position in the ring system. For example, as shown in Formula (Y) below, the substituent R' represented by Formula (Y) is linked to a quinoline ring via a non-positioned connecting bond, which indicates any of possible connecting mode shown in Formulae (Y-1) to (Y-7):

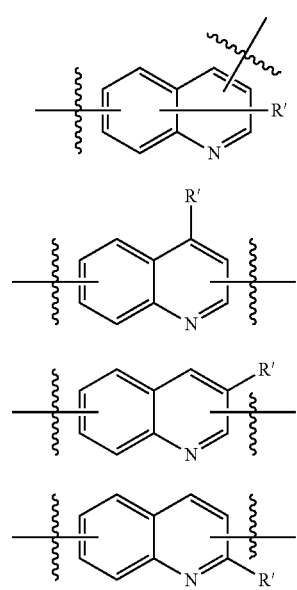

(Y)

(Y-1)

(Y-2)

(Y-3)

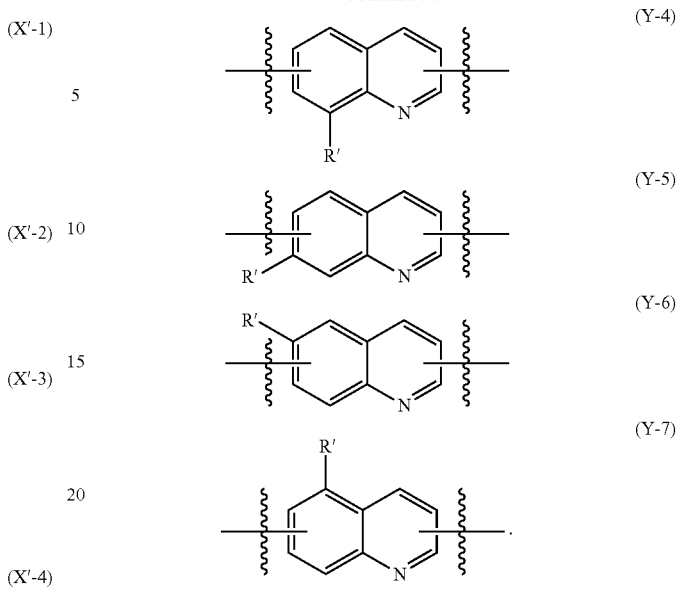

(Y-4)

(Y-5)

(Y-6)

(Y-7)

In the present disclosure, the number of carbon atoms of an alkyl group may be 1 to 10, and may specifically be 1, 2, 3, 4, 5, 6, 7, 8, 9, or 10. Alkyl groups may include straight-chain or branched-chain alkyl groups. Specific examples of alkyl groups include, but are not limited to, methyl, ethyl, n-propyl, isopropyl, n-butyl, isobutyl, tert-butyl, n-pentyl, isopentyl, n-hexyl, heptyl, n-octyl, 2-ethylhexyl, nonyl, decyl, 3,7-dimethyloctyl, etc.

In the present disclosure, halogen groups may include fluorine, iodine, bromine, or chlorine.

In the present disclosure, the number of carbon atoms of an aryl group as a substituent may be 6 to 18, and may specifically be, for example, 6, 10, 12, 13, 14, 15, 16, 18, etc. Specific examples of aryl groups as substituents include, but are not limited to, phenyl, naphthyl, biphenyl, phenanthryl, anthryl, fluorenyl, etc.

In the present disclosure, the number of carbon atoms of a heteroaryl group as a substituent may be 5 to 15, and may specifically be, for example, 5, 8, 9, 10, 12, 13, 14, 15, etc. Specific examples of heteroaryl groups as substituents include, but are not limited to, pyridyl, quinolyl, dibenzofuranyl, dibenzothienyl, carbazolyl, etc.

In the present disclosure, the number of carbon atoms of a trialkylsilyl group as a substituent may be 3-12, for example, 3, 6, 7, 8, 9, etc. Specific examples of trialkylsilyl groups include, but are not limited to, trimethylsilyl, ethyldimethylsilyl, triethylsilyl, etc.

In the present disclosure, the number of carbon atoms of a cycloalkyl group as a substituent may be 3-10, for example, 5, 6, 8, or 10. Specific examples of cycloalkyl groups include, but are not limited to, cyclopentyl, cyclohexyl, adamantly, etc.

In the present disclosure, the number of carbon atoms of a haloalkyl group as a substituent may be 1 to 10. For example, a haloalkyl group may be fluoroalkyl having 1 to 4 carbon atoms. Specific examples of haloalkyl groups include, but are not limited to, trifluoromethyl.

In the present disclosure, the number of carbon atoms of a deuterated alkyl group as a substituent may be 1 to 10. For example, a deuterated alkyl group may be deuterated alkyl having 1 to 4 carbon atoms. Specific examples of halogenated alkyl groups include, but are not limited to, trideuteromethyl.

The present disclosure, in a first aspect, provides an organic compound having a structure as shown in Formula 1:

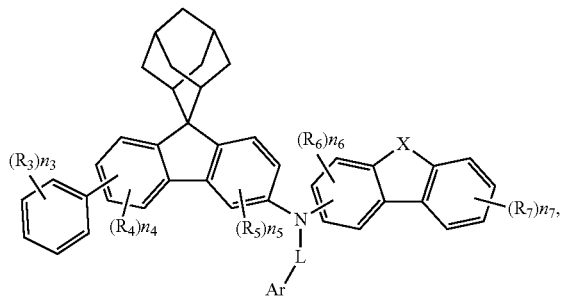

Formula 1 wherein X represents O, S, or $C(R_1R_2)$, $R_1$ and $R_2$ are identical or different, and are each independently selected from an alkyl with 1 to 4 carbon atoms or an aryl with 6 to 12 carbon atoms;

L is selected from a single bond, or a substituted or unsubstituted arylene with 6 to 25 carbon atoms;

Ar is selected from a substituted or unsubstituted aryl with 6 to 30 carbon atoms, or a substituted or unsubstituted heteroaryl with 5 to 30 carbon atoms;

substituents of L and Ar are each independently selected from deuterium, halogen, cyano, an alkyl with 1 to 10 carbon atoms, a haloalkyl with 1 to 10 carbon atoms, a deuterated alkyl with 1 to 10 carbon atoms, a cycloalkyl with 3 to 10 carbon atoms, a trialkylsilyl with 3 to 12 carbon atoms, an aryl with 6 to 18 carbon atoms, or a heteroaryl with 5 to 15 carbon atoms;

$R_3$, $R_4$, $R_5$, $R_6$, and $R_7$ are identical or different, and are each independently selected from deuterium, halogen, cyano, an alkyl with 1 to 4 carbon atoms, a haloalkyl with 1 to 4 carbon atoms, a deuterated alkyl with 1 to 4 carbon atoms, or an aryl with 6 to 12 carbon atoms;

$n_3$ represents the number of $R_3$, and is selected from 0, 1, 2, 3, 4, or 5, and when $n_3$ is greater than 1, each $R_3$ is identical or different;

$n_4$ represents the number of $R_4$, and is selected from 0, 1, 2, or 3, and when $n_4$ is greater than 1, each $R_4$ is identical or different;

$n_5$ represents the number of $R_5$, and is selected from 0, 1, 2, or 3, and when $n_5$ is greater than 1, each $R_5$ is identical or different;

$n_6$ represents the number of $R_6$, and is selected from 0, 1, 2, or 3, and when $n_6$ is greater than 1, each $R_6$ is identical or different;

$n_7$ represents the number of $R_7$, and is selected from 0, 1, 2, 3, or 4, and when $n_7$ is greater than 1, each $R_7$ is identical or different.

In the present disclosure, the structure of the organic compound is specifically selected from the group consisting of the following structures:

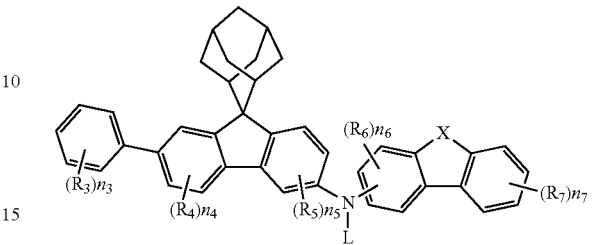

1-1

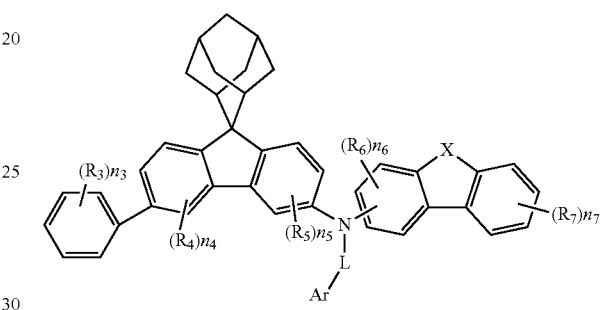

1-2

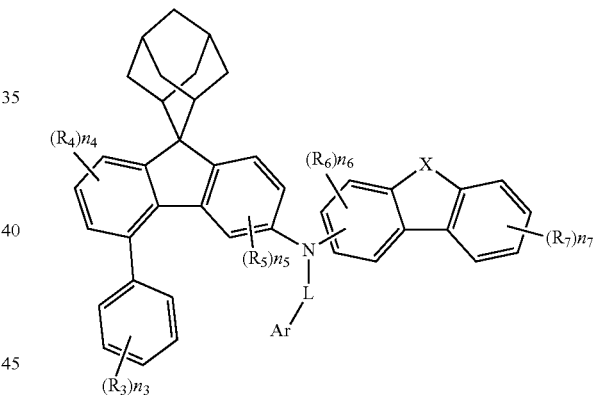

1-3

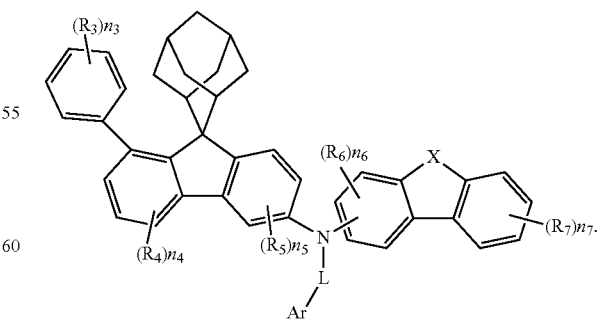

1-4

Preferably, the structure of the organic compound is selected from the group consisting of Formula 1-1, Formula 1-2, or Formula 1-3.

In the present disclosure,

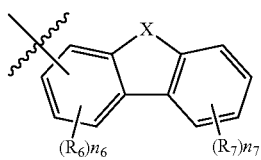

is selected from the group consisting of the following structures:

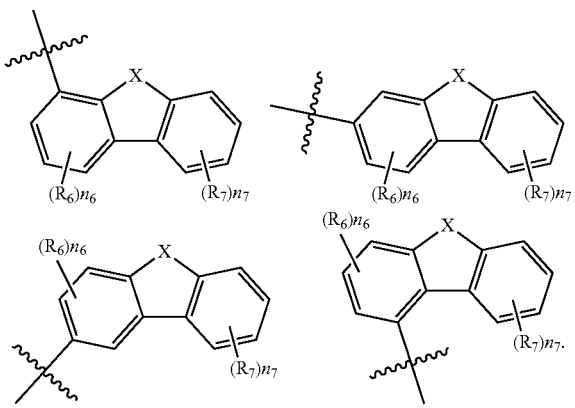

Optionally, L is selected from a single bond, or a substituted or unsubstituted arylene with 6 to 18 carbon atoms. For example, L is selected from a single bond, or a substituted or unsubstituted arylene having 6, 7, 8, 9, 10, 11, 12, 13, 14, 15, 16, 17, or 18 carbon atoms.

Optionally, L is selected from a single bond, a substituted or unsubstituted phenylene, a substituted or unsubstituted naphthylene, or a substituted or unsubstituted biphenylene.

Optionally, substituents in L are each independently selected from deuterium, fluorine, cyano, an alkyl with 1 to 4 carbon atoms, a fluoroalkyl with 1 to 4 carbon atoms, or aryl with 6 to 10 carbon atoms.

Optionally, the substituents in L are each independently selected from deuterium, fluorine, cyano, methyl, ethyl, isopropyl, tert-butyl, trifluoromethyl, phenyl, or naphthyl.

In an embodiment, L is selected from single-bond, or a substituted or unsubstituted group Z. The unsubstituted group Z is selected from the group consisting of the following groups:

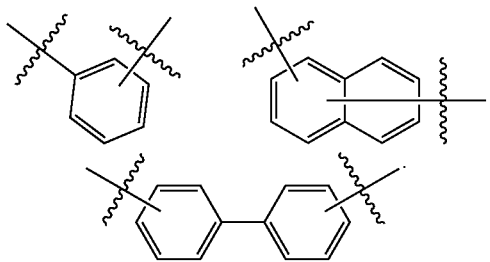

The substituted group Z has one or more substituents, each substituent independently selected from deuterium, fluorine, cyano, methyl, ethyl, isopropyl, tert-butyl, or phenyl; and when the number of the substituents is greater than 1, each substituent is identical or different.

Optionally, L is selected from single bond or the group consisting of following groups:

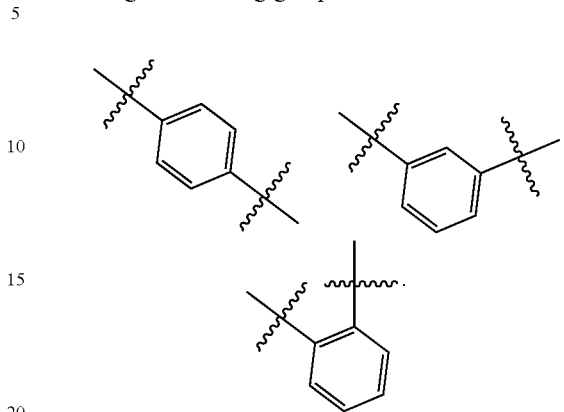

Optionally, Ar is selected from a substituted or unsubstituted aryl with 6 to 25 carbon atoms, or a substituted or unsubstituted heteroaryl with 5 to 20 carbon atoms. For example, Ar may be selected from the group consisting of a substituted or unsubstituted aryl having 6, 7, 8, 9, 10, 11, 12, 13, 14, 15, 16, 17, 18, 19, 20, 21, 22, 23, 24, or 25 carbon atoms, and a substituted or unsubstituted heteroaryl having 5, 6, 7, 8, 9, 10, 11, 12, 13, 14, 15, 16, 17, 18, 19, 20 carbon atoms.

Optionally, substituents in Ar are each independently selected from deuterium, fluorine, cyano, a alkyl with 1 to 4 carbon atoms, a fluoroalkyl with 1 to 4 carbon atoms, a deuterated alkyl with 1 to 4 carbon atoms, a trialkylsiyl with 3 to 7 carbon atoms, a cycloalkyl with 5 to 10 carbon atoms, a aryl with 6 to 12 carbon atoms, or a heteroaryl with 5 to 12 carbon atoms.

Optionally, Ar is selected from a substituted or unsubstituted phenyl, a substituted or unsubstituted naphthyl, a substituted or unsubstituted biphenyl, a substituted or unsubstituted terphenyl, a substituted or unsubstituted anthryl, a substituted or unsubstituted phenanthryl, a substituted or unsubstituted fluorenyl, a substituted or unsubstituted triphenylene, a substituted or unsubstituted pyridyl, a substituted or unsubstituted quinolyl, a substituted or unsubstituted isoquinolyl, a substituted or unsubstituted dibenzofuranyl, a substituted or unsubstituted dibenzothienyl, or a substituted or unsubstituted carbazolyl.

Optionally, substituents in Ar are each independently selected from deuterium, fluorine, cyano, methyl, ethyl, isopropyl, tert-butyl, trifluoromethyl, trideuteromethyl, trimethylsilyl, cyclopentyl, cyclohexyl, phenyl, naphthyl, biphenyl, pyridyl, dibenzofuranyl, dibenzothienyl, or carbazolyl.

In an embodiment, Ar is selected from a substituted or unsubstituted group W. The unsubstituted group W is selected from the group consisting of the following groups:

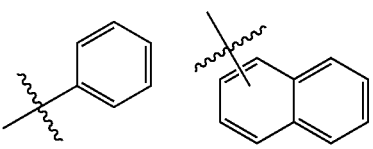

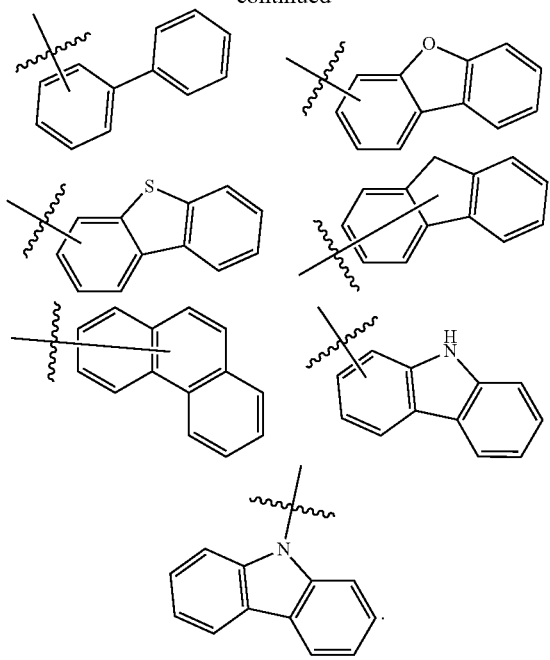

The substituted group W has one or more substituents, each substituent independently selected from deuterium, fluorine, cyano, methyl, ethyl, isopropyl, tert-butyl, trifluoromethyl, trideuteromethyl, trimethylsilyl, cyclopentyl, cyclohexyl, phenyl, naphthyl, biphenyl, or pyridyl; and when the number of the substituents is greater than 1, each substituent is identical or different.

Optionally, Ar is selected from the group consisting of the following groups:

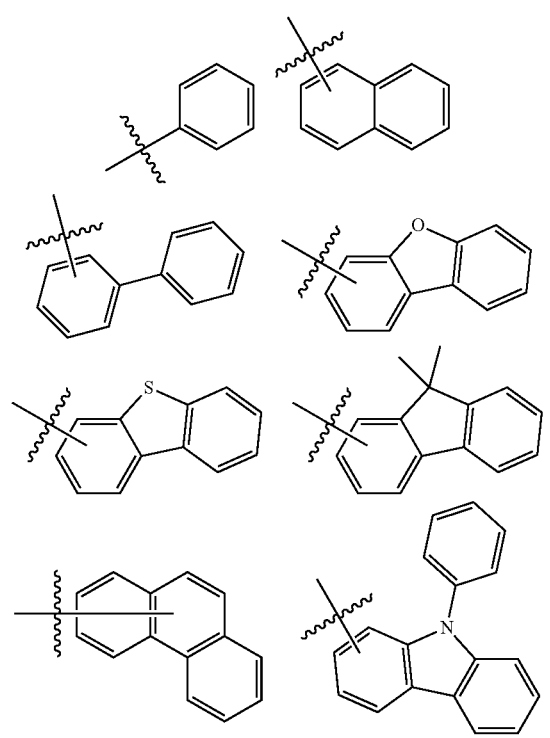

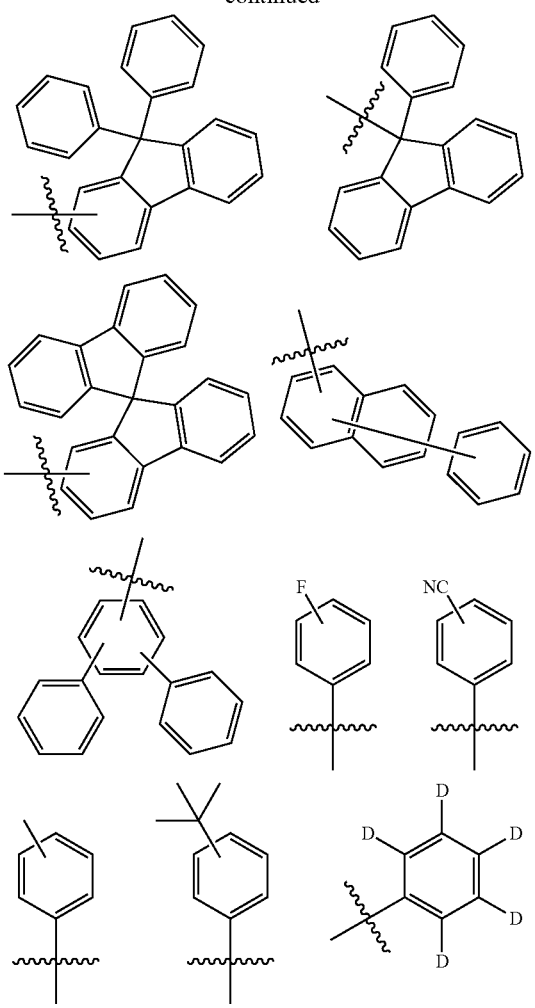

Optionally, Ar is selected from the group consisting of the following groups:

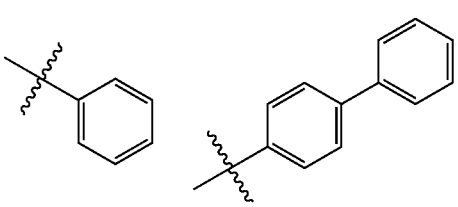

-continued
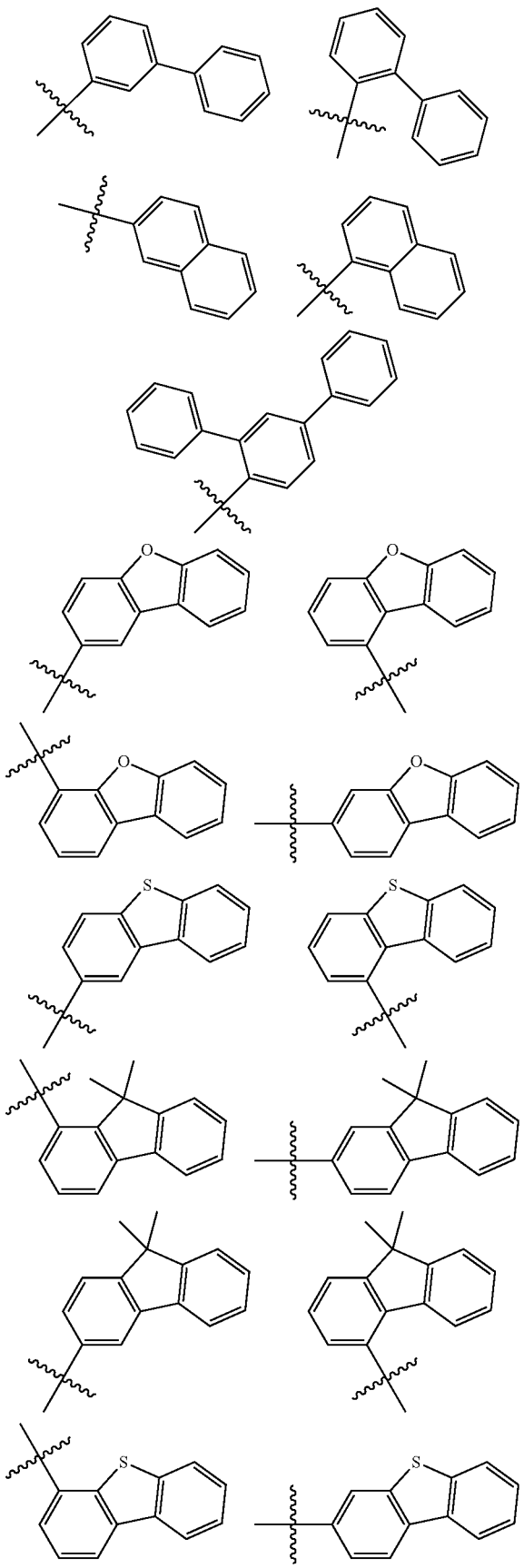
-continued
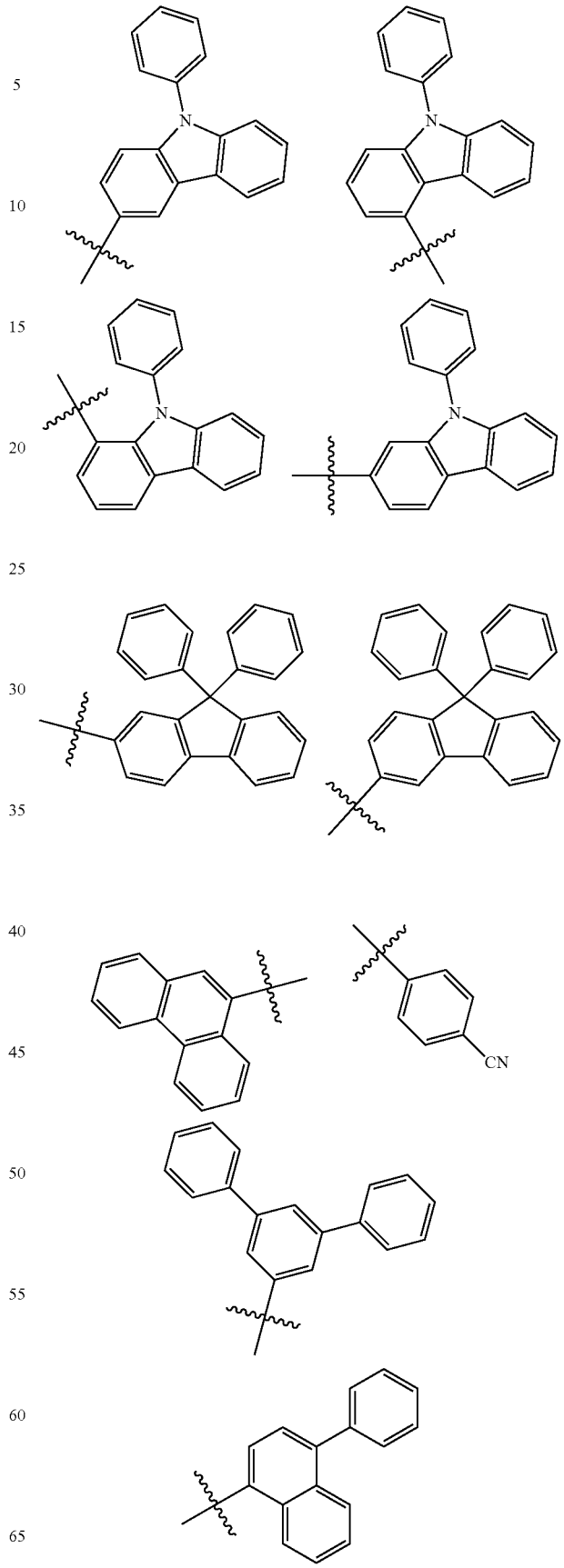

-continued

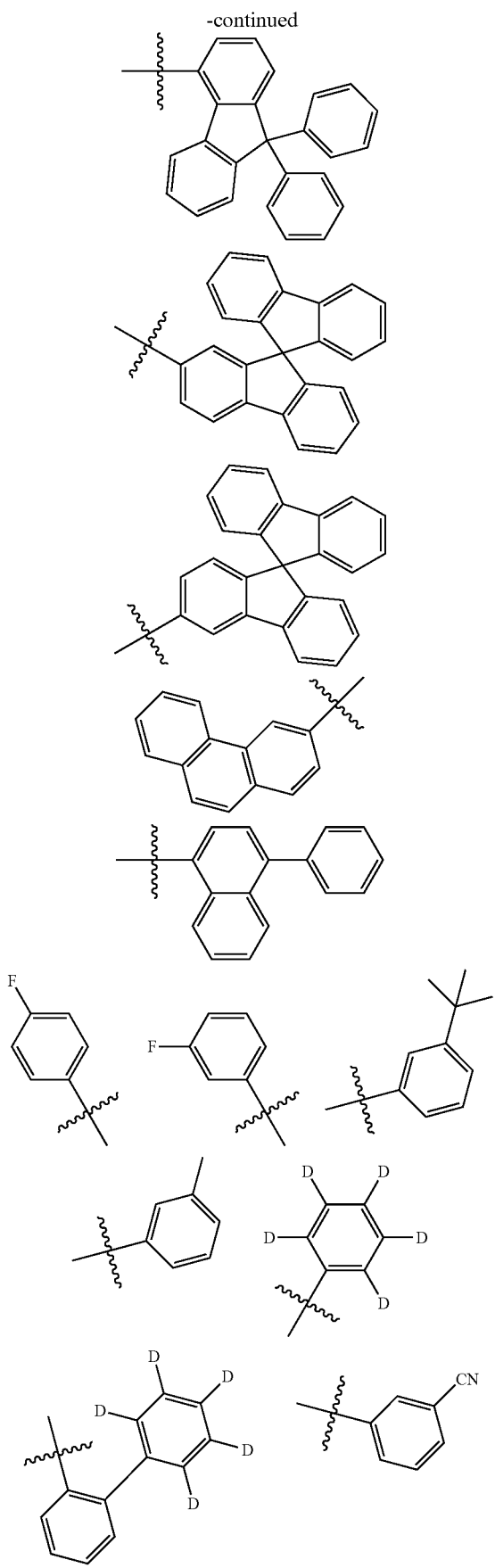

-continued

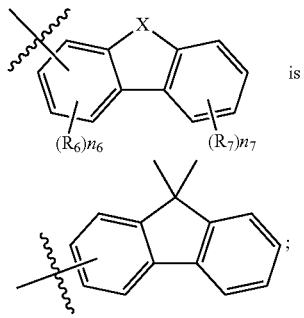

Optionally, $R_1$ and $R_2$ are identical or different, and are each independently selected from methyl, ethyl, isopropyl, tert-butyl, or phenyl.

Optionally, $R_3$, $R_4$, $R_5$, $R_6$ and $R_7$ are identical or different, and are each independently selected from deuterium, fluorine, cyano, methyl, ethyl, isopropyl, tert-butyl, trifluoromethyl, trideuteromethyl, or phenyl.

In an embodiment, $n_3$, $n_4$, $n_5$, $n_6$, and $n_7$ are each independently selected from 0 or 1.

In a preferred embodiment,

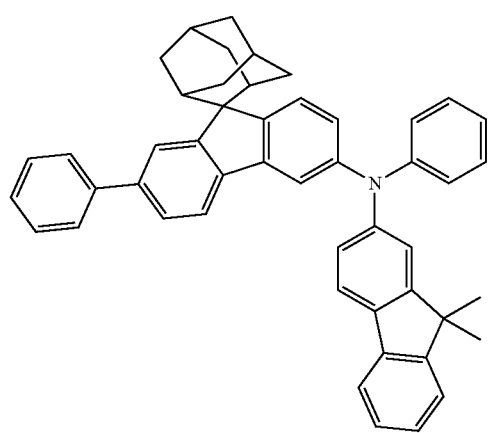

L is single bond; and Ar is selected from the above mentioned substituted or unsubstituted aryl groups (e.g., substituted or unsubstituted phenyl, substituted or unsubstituted naphthyl, substituted or unsubstituted biphenyl, substituted or unsubstituted phenanthryl). In this case, the organic compound, when used in an organic electroluminescent device, can further improve the comprehensive performance of the device.

Optionally, the organic compound is selected from the group consisting of the following compounds:

-continued
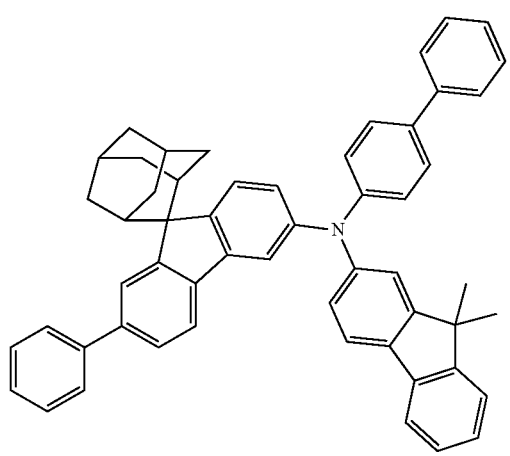
2
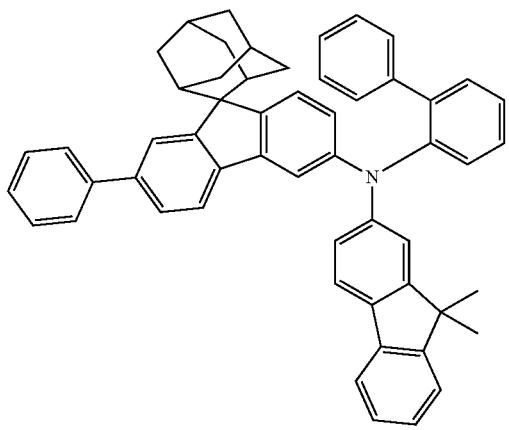
5
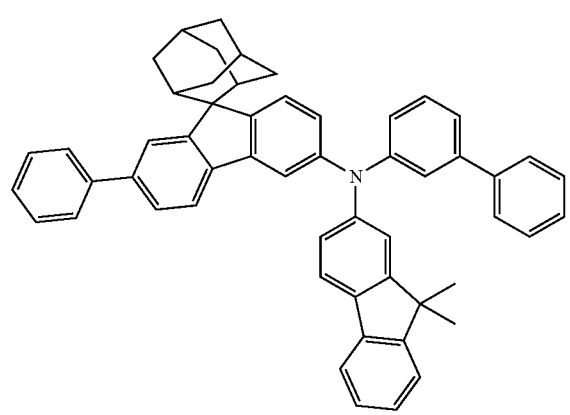
3
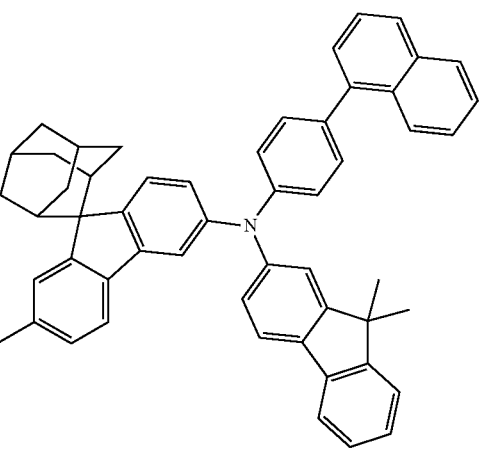
6
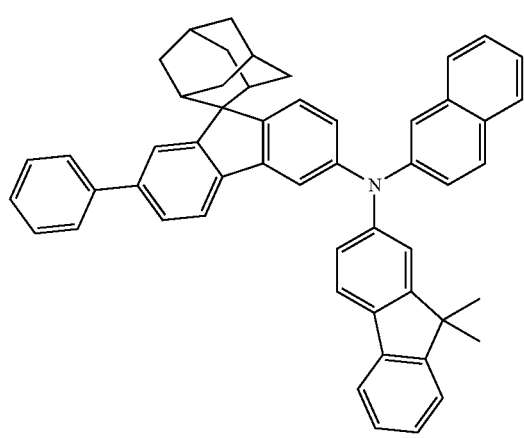
4
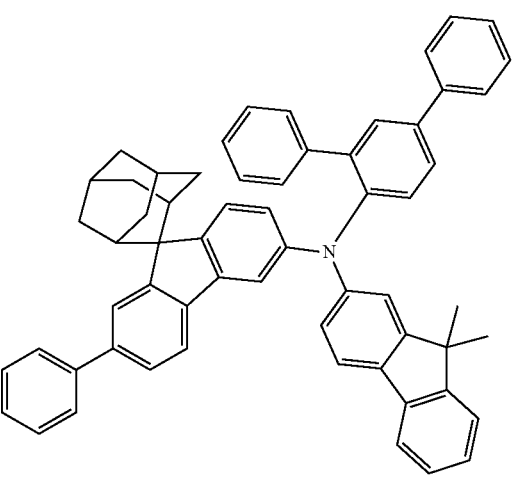
7

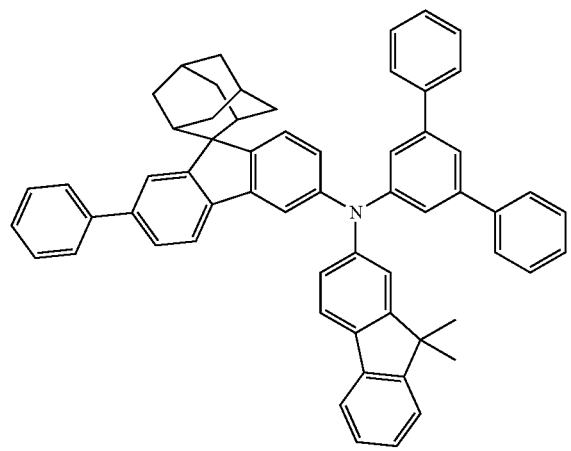
8
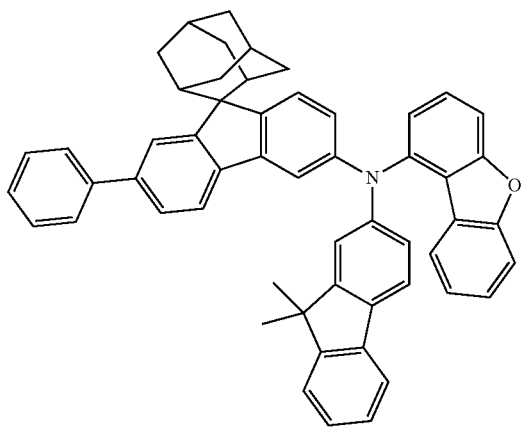
11
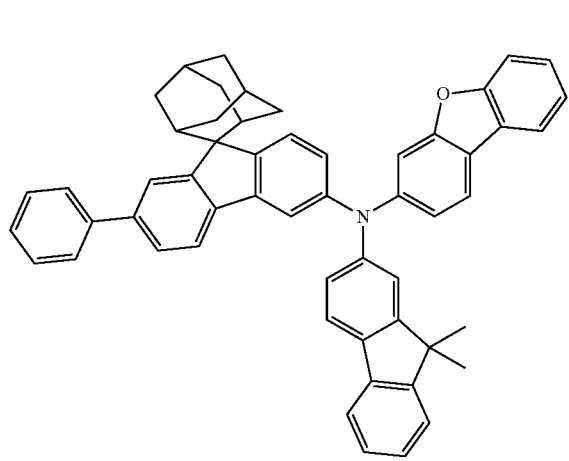
9
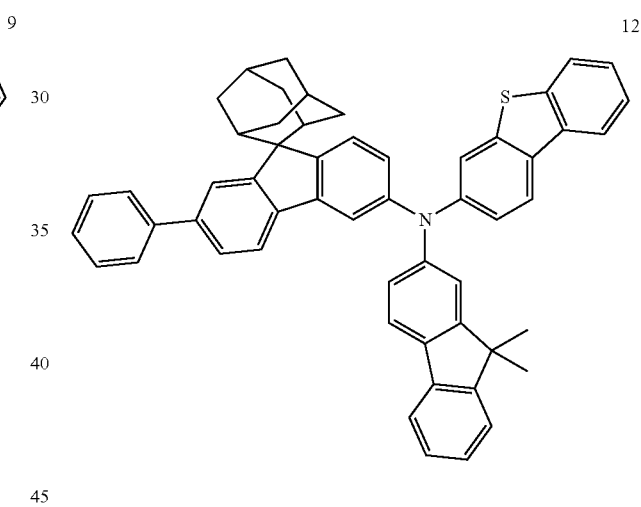
12
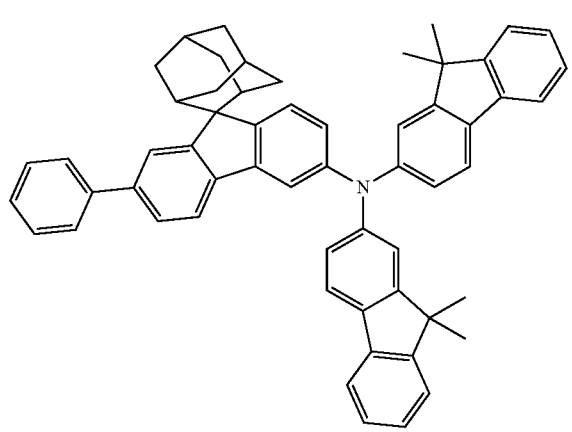
10
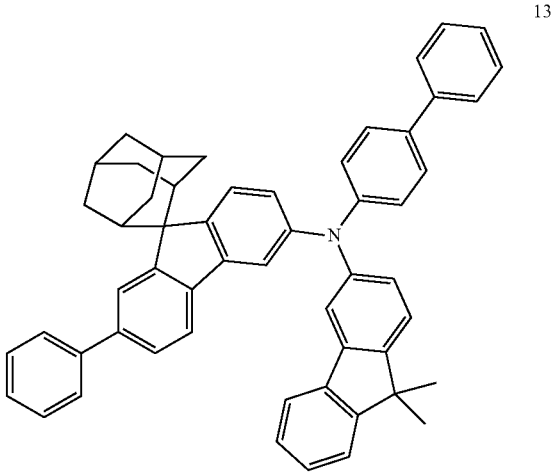
13

14
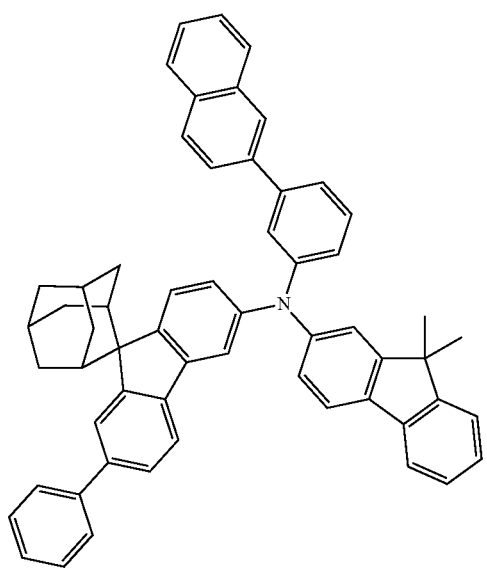
15
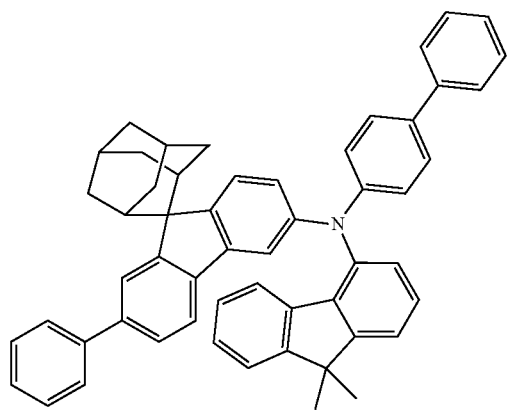
16
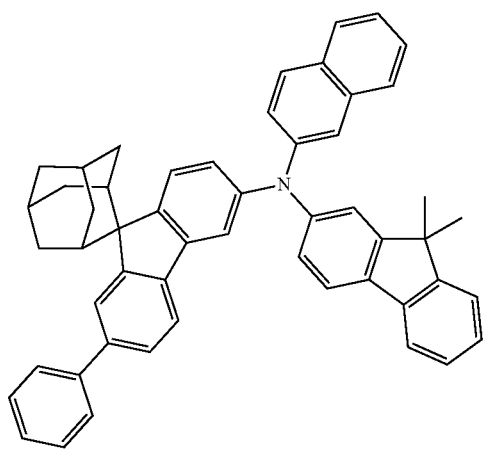
17
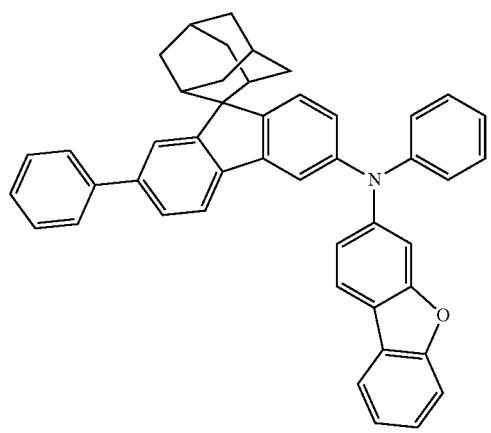
18
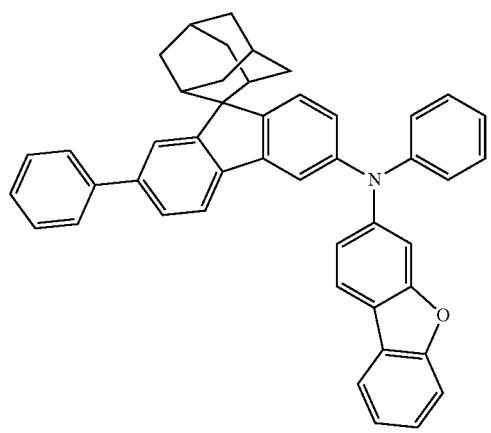
19
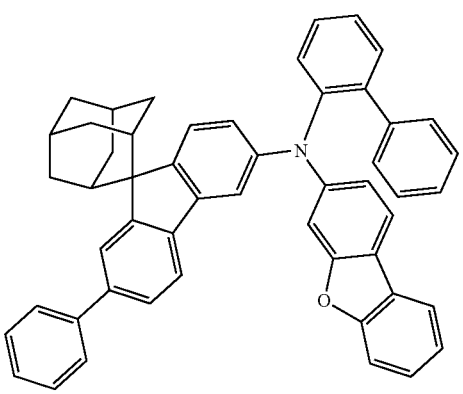

20
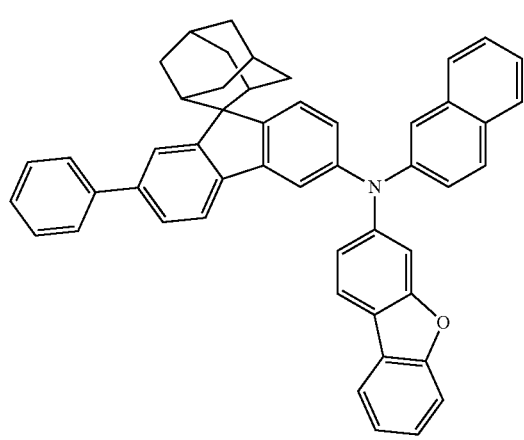
21
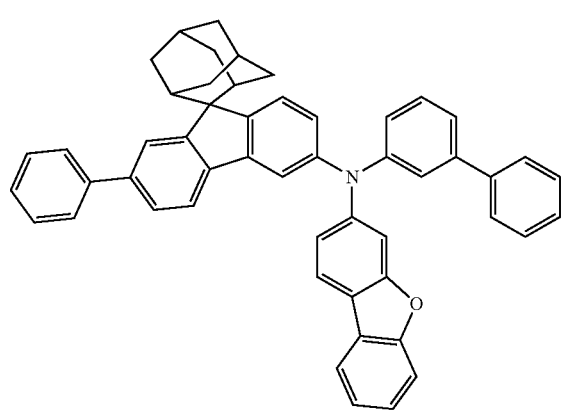
22
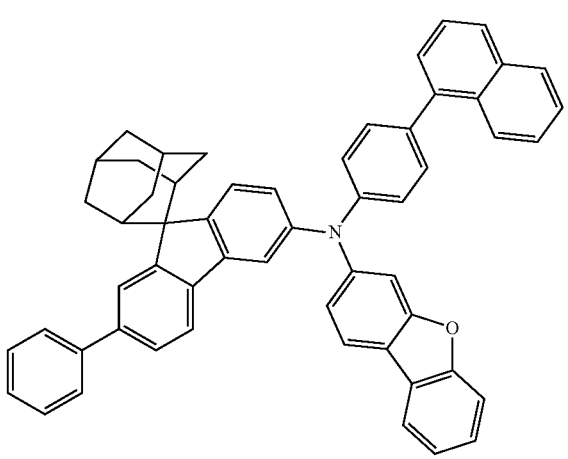
23
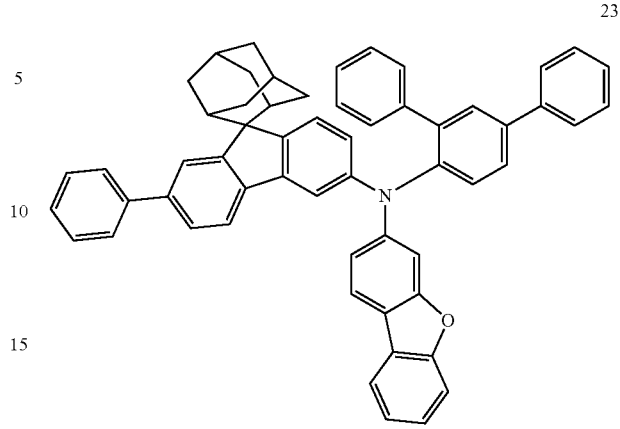
24
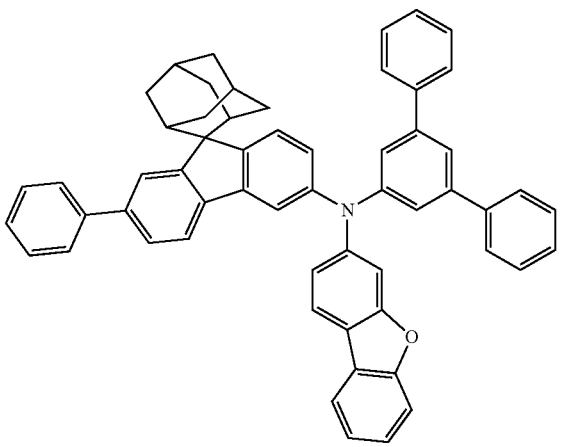
25
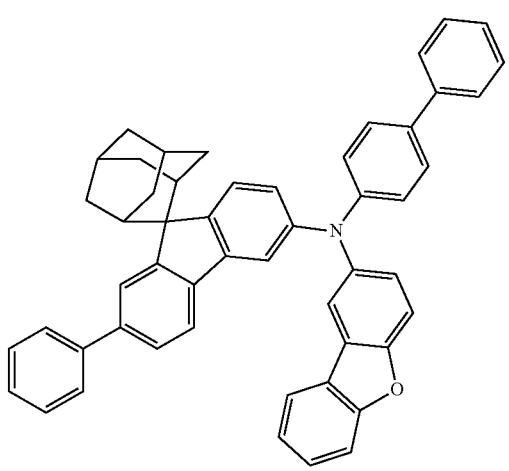

26
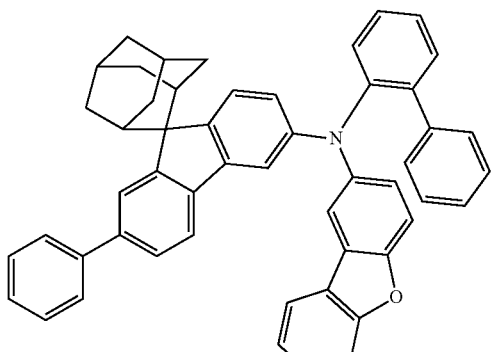
27
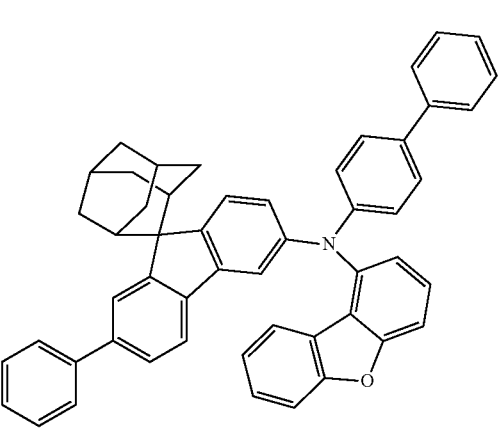
28
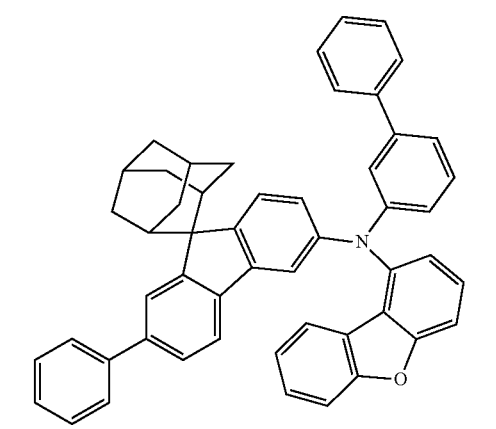
29
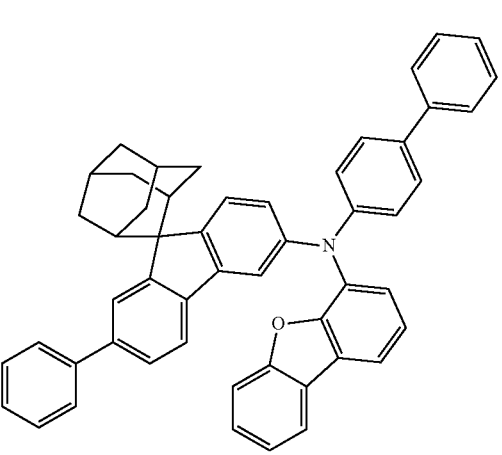
30
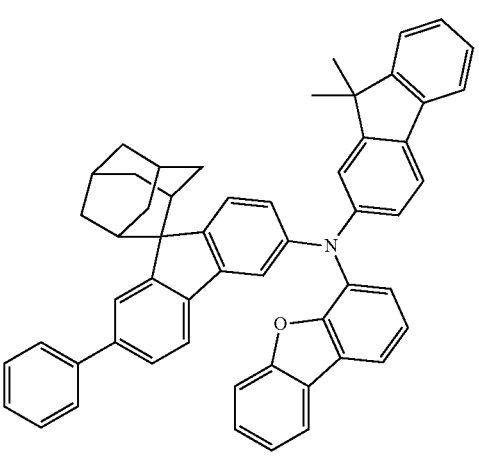
31
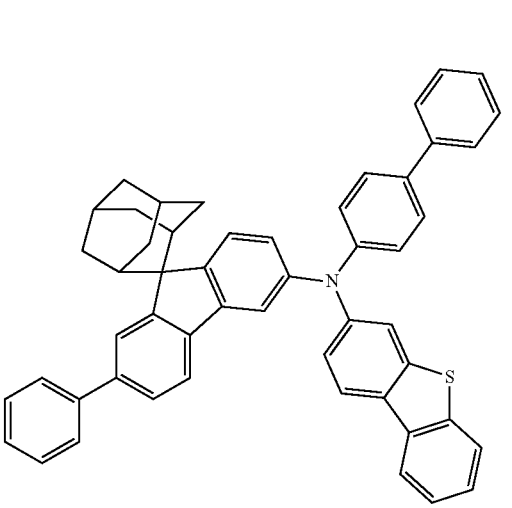
32
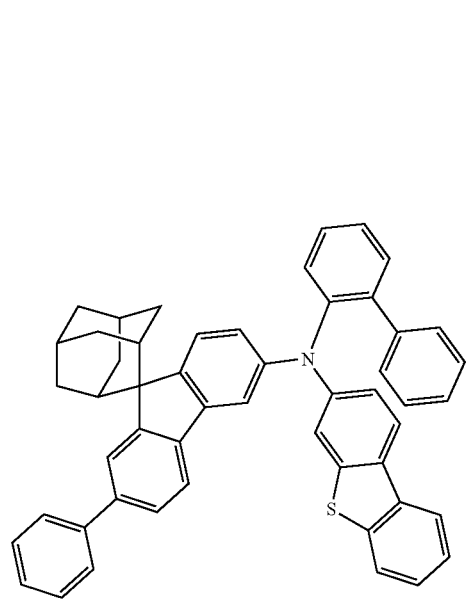

31
-continued
33
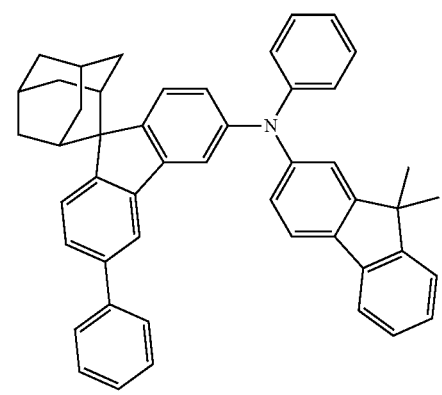
34
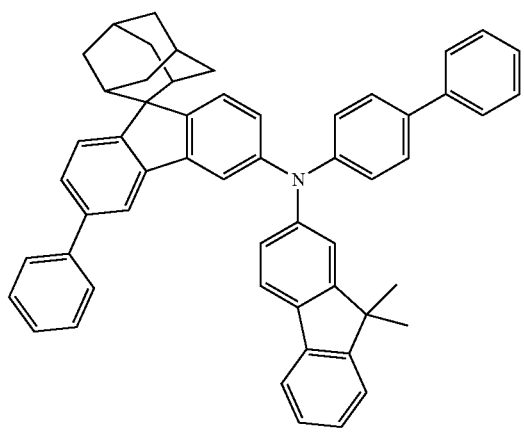
35
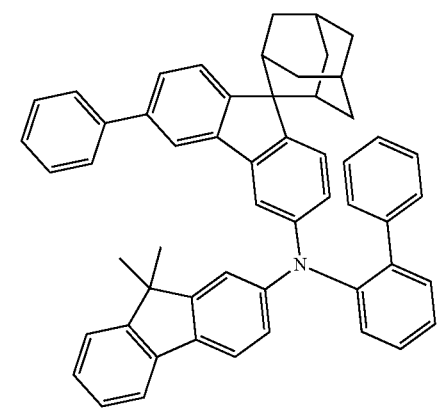
36
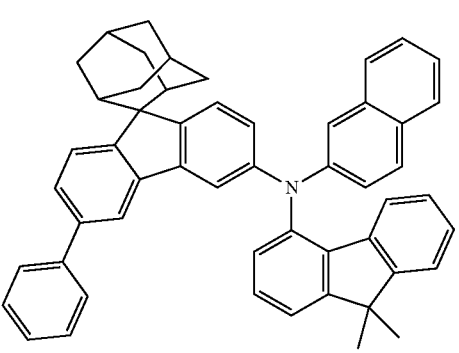
32
-continued
37
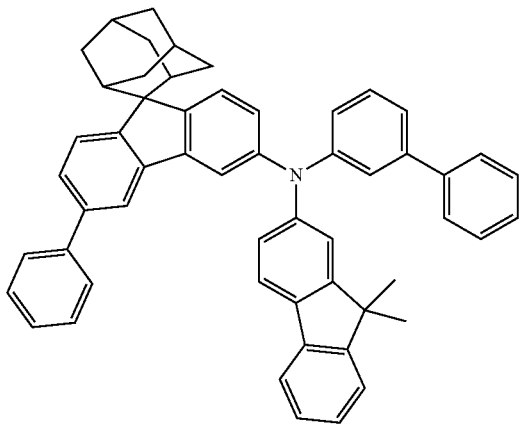
38
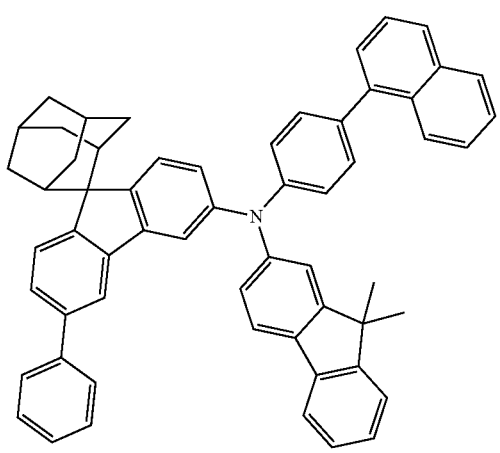
39
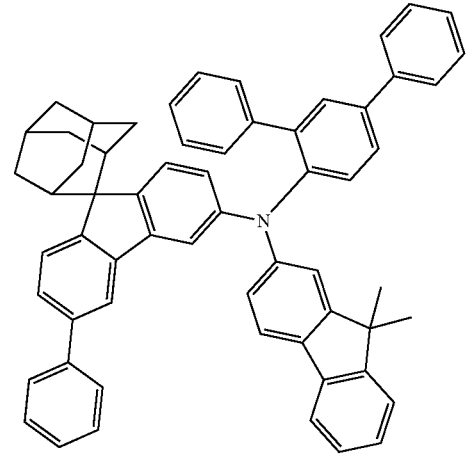

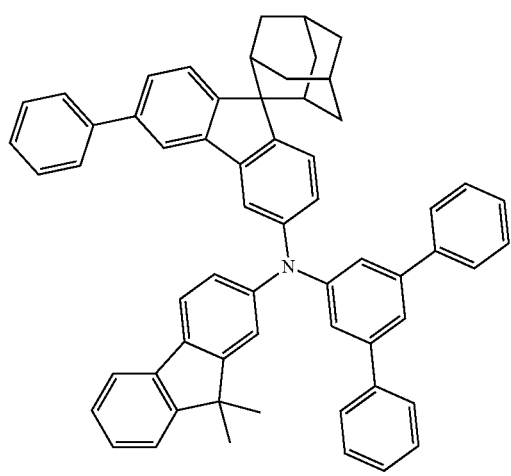
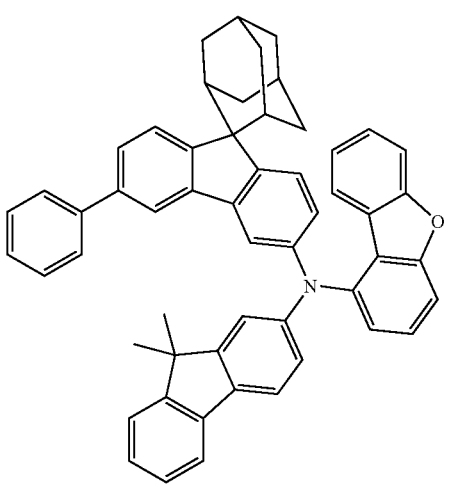
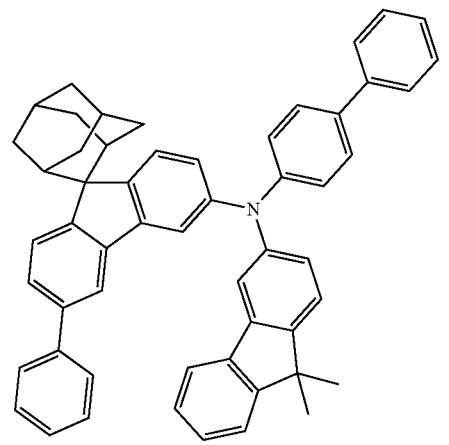

46
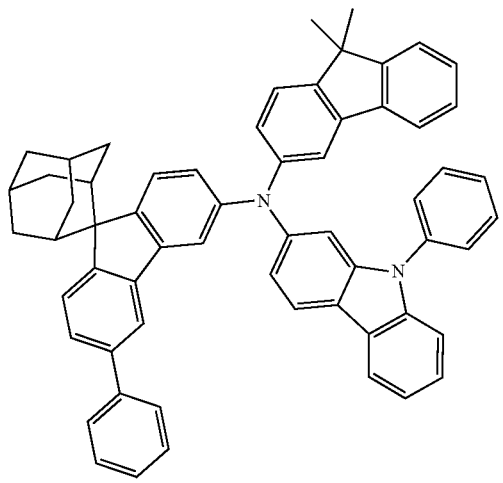
47
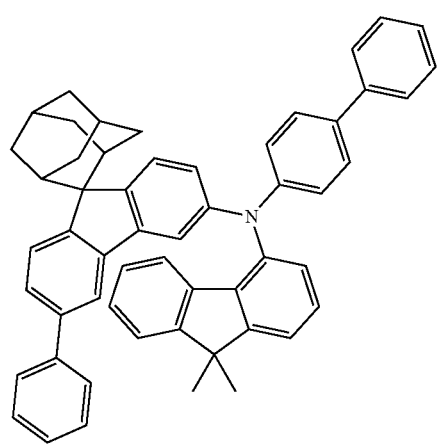
48
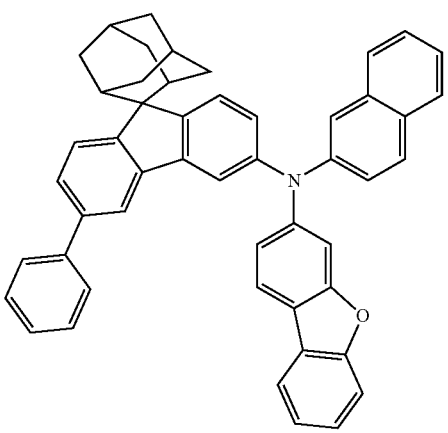
49
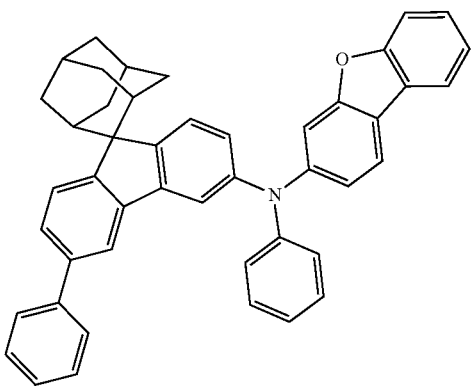
50
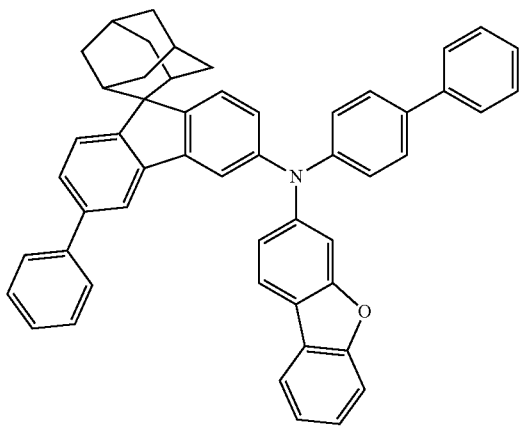
51
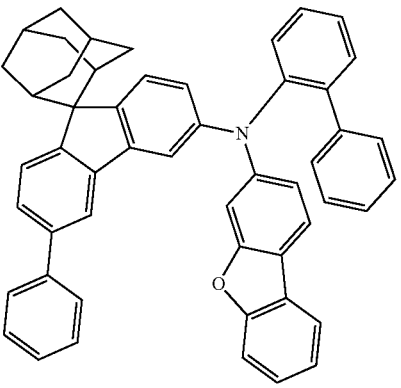
52
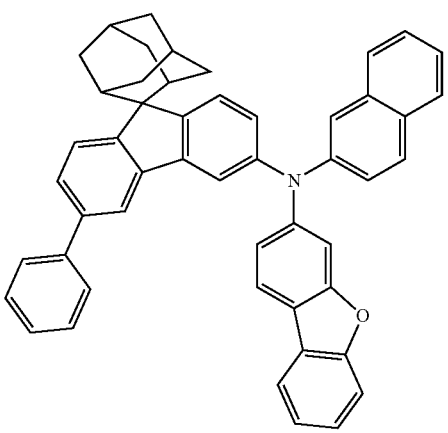

53
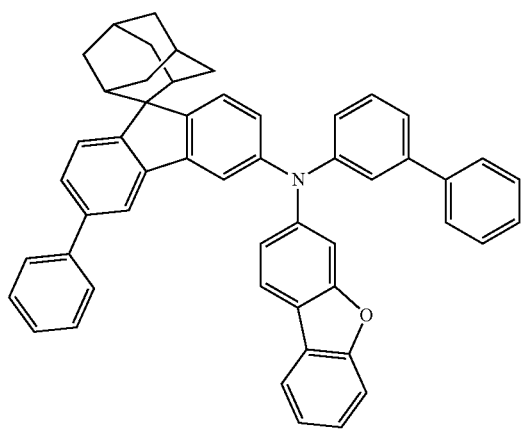
54
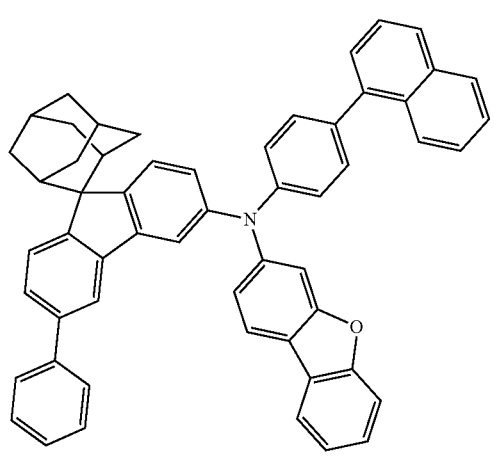
55
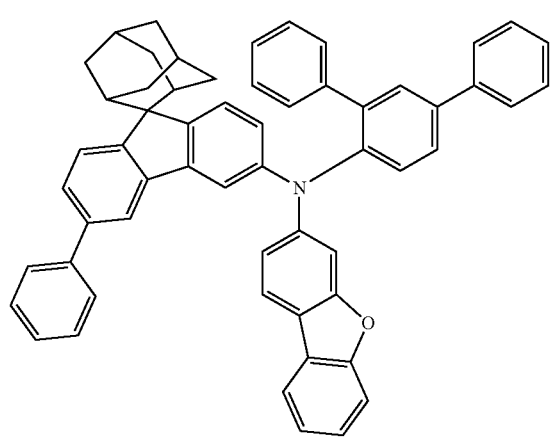
56
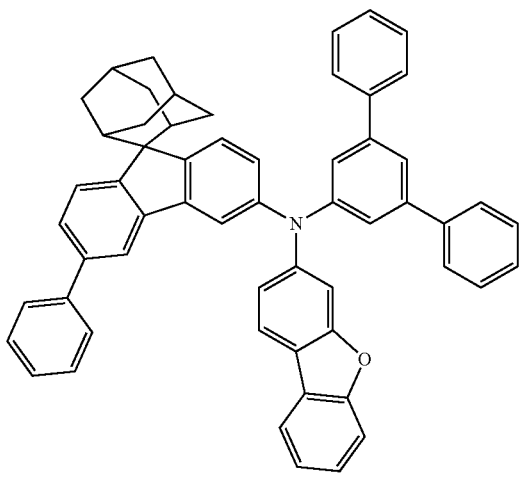
57
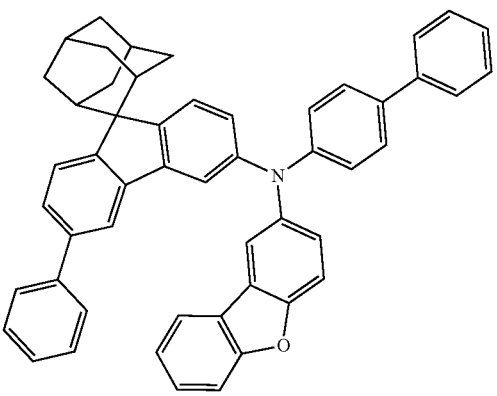
58
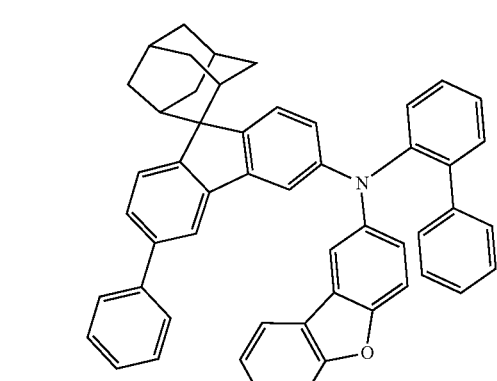
59
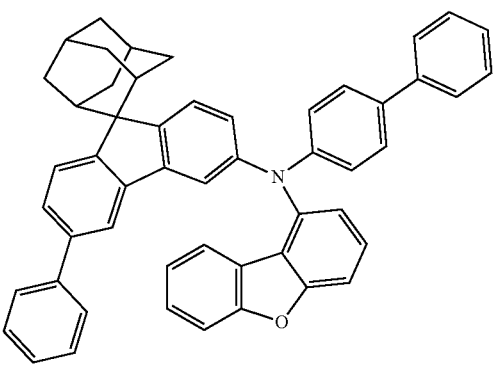

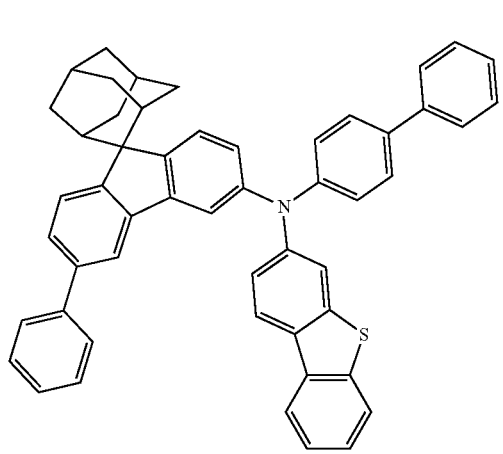
60
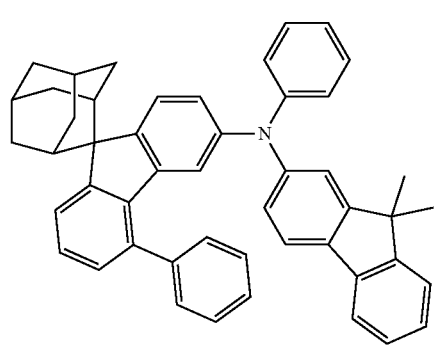
61
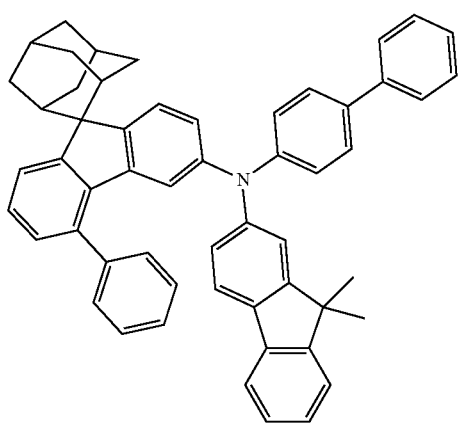
62
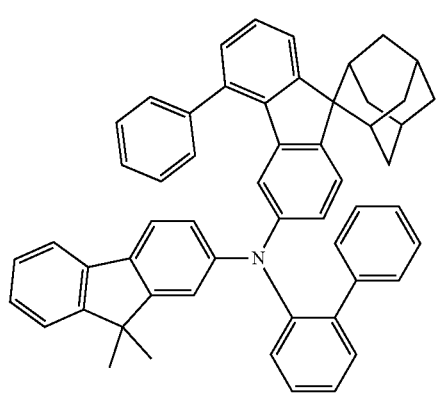
63
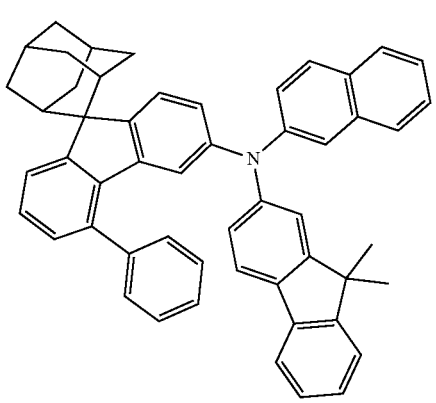
64
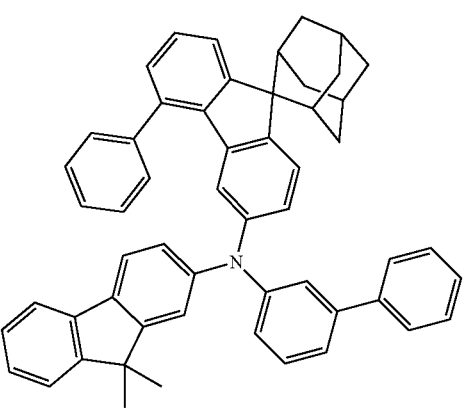
65
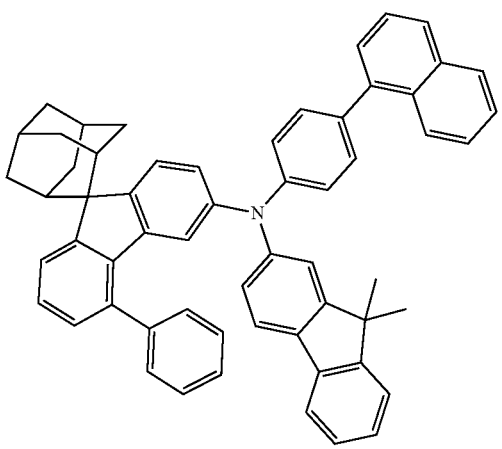
66

67
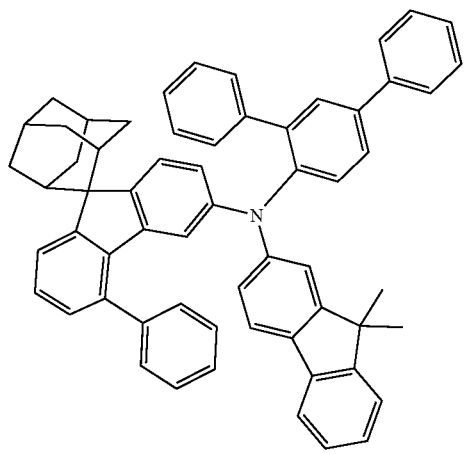
68
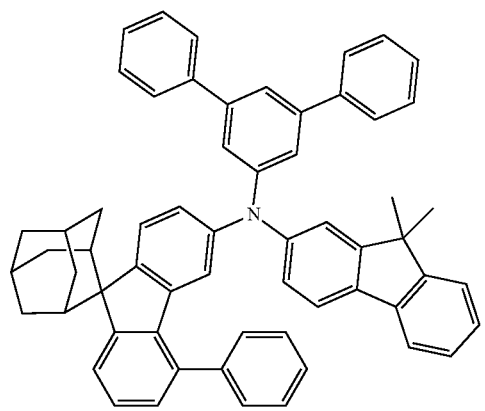
69
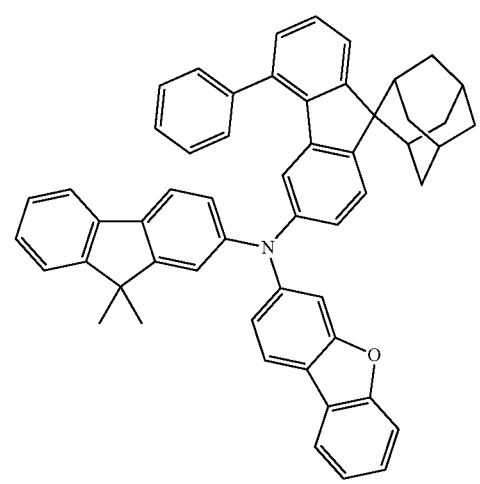
70
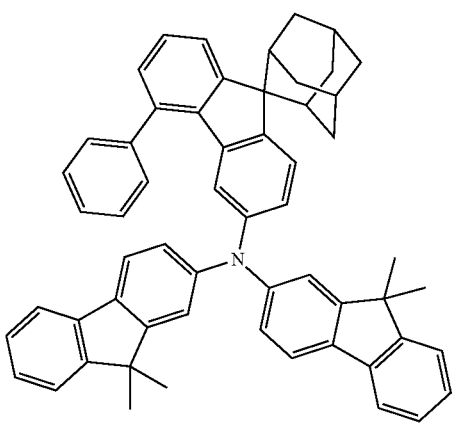
71
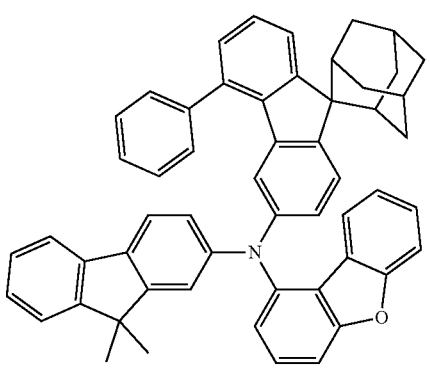
72
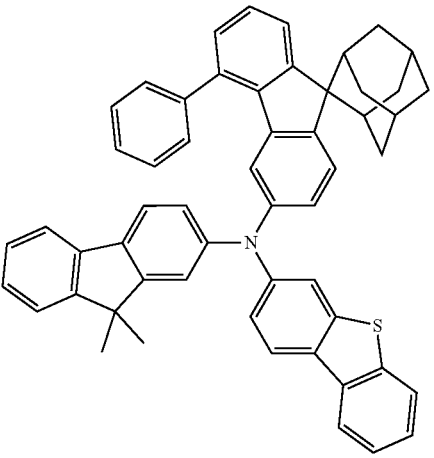
73
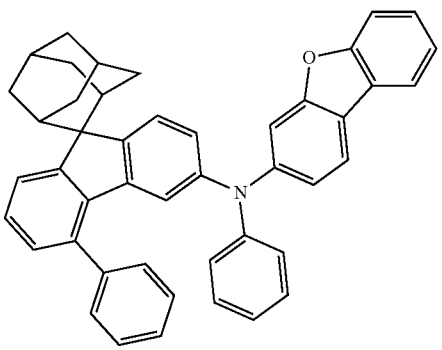

74
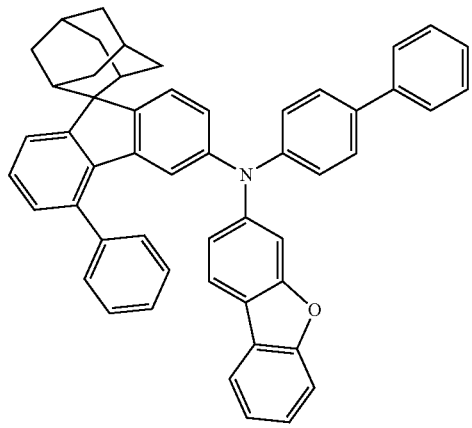
75
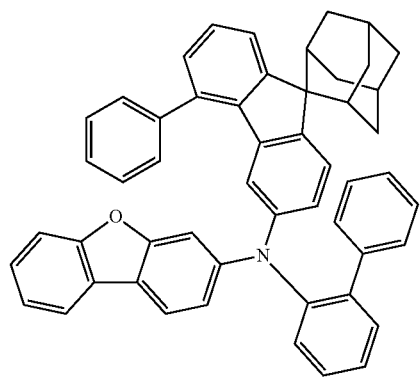
77
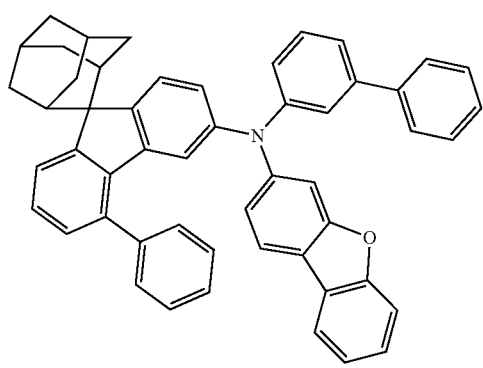
78
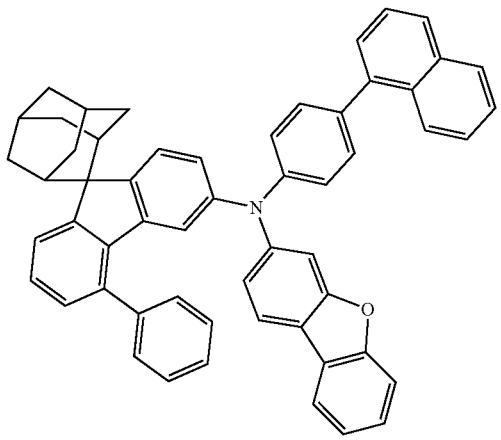
79
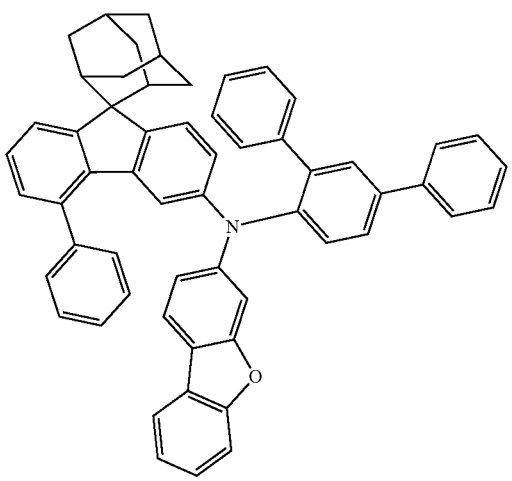
80
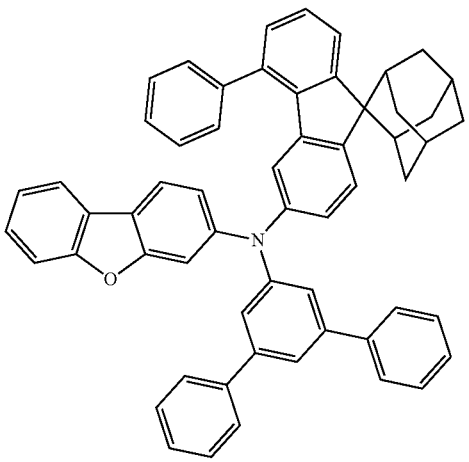

81
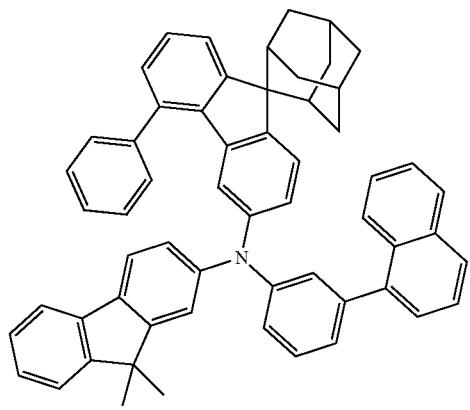
82
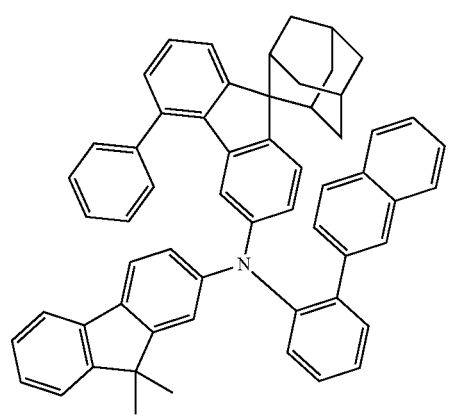
83
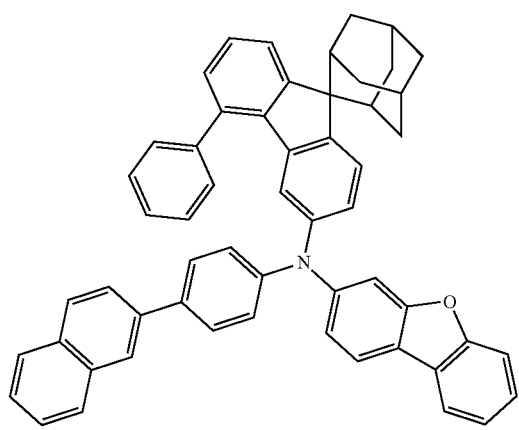
84
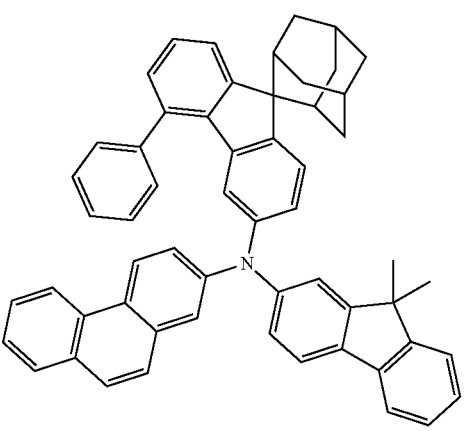
85
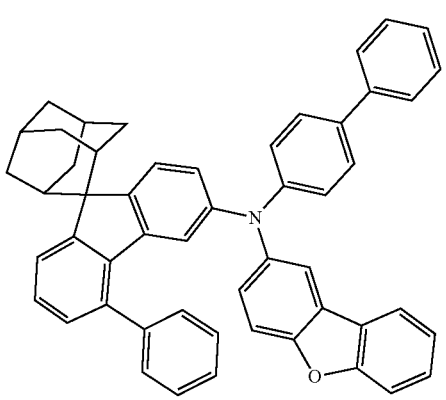
86
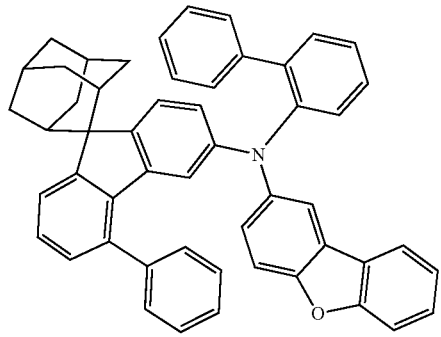
87
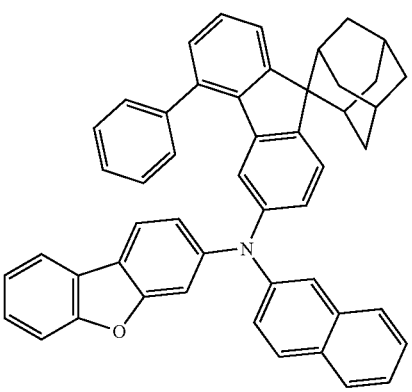

88
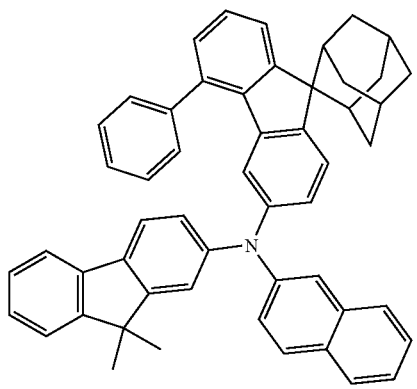
89
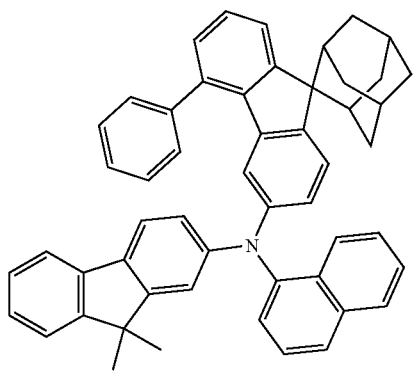
90
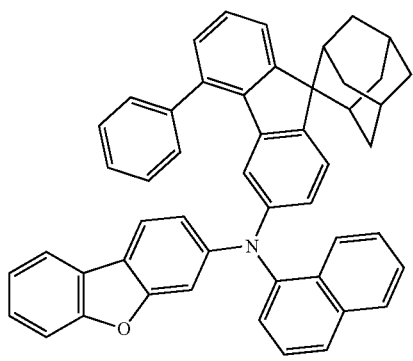
91
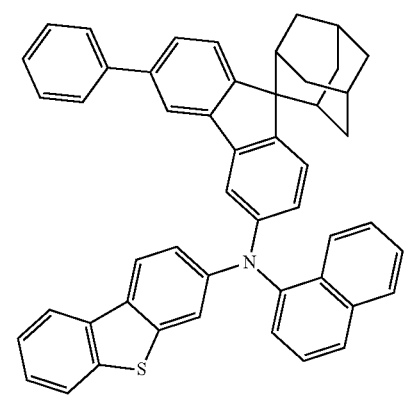
92
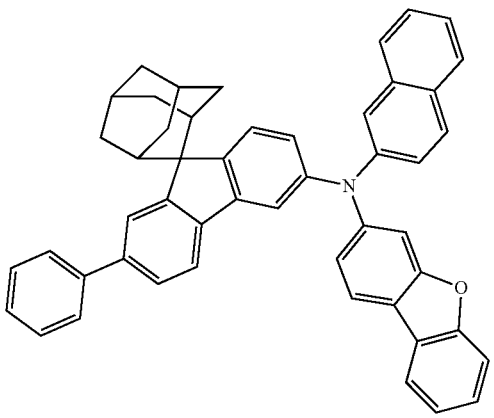
93
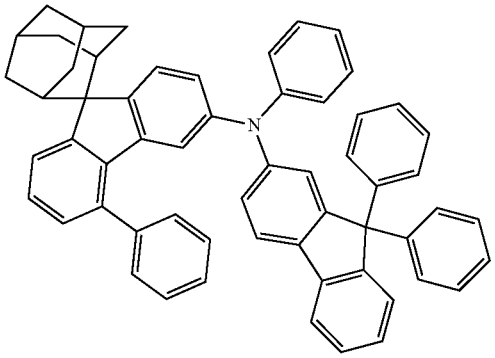
94
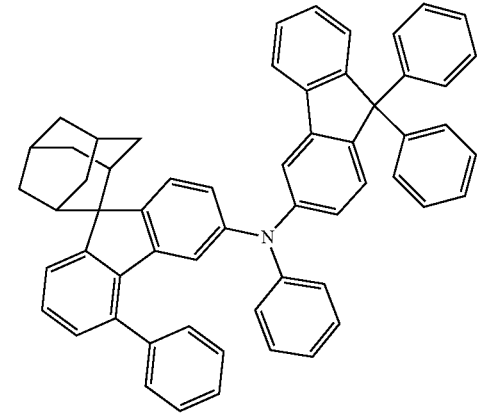
95
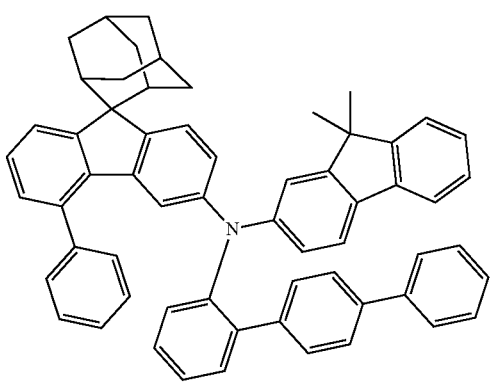

96
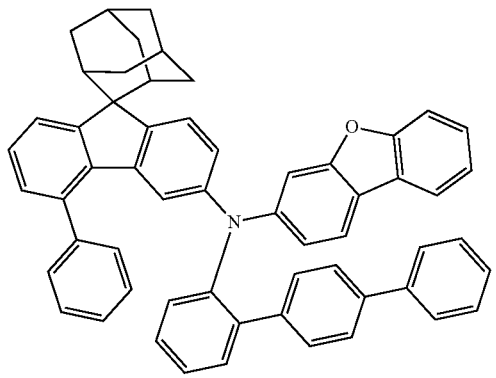
97
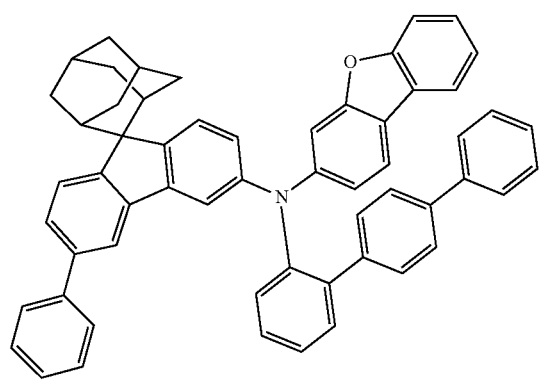
98
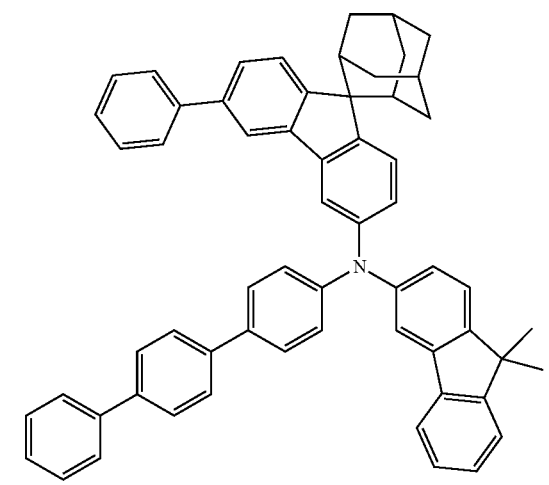
99
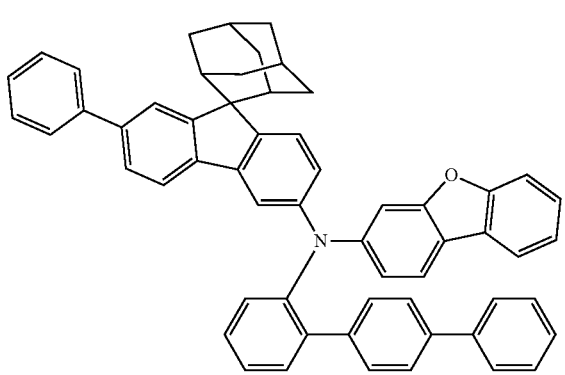
100
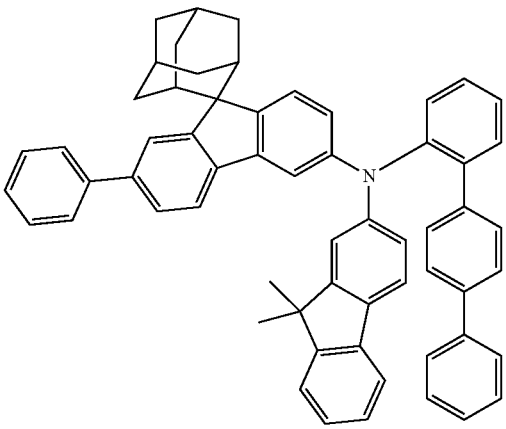
101
102
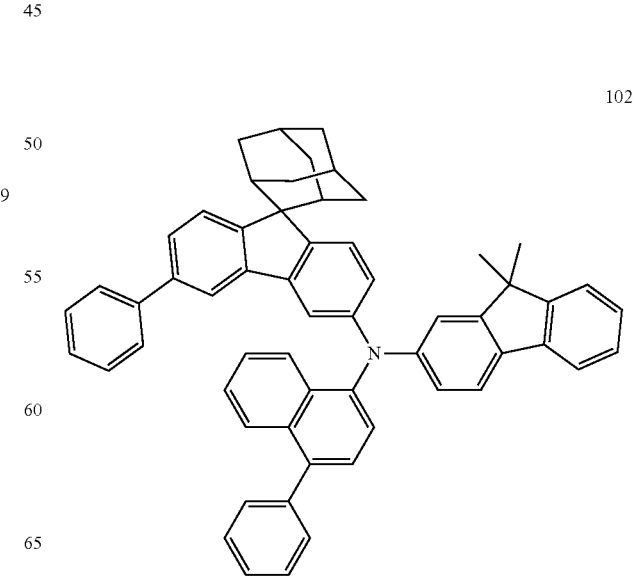

-continued
103
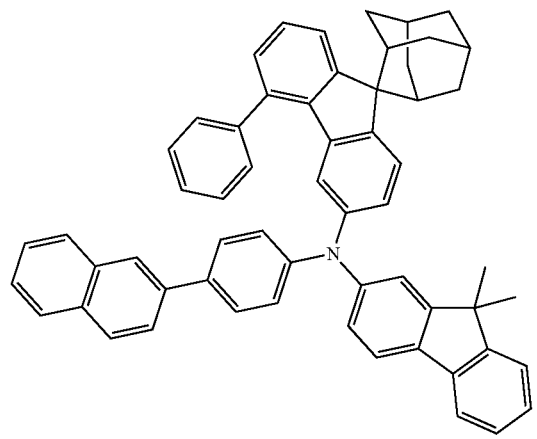
104
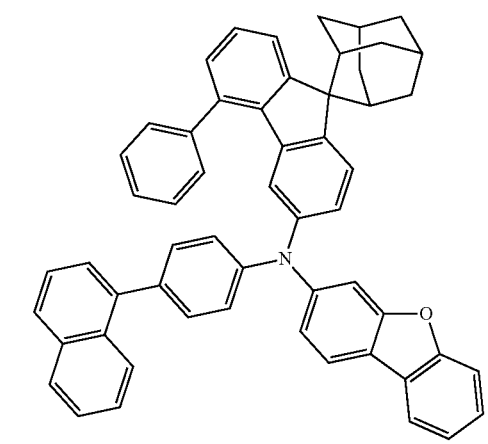
105
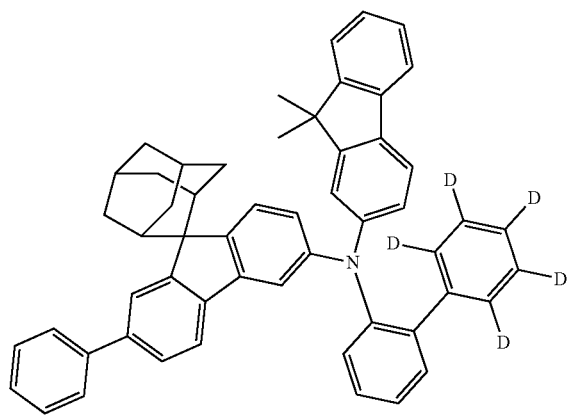
-continued
106
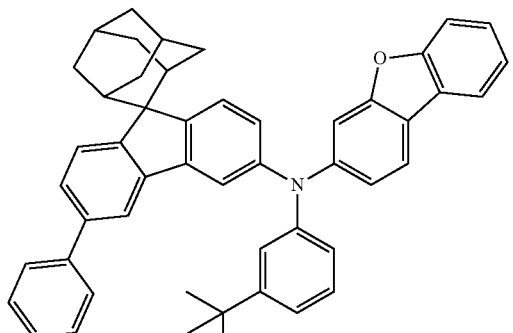
107
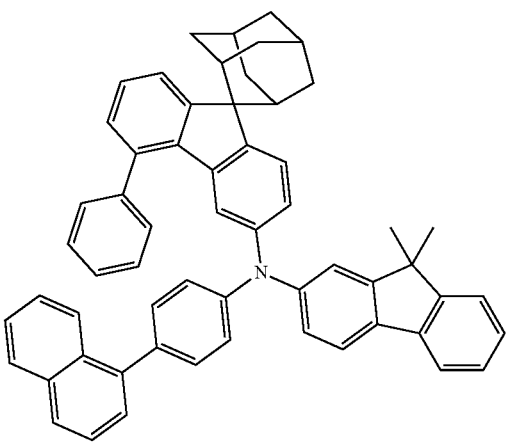
108
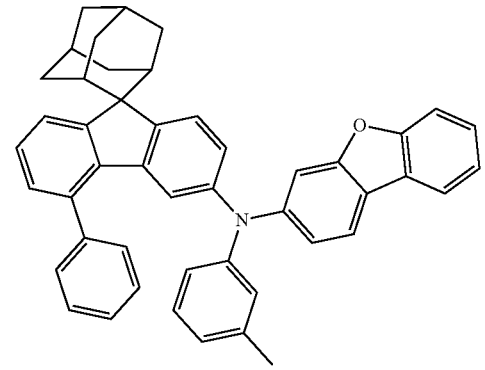
109
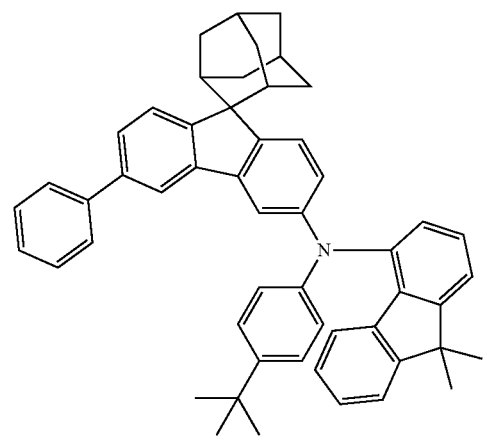

110
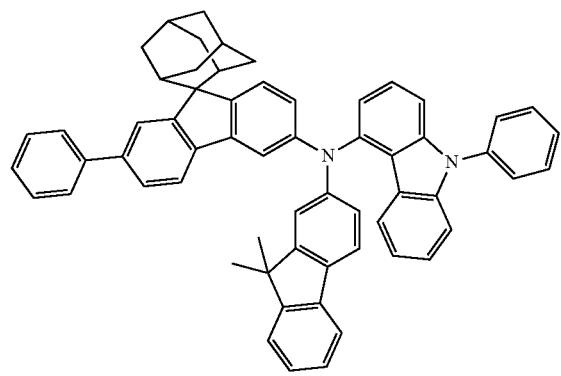
111
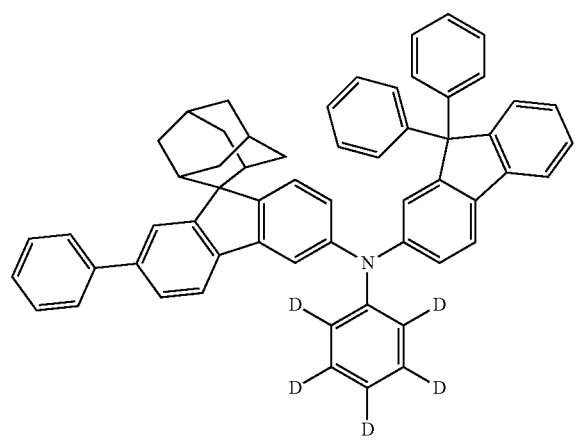
112
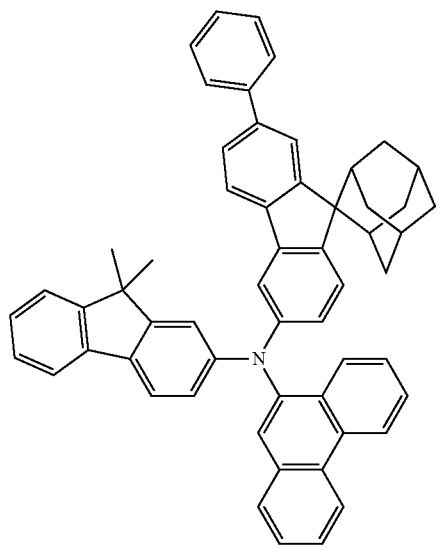
113
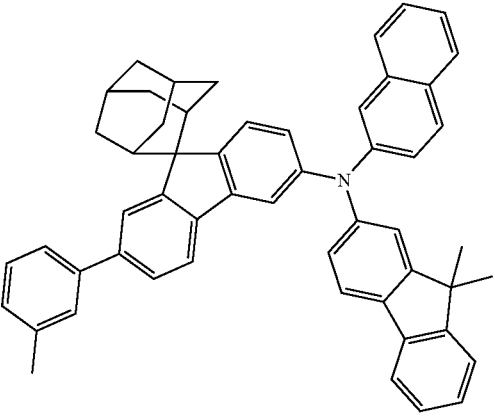
114
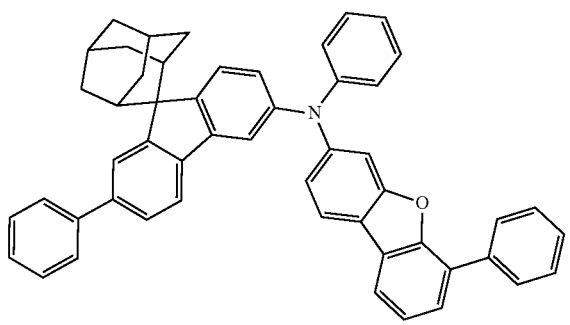
115
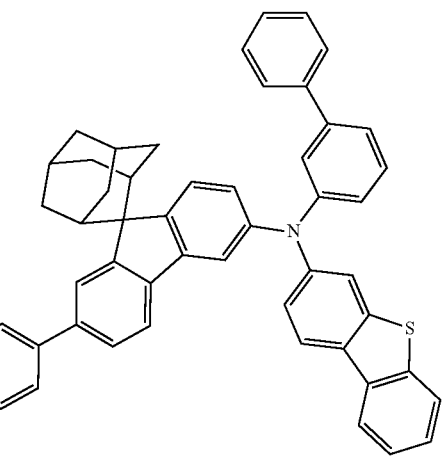

-continued

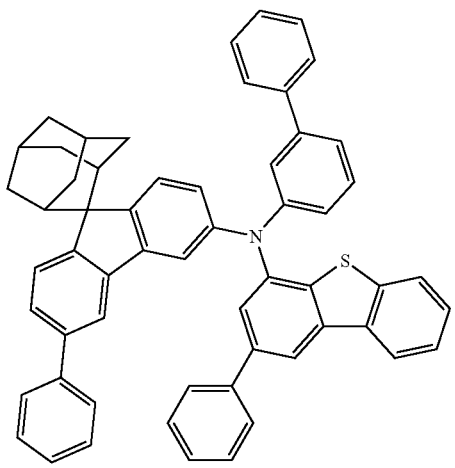

116

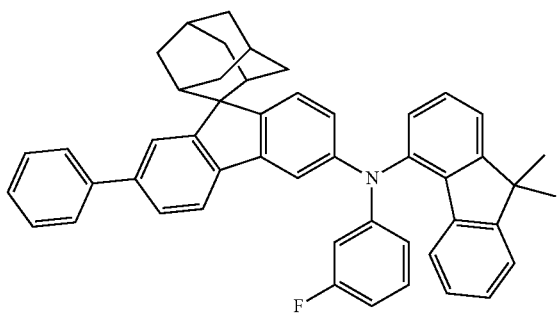

117

Synthesis methods of the organic compounds provided in the present disclosure are not particularly limited, and those of ordinary skill in the art can determine suitable synthesis methods based on the organic compounds of the present disclosure combined with preparation methods provided in the Synthesis Examples section. In other words, the Synthesis Examples section of the present disclosure merely provides some exemplary methods for preparing the organic compounds. Raw materials used can be obtained commercially or by methods well known in the art. Those of ordinary skill in the art can obtain all the organic compounds provided in the present disclosure based on these exemplary preparation methods. Not all specific methods for preparing the organic compounds will be described herein in detail. These methods should not be interpreted by those of ordinary skill in the art as limitations on the present disclosure.

The present disclosure, in a second aspect, provides comprises an electronic component comprising an anode and a cathode that are disposed opposite to each other, and a functional layer disposed between the anode and the cathode, where the functional layer comprises the organic compound described above. The organic compound provided in the present disclosure can be used to form at least one organic film layer in the functional layer, so that the electronic component has both beneficial efficiency characteristics and beneficial service life characteristics.

Optionally, the functional layer comprises a hole transport layer. The hole transport layer comprises the organic compound provided in the present disclosure.

Optionally, the electronic component is an organic electroluminescent device or a photoelectric conversion device.

Optionally, the electronic component is an organic electroluminescent device, and the hole transport layer comprises a first hole transport layer and a second hole transport layer that are stacked in layers. The first hole transport layer is closer to the anode than the second hole transport layer, and the second hole transport layer comprises the organic compound.

According to an embodiment, the electronic component is an organic electroluminescent device. As shown in FIG. 1, the organic electroluminescent device may comprise an anode 100, a hole transport layer 320, an organic emissive layer 330 as an energy conversion layer, an electron transport layer 340, and a cathode 200 that are stacked in sequence.

In the present disclosure, the anode 100 comprises an anode material, which is preferably a high-work function material contributing to injection of holes into the functional layer. Specific examples of the anode material include, but are not limited to: metals such as nickel, platinum, vanadium, chromium, copper, zinc, gold, and alloys thereof; metal oxides such as zinc oxide, indium oxide, indium tin oxide (ITO), and indium zinc oxide (IZO); combinations of metals and oxides, such as ZnO:Al or $SnO_2$:Sb; and conductive polymers such as poly(3-methylthiophene), poly[3, 4-(ethylene-1,2-dioxy)thiophene] (PEDT), polypyrrole, and polyaniline. Preferably, a transparent electrode comprising indium tin oxide (ITO) is included as the anode.

In the present disclosure, the hole transport layer 320 may be a single-layer structure or a two-layer structure. Optionally, as shown in FIG. 1, the hole transport layer 320 comprises a first hole transport layer 321 and a second hole transport layer 322 that are stacked in layers. The first hole transport layer 321 is closer to the anode 100 than the second hole transport layer 322. Optionally, the second hole transport layer 322 is composed of a material selected from the organic compounds of the present disclosure.

The material of the first hole transport layer 321 may be selected from phthalocyanine derivatives, naphthalocyanine derivatives, porphyrin derivatives, benzidine triarylamine, styrylamine triarylamine, diamine triarylamine, and other types of materials, which can be selected by those of ordinary skill in the art referring to the existing technologies. For example, the material of the first hole transport layer 321 is selected from the group consisting of the following compounds:

HT-1

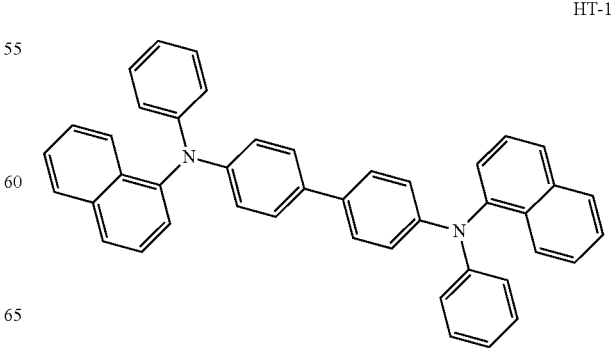

HT-2

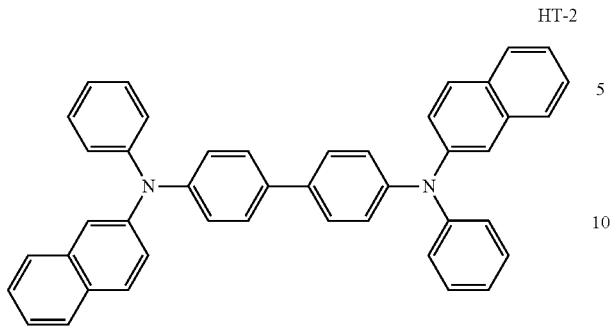

HT-3

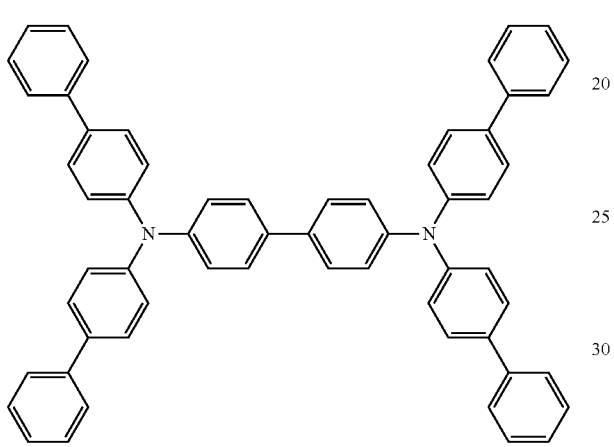

HT-4

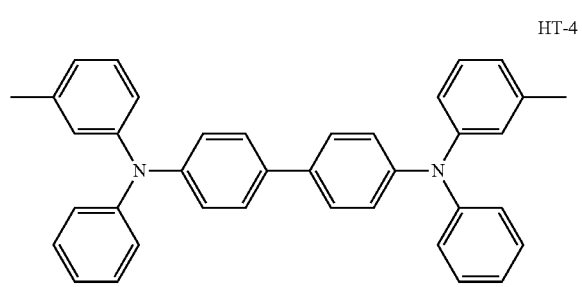

HT-5

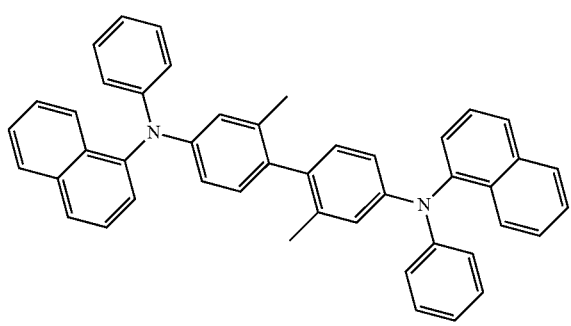

HT-6

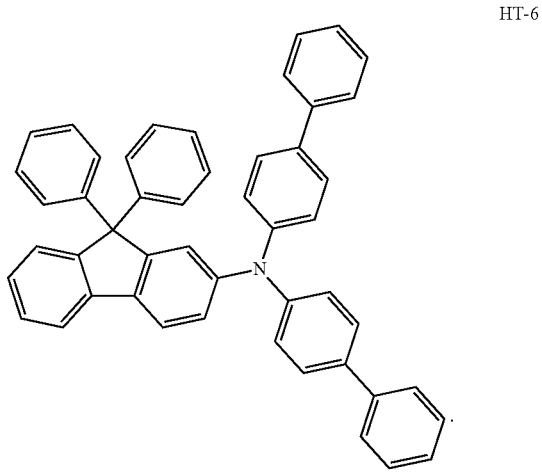 [SMILES: c1ccc(-c2ccc(N(c3ccc(-c4ccccc4)cc3)c3ccc4c(c3)C(c3ccccc3)(c3ccccc3)c3ccccc3-4)cc2)cc1]

In a specific embodiment, the material of the first hole transport layer 321 is NPB (i.e., HT-1).

In the present disclosure, the organic emissive layer 330 may be composed of a single luminescent material, or may include a host material and a dopant material. In an embodiment, the organic emissive layer 330 is composed of a host material and a dopant material. Holes injected into the organic emissive layer 330 and electrons injected into the organic emissive layer 330 can recombine in the organic emissive layer 330 to form excitons. The excitons transmit energy to the host material, and the host material transmits the energy to the dopant material, thereby enabling the dopant material to emit light. The host material may be a metal chelating compound, a stilbene derivative, an aromatic amine derivative, a dibenzofuran derivative, or other types of materials, and the present disclosure is not particularly restricted in this respect. In a specific embodiment, the host material is RH-1. The dopant material may be a compound having a condensed aryl ring or a derivative thereof, a compound having a heteroaryl ring or a derivative thereof, an aromatic amine derivative, or other materials, and the present disclosure is not particularly restricted in this respect. In a specific embodiment, the dopant material is $Ir(piq)_2(acac)$.

In the present disclosure, the electron transport layer 340 may be a single-layer structure, or a multi-layer structure, and may comprise one or more electron transport materials. The electron transport materials may typically include metal complexes and/or nitrogen-containing heterocyclic derivatives. The metal complex material may, for example, be selected from LiQ, $Alq_3$, $Bepq_2$, etc. The nitrogen-containing heterocyclic derivative may be an aromatic ring having a nitrogen-containing 6-membered ring or 5-membered ring skeleton, a fused aromatic ring compound having a nitrogen-containing 6-membered ring or 5-membered ring skeleton, etc. Specific examples include, but are not limited to, 1,10-phenanthroline compounds such as BCP, Bphen, NBphen, DBimiBphen, BimiBphen, and the like, or compounds having a structure as shown below:

ET-1

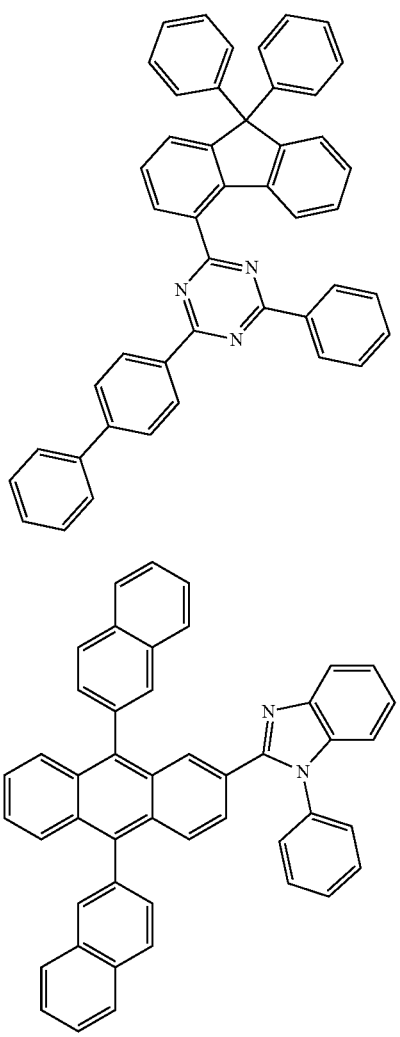

ET-2

ET-3

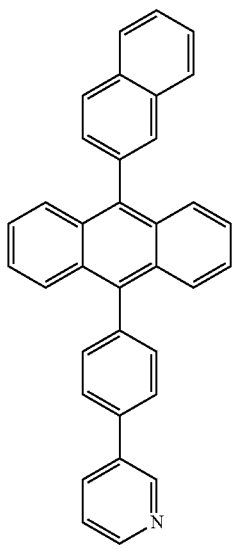

ET-4

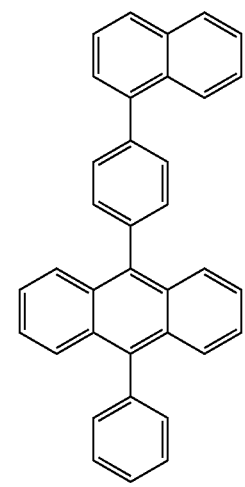

ET-5

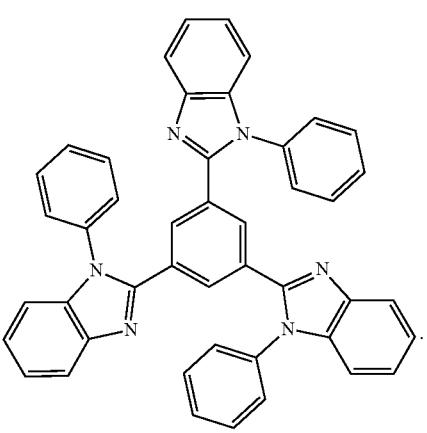

In a specific embodiment, the electron transport layer 340 is composed of TPBi (i.e., ET-5) and LiQ.

In the present disclosure, the cathode 200 may comprise a cathode material, which is a low-work function material contributing to injection of electrons into the functional layer. Specific examples of the cathode material include, but are not limited to, metals such as magnesium, calcium, sodium, potassium, titanium, indium, yttrium, lithium, gadolinium, aluminum, silver, tin, lead, and alloys thereof; or multilayer materials such as LiF/Al, Liq/Al, LiO$_2$/Al, LiF/Ca, LiF/Al, and BaF$_2$/Ca. Preferably, a metal electrode comprising silver and magnesium is included as the cathode.

Optionally, as shown in FIG. 1, a hole injection layer 310 may be further provided between the anode 100 and the first hole transport layer 321 to enhance the ability to inject holes into the hole transport layer. The hole injection layer 310 may be composed of a material selected from benzidine derivatives, starburst arylamine compounds, phthalocyanine derivatives, or other materials, and the present disclosure is not particularly limited in this respect. For example, the hole injection layer 310 may be composed of m-MTDATA or HAT-CN.

Optionally, as shown in FIG. 1, an electron injection layer 350 may be further provided between the cathode 200 and the electron transport layer 340 to enhance the ability to inject electrons into the electron transport layer 340. The electron injection layer 350 may comprise an inorganic material such as alkali metal sulfides, alkali metal halides, Yb, or may comprise a complex of an alkali metal and an organic substance. For example, the electron injection layer 350 may comprise LiQ or Yb.

Optionally, as shown in FIG. 1, the hole injection layer 310, the first hole transport layer 321, the second hole transport layer 322, the organic emissive layer 330, the electron transport layer 340, and the electron injection layer 350 form a functional layer 300.

Optionally, the organic electroluminescent device is a red light-emitting device.

Figure 3:
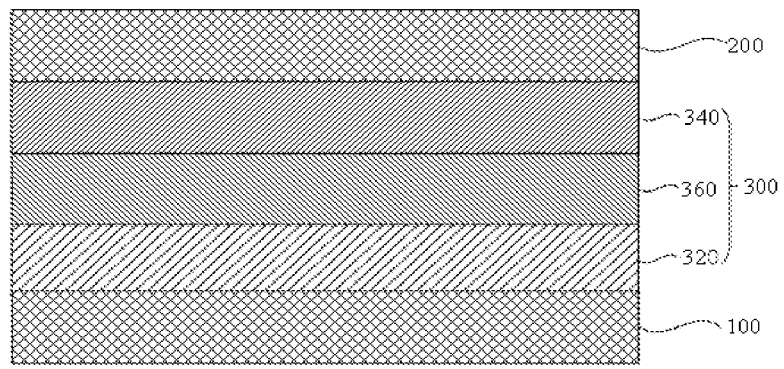
FIG. 3 is a schematic structural diagram of a photoelectric conversion device according to an embodiment of the present disclosure.

According to another embodiment, the electronic component is a photoelectric conversion device. As shown in FIG. 3, the photoelectric conversion device may include an anode 100 and a cathode 200 that are disposed opposite to each other, and a functional layer 300 disposed between the anode 100 and the cathode 200. The functional layer 300 comprises the organic compound provided in the present disclosure.

Optionally, as shown in FIG. 3, the functional layer 300 comprises a hole transport layer 320. The hole transport layer 320 comprises the organic compound of the present disclosure. The hole transport layer 320 may be composed of the organic compound provided in the present disclosure, or may be composed of the organic compound provided in the present disclosure together with other materials.

Optionally, as shown in FIG. 3, the photoelectric conversion device may include an anode 100, a hole transport layer 320, a photoelectric conversion layer 360, an electron transport layer 340, and a cathode 200 that are stacked in sequence. Optionally, the photoelectric conversion device is a solar cell, especially an organic thin-film solar cell. For example, the solar cell may include an anode, a hole transport layer, a photoelectric conversion layer, an electron transport layer, and a cathode that are stacked in sequence. The hole transport layer comprises the organic compound of the present disclosure.

The present disclosure, in a third respect, provides an electronic apparatus including the electronic component described above.

Figure 2:
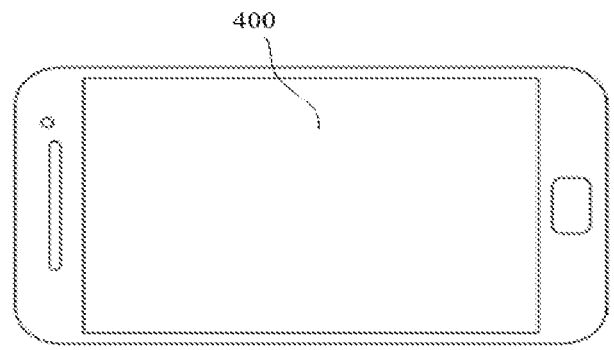
FIG. 2 is a schematic structural diagram of an electronic apparatus according to an embodiment of the present disclosure.

According to an embodiment, as shown in FIG. 2, the electronic apparatus provided in the present disclosure is a first electronic apparatus 400. The electronic apparatus may include the above described organic electroluminescent device. The first electronic apparatus 400 may be, for example, a display apparatus, a lighting apparatus, an optical communication apparatus, or other type of electronic apparatus, which, for example, may include, but are not limited to, computer screens, mobile phone screens, televisions, electronic paper, emergency lamps, optical modules, etc. Since the electronic apparatus comprises the above organic electroluminescent device, it brings the same beneficial effects, which are not repeated herein in the present disclosure.

Figure 4:
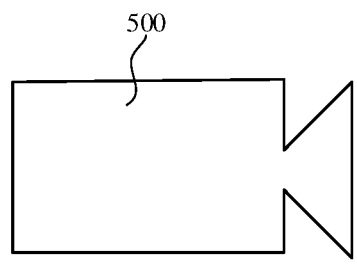
FIG. 4 is a schematic structural diagram of an electronic apparatus according to another embodiment of the present disclosure.

According to another embodiment, as shown in FIG. 4, the electronic apparatus provided by the present disclosure is a second electronic apparatus 500. The electronic apparatus comprises the photoelectric conversion device described above. The second electronic apparatus 500 may be a solar power generation device, a light detector, a fingerprint recognition device, an optical module, a CCD camera, or other types of electronic apparatus. Since the electronic apparatus comprises the above-mentioned photoelectric conversion device, it brings the same beneficial effects, which are not repeated herein in the present disclosure.

The present disclosure is further described below by way of embodiments, which, however, do not limit the present disclosure in any way. Compounds for which a synthesis method is not mentioned are raw material products obtained commercially.

1. Synthesis of Intermediates IM I-Y

Intermediates IM I-A, IM I-B, and IM I-C (hereinafter collectively referred to as IM I-Y) were synthesized following synthesis routes below.

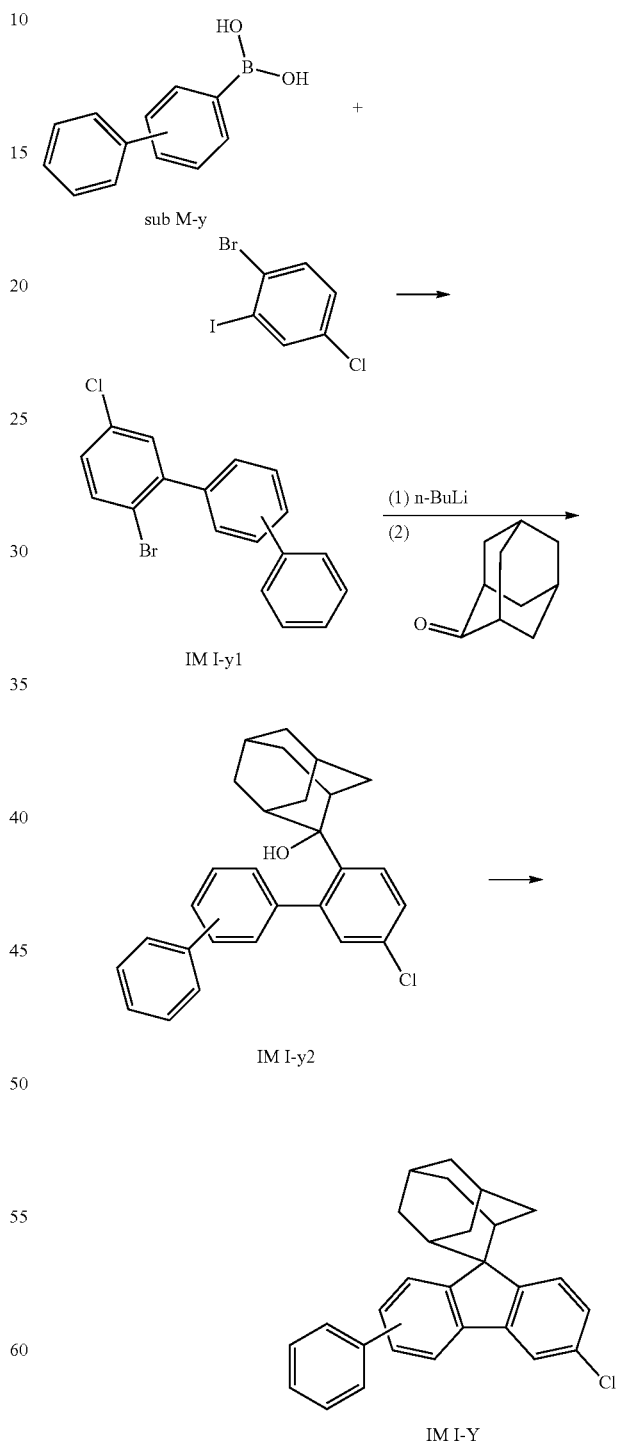

IM I-A was taken as an example to illustrate the synthesis of each IM I-Y.

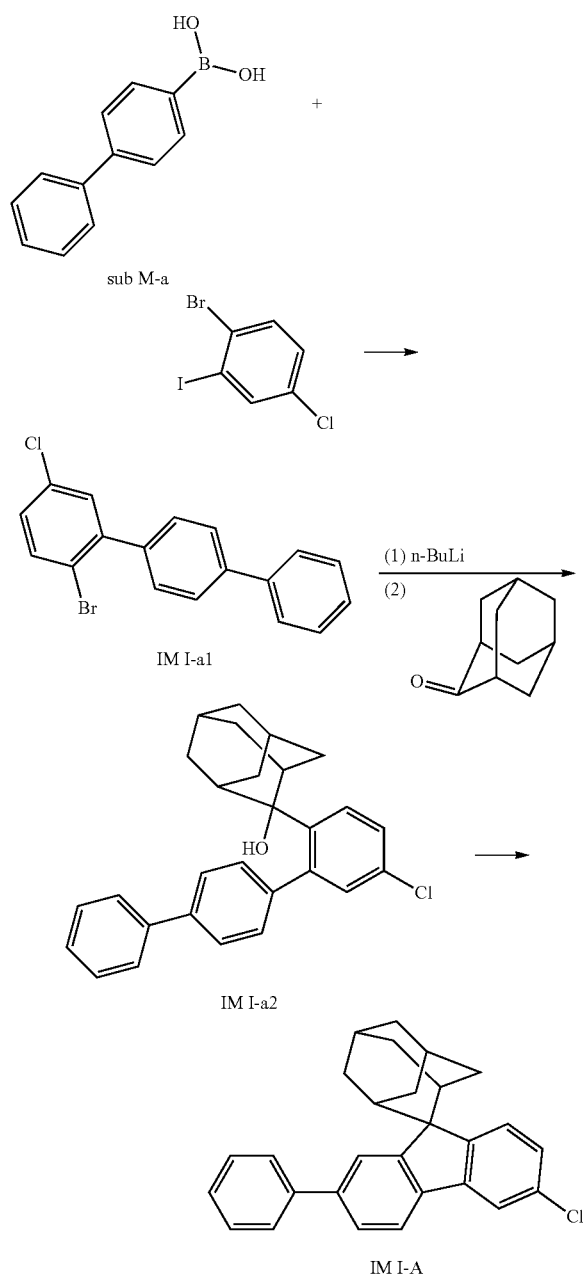

Sub M-a (80.0 g, 404.0 mmol), 1-bromo-4-chloro-2-iodobenzene (128.2 g, 404.0 mmol), tetrakis(triphenylphosphine)palladium (9.3 g, 8.08 mmol), potassium carbonate (122.8 g, 888.7 mmol), tetrabutylammonium chloride (26.1 g, 80.8 mmol), toluene (640 mL), ethanol (320 mL), and deionized water (200 mL) were added to a three-necked flask, heated to 78° C. under nitrogen protection, and stirred for 8 hours. The reaction solution was cooled to room temperature, and extracted after addition of toluene (400 mL). The resulting organic phases were combined, dried over anhydrous magnesium sulfate, and filtered. The resulting filtrate was concentrated under reduced pressure, obtaining a crude product. The crude product was purified by silica gel column chromatography using n-heptane as a mobile phase, and then purified by recrystallization using a mixture of dichloromethane and petroleum ether (1:3, v/v) system, yielding IM I-a1 (113.8 g, yield 82%).

IM I-a1 (110.0 g, 320.09 mmol) was added to a three-necked flask containing THF (1100 mL), followed by dropwise adding a n-butyl lithium solution in n-hexane (154 mL, 385.00 mmol) at −80° C. After the dropwise addition, the resulting mixture was kept at −80° C. for 1 hour, followed by dropwise adding adamantanone (57.7 g, 384.11 mmol), keeping still at −80° C. for 1 hour, and then heating to room temperature and stirring overnight. Hydrochloric acid was added to adjust the pH of the resulting solution to neutral. The solution was filtered, obtaining a white crude product. The crude product was beaten with petroleum ether, yielding a white solid, which is IM I-a2 (94.3 g, yield 71%).

IM I-a2 (96.2 g, 231.80 mmol), trifluoroacetic acid (79.3 g, 695.31 mmol), and dichloromethane (900 mL) were added to a three-necked flask, and stirred for 2 hours under nitrogen protection. An aqueous solution of sodium hydroxide was added to make the reaction solution neutral. The neutral reaction solution was separated. The resulting organic phase was dried over anhydrous magnesium sulfate and filtered, followed by removal of the solvent under reduced pressure. The resulting crude product was purified by silica gel column chromatography using a mixture of dichloromethane and n-heptane (1:2, v/v), yielding a white solid, which is IM I-A (73.7 g, yield 80%).

Intermediates IM I-Y listed in Table 1 were prepared by the same method for preparing Intermediate IM I-A, except that sub M-a was replaced with sub M-y. The raw materials sub M-y used, structures of synthesized Intermediates IM I-y1, IM I-y2, IM I-Y as well as final yields thereof are shown in Table 1.

TABLE 1

| sub M-y | IM I-y1 | IM I-y2 | IM I-Y | Yield/% |
|---|---|---|---|---|
|  |  |  |  | 73.0 |

TABLE 1-continued
| sub M-y | IM I-y1 | IM I-y2 | IM I-Y | Yield/% |
|---|---|---|---|---|
| 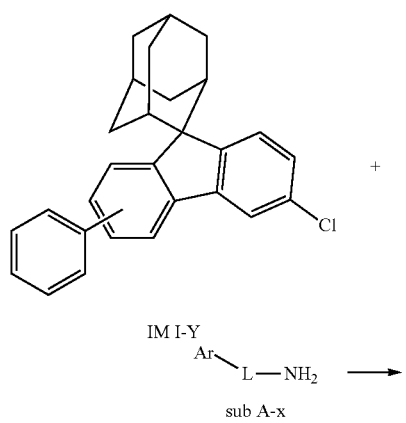 | | | IM I-C | 76.2 |
2. Compound Synthesis
Organic compounds of the present disclosure were synthesized following the synthesis routes below.
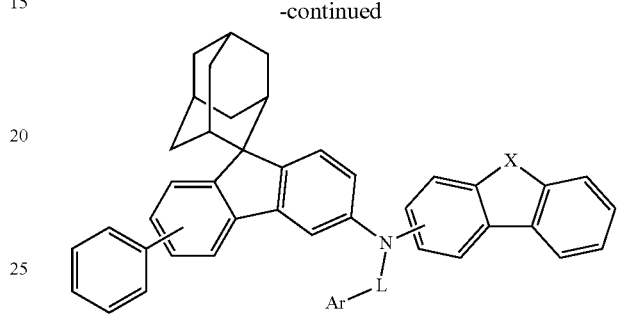
Synthesis Example 1: Synthesis of Compound 2
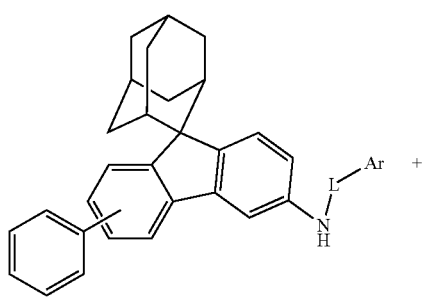
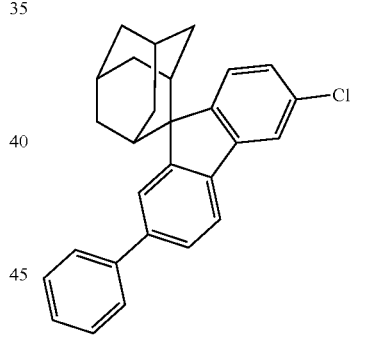
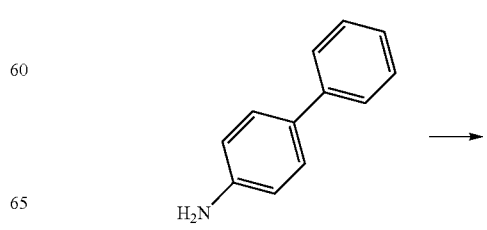

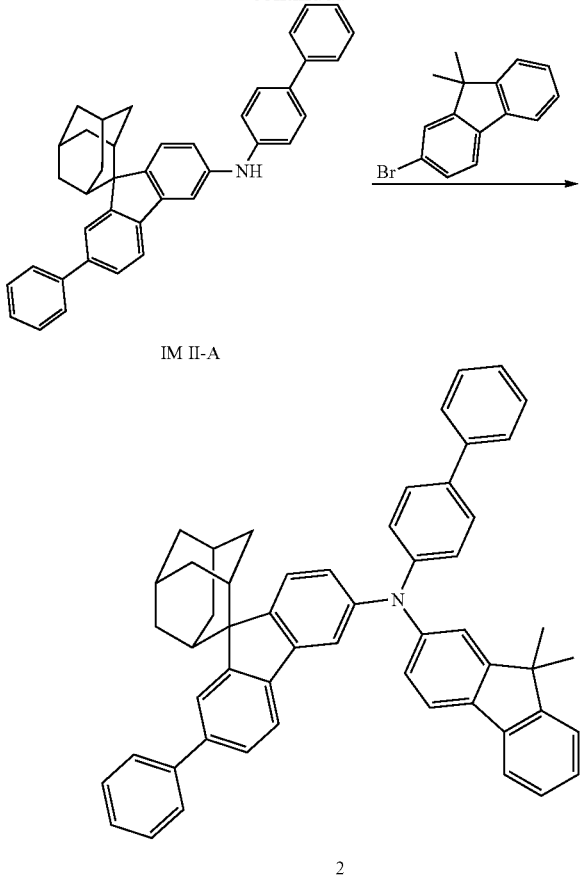

IM II-A

2

IM I-A (10.0 g, 25.19 mmol), [1,1'-biphenyl]-4-amine (4.48 g, 26.45 mmol), and toluene (100 mL) were added to a 250-mL three-necked flask under nitrogen protection, stirred and heated to 110° C. After the raw materials were dissolved and the resulting solution became clear, the solution was cooled to 70° C., followed by sequentially adding $Pd_2(dba)_3$ (0.46 g, 0.50 mmol), X-Phos (0.48 g, 1.24 mmol), and sodium tert-butoxide (3.63 g, 37.79 mmol), and heating and refluxing for 2 hours. The solution was then cooled to room temperature, washed with water to neutral, dried to remove water by adding 10 g of anhydrous magnesium sulfate, left to stand for 30 minutes, filtered and concentrated, obtaining a crude product. The crude product was purified by silica gel column chromatography, yielding Intermediate IM II-A (10.5 g, yield 79%).

IM II-A (10.0 g, 18.88 mmol), 2-bromo-9,9-dimethylfluorene (5.4 g, 19.82 mmol), and toluene (100 mL) were added to a 250-mL three-necked flask under nitrogen protection, and heated to 110° C. After the raw materials were dissolved and the resulting solution became clear, the solution was cooled to 70° C., followed by sequentially adding $Pd_2(dba)_3$ (0.35 g, 0.38 mmol), S-Phos (0.31 g, 0.76 mmol), and sodium tert-butoxide (2.72 g, 28.32 mmol), heating and refluxing for 4 hours. The solution was then cooled to room temperature, washed with water three times to neutral, dried to remove water by adding 10 g of anhydrous magnesium sulfate, left to stand for 30 minutes, filtered and then distilled under reduced pressure to remove the solvent, obtaining a crude product. The crude product was purified by recrystallization using a mixture of toluene and n-heptane (1:2, v/v), yielding Compound 2 (7.36 g, yield 54%). Mass spectrometry: m/z=722.4[M+H]$^+$.

Synthesis Examples 2 to 20

Compounds listed in Table 2 were prepared by the same method for preparing Compound 2, except that IM I-A was replaced with IM I-Y, that [1,1'-biphenyl]-4-amine was replaced with sub A-X, and that 2-bromo-9,9-dimethylfluorene was replaced with sub B-X. The compounds synthesized, final yields thereof, and mass spectrometry (MS) characterization results thereof are shown in Table 2.

TABLE 2
| Synthesis Example | IM I-Y | sub A-X | sub B-X | Compound | Yield/ % | MS, [M + H]+ |
|---|---|---|---|---|---|---|
| 2 | IM A-1 | | | 5 | 43.9 | 722.4 |
| 3 | IM I-A | | | 19 | 44.7 | 696.3 |
| 4 | IM I-A | | | 25 | 51.3 | 696.3 |
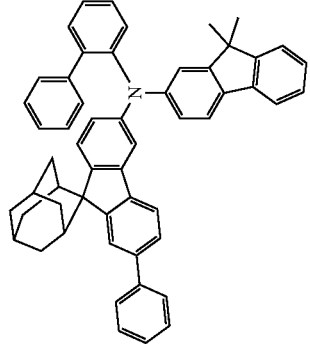

TABLE 2-continued

| Synthesis Example | IM1-Y | sub A-X | sub B-X | Compound | Yield/% | MS, [M + H]+ |
|---|---|---|---|---|---|---|
| 5 | IM1-B | | | 36 | 50.3 | 696.4 |
| 6 | IM1-B | | | 39 | 39.6 | 798.4 |
| 7 | IM1-B | | | 55 | 45.8 | 772.4 |

TABLE 2-continued
| Synthesis Example | IM 1-Y | sub A-X | sub B-X | Compound | Yield/% | MS, [M + H]+ |
|---|---|---|---|---|---|---|
| 8 | 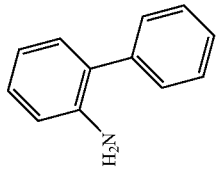 IM1-C | 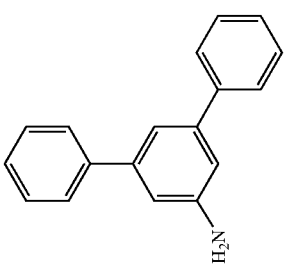 | 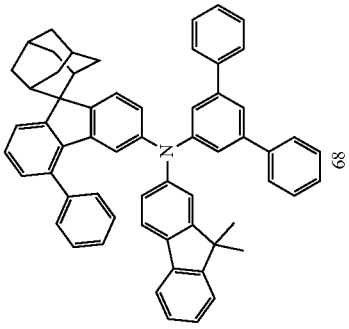 | 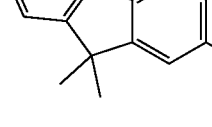 63 | 33.8 | 722.4 |
| 9 | 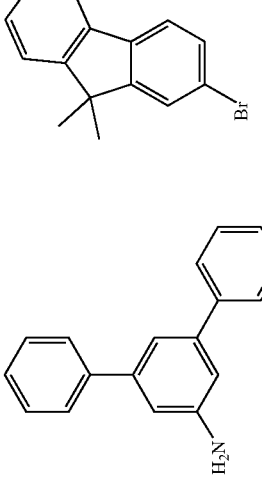 IM1-C | 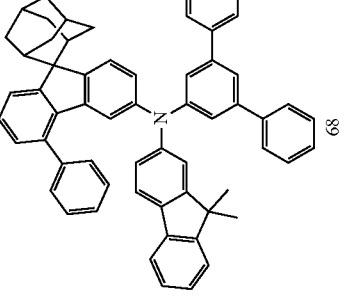 | 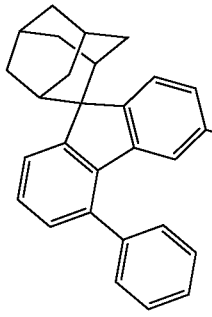 | 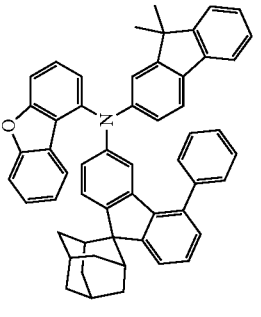 68 | 39.0 | 798.4 |
| 10 | IM1-C | | | 71 | 41.6 | 736.3 |

TABLE 2-continued

| Synthesis Example | IM I-Y | sub A-X | sub B-X | Compound | Yield/% | MS, [M + H]+ |
|---|---|---|---|---|---|---|
| 11 | IM I-C | biphenyl-3-amine | 3-bromodibenzofuran | 77 | 45.0 | 696.3 |
| 12 | IM I-C | 2-(naphthalen-2-yl)aniline | 2-bromo-9,9-dimethylfluorene | 82 | 46.2 | 772.4 |
| 13 | IM I-B | naphthalen-1-amine | 3-bromodibenzothiophene | 91 | 38.8 | 686.3 |

TABLE 2-continued

| Synthesis Example | IM I-Y | sub A-X | sub B-X | Compound | Yield/% | MS, [M + H]+ |
|---|---|---|---|---|---|---|
| 14 | IM I-Y | | | 96 | 41.8 | 772.4 |
| 15 | IM I-C | | | 98 | 46.0 | 798.4 |
| 16 | IM I-B | | | 102 | 39.5 | 772.4 |

TABLE 2-continued

| Synthesis Example | IM I-Y | sub A-X | sub B-X | Compound | Yield/% | MS, [M + H]+ |
|---|---|---|---|---|---|---|
| 17 | IM I-B | | | 109 | 40.5 | 702.4 |
| 18 | IM I-A | | | 110 | 42.8 | 811.4 |
| 19 | IM I-A | | | 111 | 49.1 | 775.4 |

TABLE 2-continued
| Synthesis Example | IM I-Y | sub A-X | sub B-X | Compound | Yield/% | MS, [M + H]+ |
|---|---|---|---|---|---|---|
| 20 | 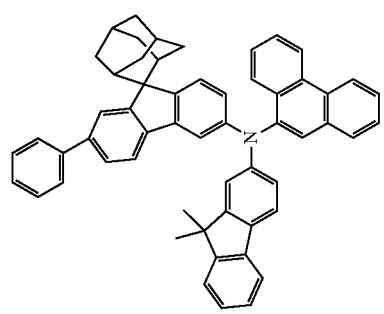 IM A-1 | 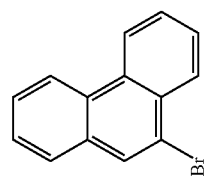 | 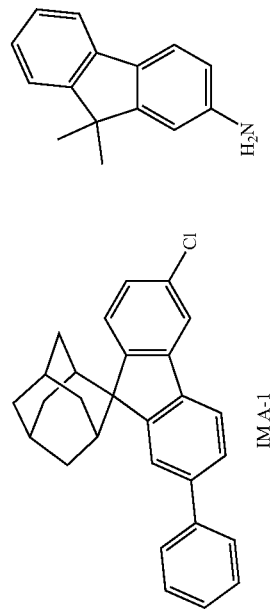 | 112 | 44.5 | 746.4 |

NMR data of some of the compounds are shown in Table 3.

TABLE 3

| Com-pound | $^1$H-NMR(400 MHz, CD$_2$Cl$_2$) δ: ppm |
|---|---|
| 2 | 8.32 (s, 1H), 8.02 (d, 1H), 7.69-7.60 (m, 8H), 7.58-7.50 (m, 3H), 7.49-7.39 (m, 5H), 7.40-7.24 (m, 7H), 7.14 (d, 1H), 7.07 (d, 1H), 3.02 (d, 2H), 2.94 (d, 2H), 2.21 (d, 2H), 2.01 (s, 2H), 1.85 (t, 4H), 1.68 (s, 2H), 1.44 (s, 6H). |
| 5 | 8.27 (s, 1H), 7.86 (d, 1H), 7.69-7.64 (m, 2H), 7.60-7.54 (m, 2H), 7.53-7.31 (m, 11H), 7.31-7.17 (m, 4H), 7.03-6.94 (m, 4H), 6.88 (d, 1H), 6.80 (d, 1H), 2.98 (d, 2H), 2.87 (d, 2H), 2.21 (d, 2H), 2.01 (s, 2H), 1.87 (t, 4H), 1.63 (s, 2H), 1.30 (s, 6H). |
| 63 | 8.15 (d, 1H), 7.80 (d, 1H), 7.54 (d, 1H), 7.36-7.22 (m, 7H), 7.20-7.17 (m, 1H), 7.16-7.05 (m, 4H), 7.02-6.93 (m, 7H), 6.88 (m, 1H), 6.80 (d, 1H), 6.65 (s, 1H), 6.55 (d, 1H), 6.35 (s, 1H), 2.99 (d, 2H), 2.88 (d, 2H), 2.18 (d, 2H), 2.00 (s, 2H), 1.80 (t, 4H), 1.60 (s, 2H), 1.24 (s, 6H). |

Organic electroluminescent devices were fabricated using the following methods.

Example 1: Organic Electroluminescent Device

An anode was prepared by the following processes. An ITO substrate, with thicknesses of ITO/Ag/ITO being 100 Å, 1000 Å, and 100 Å, respectively, was cut to have dimensions of 40 mm (length)×40 mm (width)×0.7 mm (thickness), and then fabricated, by photoetching process, into an experimental substrate with patterns of a cathode, of an anode, and of an insulation layer, followed by treatment of its surface using ultraviolet ozone and O$_2$:N$_2$ plasma to increase the work function of the anode. The surface of the ITO substrate was then cleaned with an organic solvent to remove impurities and oil thereon.

HAT-CN was deposited by vacuum evaporation on the experimental substrate (anode) to form a hole injection layer (HIL) with a thickness of 100 Å, and then Compound NPB was deposited by vacuum evaporation on the hole injection layer to form a first hole transport layer (HTL1) with a thickness of 1050 Å.

Compound 2 was deposited by vacuum evaporation on the first hole transport layer to form a second hole transport layer (HTL2) with a thickness of 850 Å.

RH-1 and Ir(piq)$_2$(acac) were co-deposited by evaporation on the second hole transport layer at a weight ratio of 98%:2% to form an organic emissive layer (EML) with a thickness of 400 Å.

TPBi and LiQ were mixed at a weight ratio of 1:1 and deposited by evaporation on the organic emissive layer to form an electron transport layer (ETL) with a thickness of 350 Å; metal Yb was deposited by evaporation on the electron transport layer to form an electron injection layer (EIL) with a thickness of 15 Å; and then magnesium (Mg) and silver (Ag) were mixed at an evaporation rate ratio of 1:9 and deposited by vacuum evaporation on the electron injection layer to form a cathode with a thickness of 105 Å.

Furthermore, CP-1 was deposited by vacuum evaporation on the above cathode to form an organic capping layer (CPL) with a thickness of 730 Å, thereby completing the fabrication of an organic electroluminescent device.

Examples 2 to 20

Organic electroluminescent devices were fabricated by the same method as used in Example 1, except that Compound 2 in Example 1 was replaced with a compound shown in Table 4 below when a second hole transport layer was formed.

Comparative Examples 1 to 4

Organic electroluminescent devices were fabricated by the same method as used in Example 1, except that Compound 2 in Example 1 was replaced with a respective one of Compound A, Compound B, Compound C, and Compound D when a second hole transport layer was formed.

Structures of the materials used in the Comparative Examples and the Examples during the fabrication of the organic electroluminescent devices are as follows:

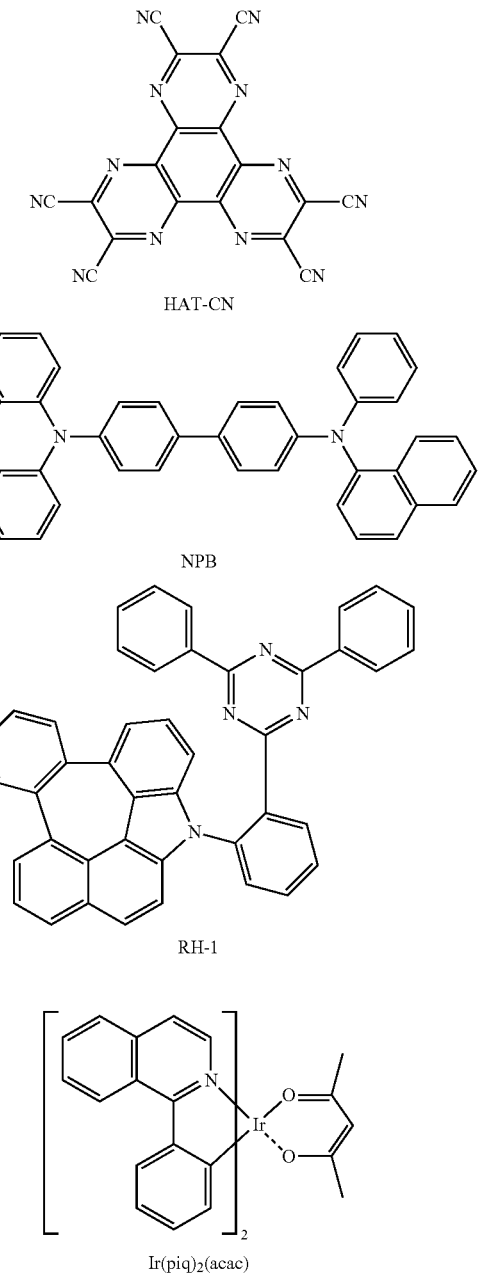

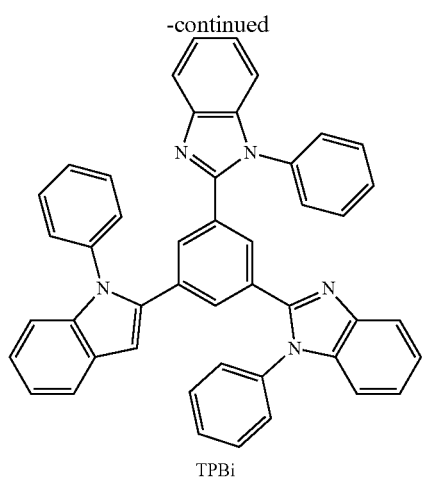
TPBi
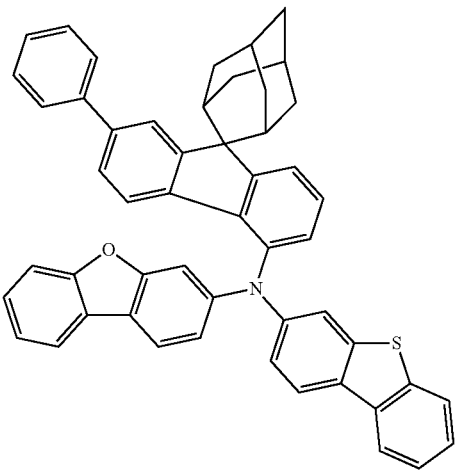
Compound B
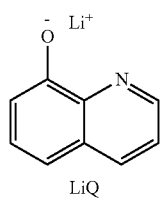
LiQ
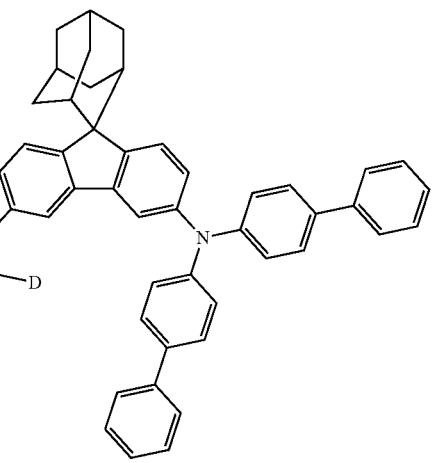
Compound C
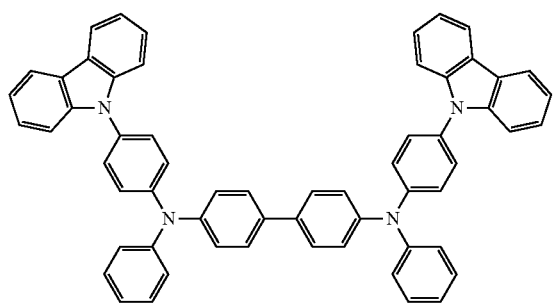
CP-1
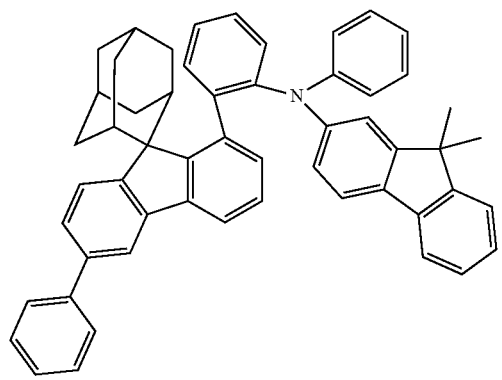
Compound A
Compound D
The organic electroluminescent devices fabricated in the Examples and Comparative Examples were tested for their performance. Specifically, the IVL characteristics of the devices were tested under the condition of 10 mA/cm², and the T95 lifetime of the devices was tested under the condition of 15 mA/cm². Test results are shown in Table 4 below.

TABLE 4

| No | HTL2 Material | Driving voltage (V) | Current Efficiency (Cd/A) | CIEy | CIEx | T95 (h) |
| --- | --- | --- | --- | --- | --- | --- |
| Example 1 | Compound 2 | 3.58 | 61.8 | 0.680 | 0.320 | 580 |
| Example 2 | Compound 5 | 3.56 | 62.1 | 0.680 | 0.320 | 578 |
| Example 3 | Compound 19 | 3.61 | 61.3 | 0.680 | 0.320 | 522 |
| Example 4 | Compound 25 | 3.59 | 58.7 | 0.680 | 0.320 | 527 |
| Example 5 | Compound 36 | 3.63 | 60.6 | 0.680 | 0.320 | 548 |
| Example 6 | Compound 39 | 3.61 | 58.4 | 0.680 | 0.320 | 553 |
| Example 7 | Compound 55 | 3.60 | 61.8 | 0.680 | 0.320 | 524 |
| Example 8 | Compound 63 | 3.62 | 59.0 | 0.680 | 0.320 | 551 |
| Example 9 | Compound 68 | 3.58 | 60.9 | 0.680 | 0.320 | 549 |
| Example 10 | Compound 71 | 3.64 | 61.5 | 0.680 | 0.320 | 530 |
| Example 11 | Compound 77 | 3.63 | 59.1 | 0.680 | 0.320 | 532 |
| Example 12 | Compound 82 | 3.61 | 59.6 | 0.680 | 0.320 | 547 |
| Example 13 | Compound 91 | 3.59 | 60.3 | 0.680 | 0.320 | 525 |
| Example 14 | Compound 96 | 3.62 | 60.4 | 0.680 | 0.320 | 529 |
| Example 15 | Compound 98 | 3.63 | 59.7 | 0.680 | 0.320 | 552 |
| Example 16 | Compound 102 | 3.57 | 60.7 | 0.680 | 0.320 | 548 |
| Example 17 | Compound 109 | 3.61 | 60.2 | 0.680 | 0.320 | 550 |
| Example 18 | Compound 110 | 3.63 | 59.1 | 0.680 | 0.320 | 525 |
| Example 19 | Compound 111 | 3.60 | 60.2 | 0.680 | 0.320 | 527 |
| Example 20 | Compound 112 | 3.65 | 59.8 | 0.680 | 0.320 | 549 |
| Comparative Example 1 | Compound A | 3.66 | 51.4 | 0.680 | 0.320 | 443 |
| Comparative Example 2 | Compound B | 3.69 | 51.9 | 0.680 | 0.320 | 450 |
| Comparative Example 3 | Compound C | 3.71 | 52.3 | 0.680 | 0.320 | 433 |
| Comparative Example 4 | Compound D | 3.79 | 50.5 | 0.680 | 0.320 | 420 |

As can be seen from Table 4 above, compared with the organic electroluminescent devices fabricated in Comparative Examples 1 to 4, the organic electroluminescent devices fabricated in Examples 1 to 20 exhibit significantly improved performance. Specifically, the luminescence efficiency of the organic electroluminescent devices fabricated in Examples 1 to 20 is increased by at least 11.7%, the T95 lifetime thereof is increased by at least 15.5%, and the driving voltage therefor is relatively low.

It should be noted finally that the above embodiments are intended only to illustrate, rather than limiting, the technical solutions of the present disclosure. Although the present disclosure is described in detail with reference to the foregoing embodiments, those of ordinary skill in the art should appreciate that modifications may still be made to the technical solutions disclosed in the foregoing embodiments, or equivalent replacement may be made to some of all of the technical features therein. These modifications or replacements do not cause the essence of corresponding technical solutions to depart from the scope of the technical solutions of the embodiments of the present disclosure.

The invention claimed is:
1. An organic compound, having a structure selected from Formula 1-1, 1-2, or 1-3:

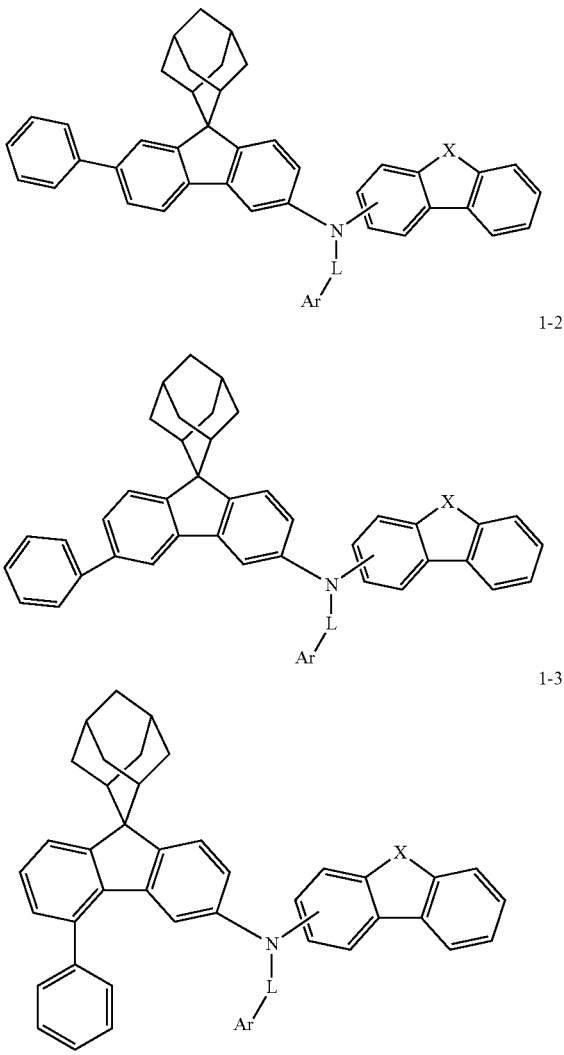

wherein X represents O, S, or C(R₁R₂), $R_1$ and $R_2$ are identical, and are selected from methyl or phenyl;
L is selected from a single bond, a substituted or unsubstituted phenylene, a substituted or unsubstituted naphthylene, or a substituted or unsubstituted biphenylene;
substituents of L are selected from phenyl or naphthyl;
Ar is selected from a substituted or unsubstituted phenyl, a substituted or unsubstituted naphthyl, a substituted or unsubstituted biphenyl, a substituted or unsubstituted terphenyl, a substituted or unsubstituted phenanthryl, a substituted or unsubstituted fluorenyl, a substituted or unsubstituted dibenzofuranyl, a substituted or unsubstituted dibenzothienyl, or a substituted or unsubstituted carbazolyl;
substituents in Ar are each independently selected from deuterium, fluorine, methyl, ethyl, isopropyl, tert-butyl, phenyl, naphthyl, or biphenyl; wherein when the number of substituents is greater than 1, the substituents are identical.

2. The organic compound according to claim 1, wherein Ar is selected from a substituted or unsubstituted group W, wherein the unsubstituted group W is selected from the group consisting of the following groups:

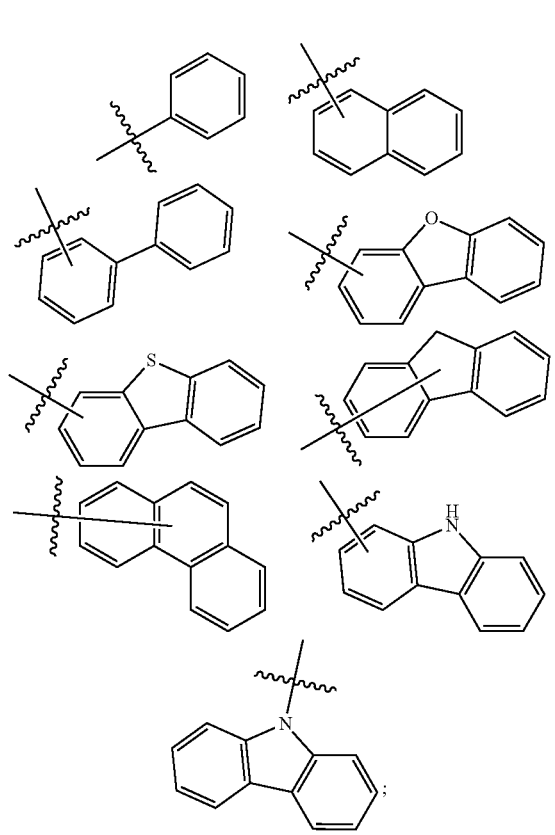

the substituted group W has one or more substituents, each substituent independently selected from deuterium, fluorine, methyl, ethyl, isopropyl, tert-butyl, phenyl, naphthyl, biphenyl, wherein when the number of the substituents is greater than 1, the substituents are identical.

3. The organic compound according to claim 1, wherein the organic compound is selected from the group consisting of the following compounds:

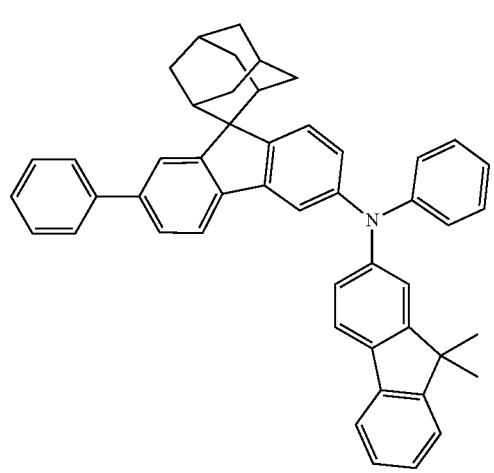

1

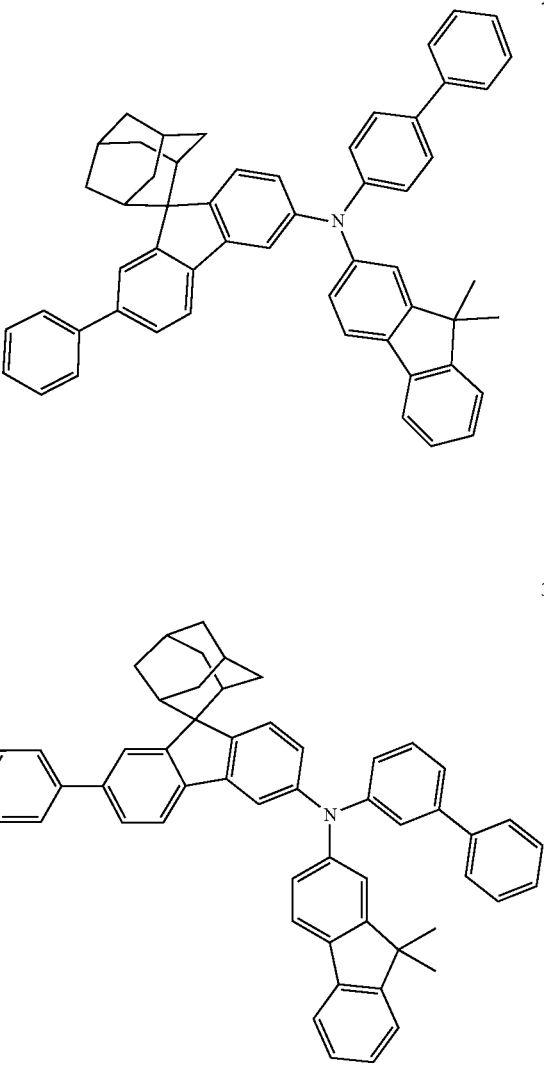

2

3

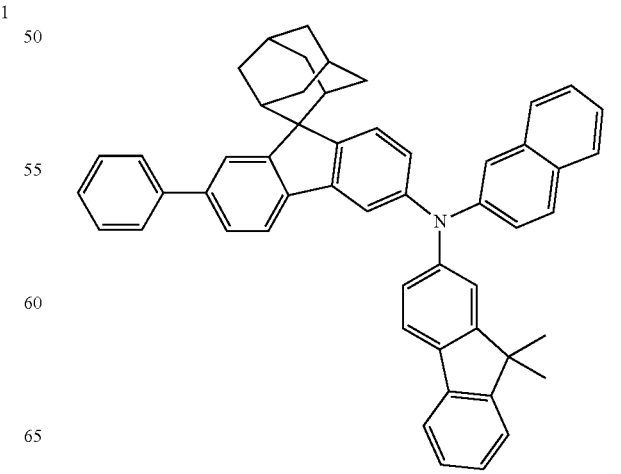

4

5
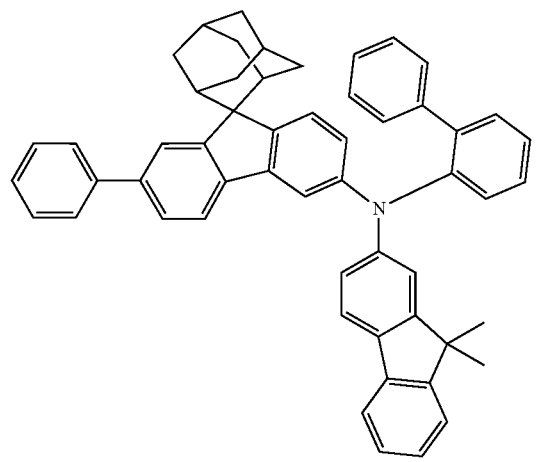
6
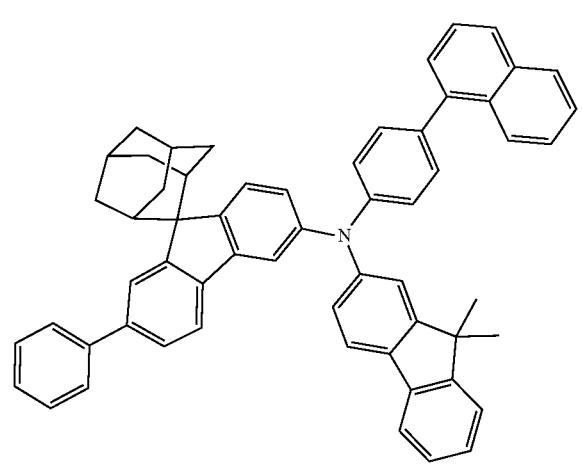
7
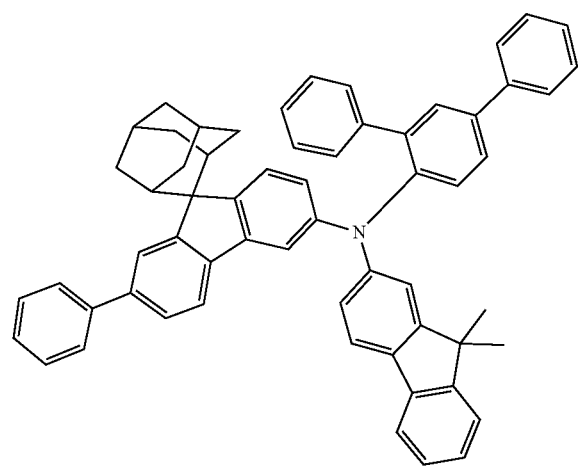
8
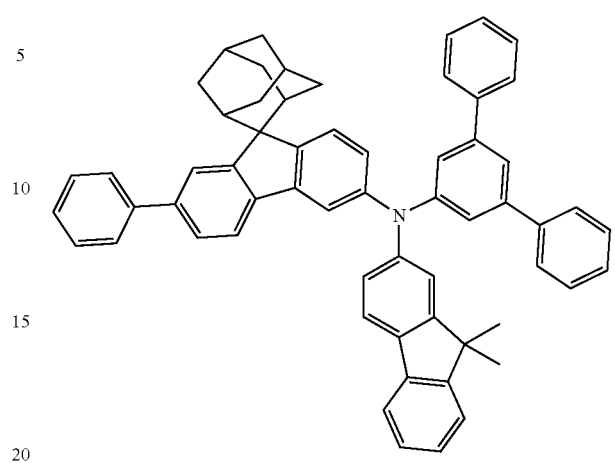
9
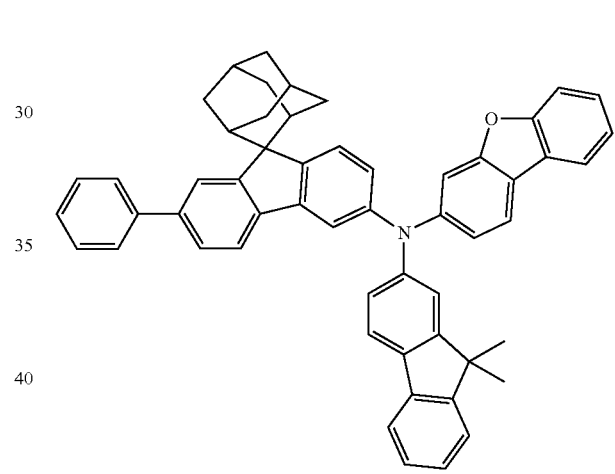
10
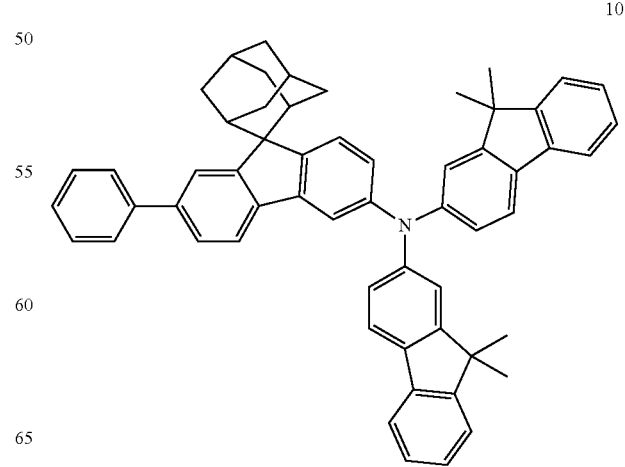

11
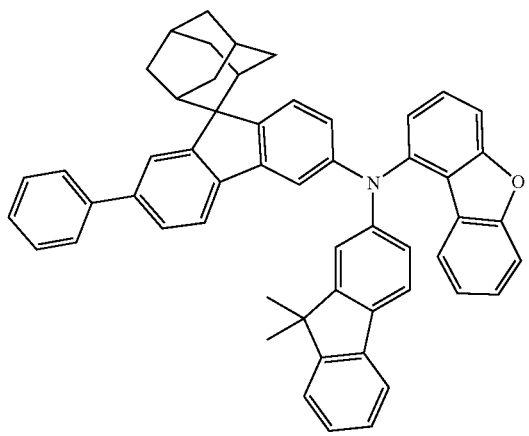
12
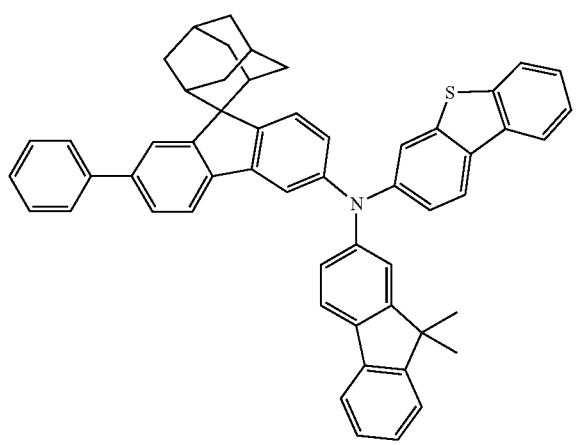
13
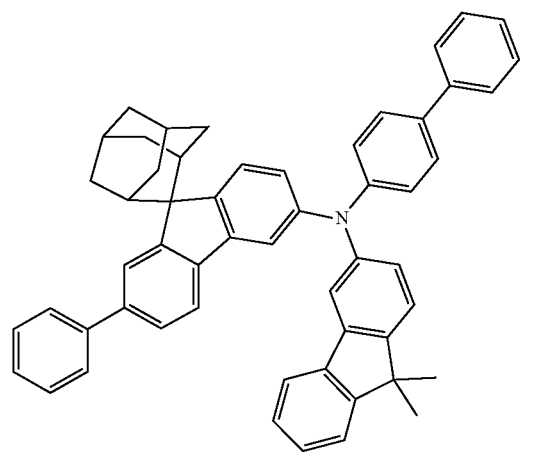
14
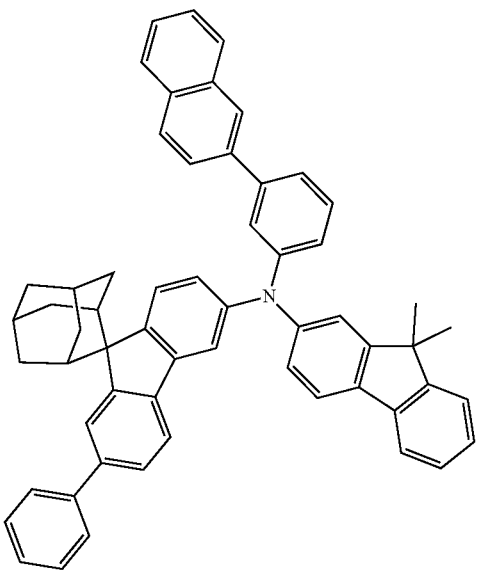
15
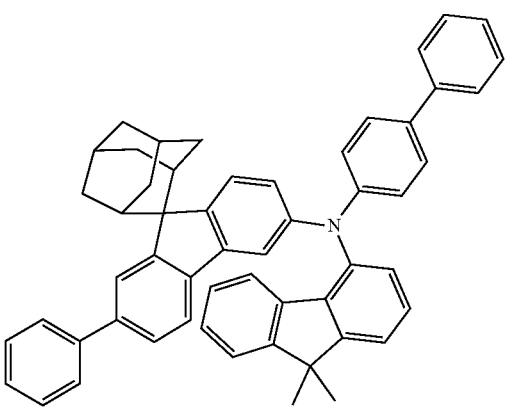
16
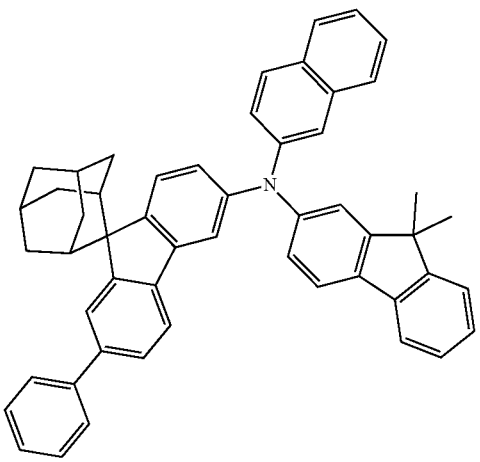

17
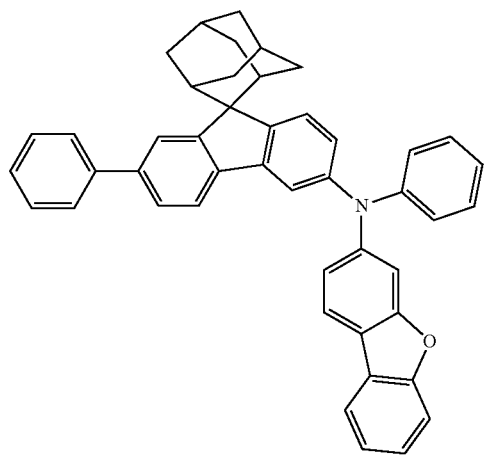
18
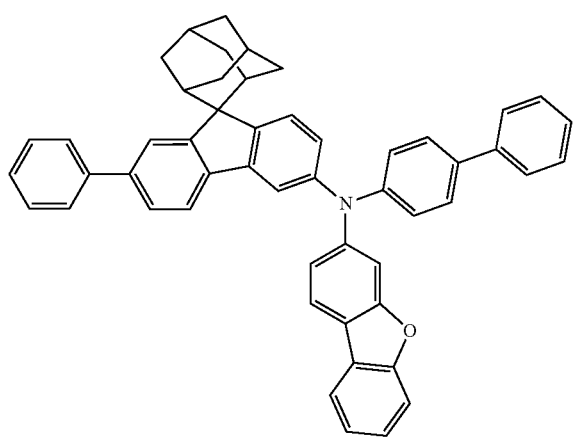
20
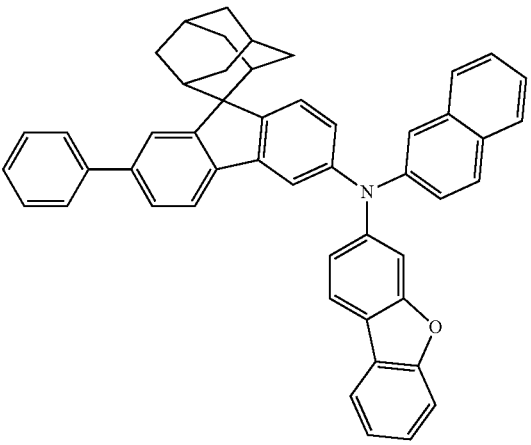
21
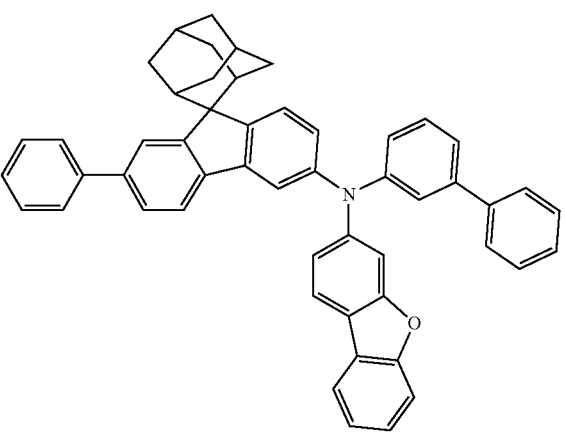
22
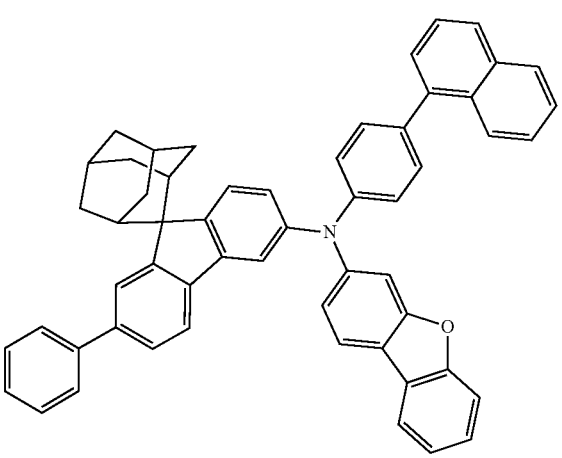
19
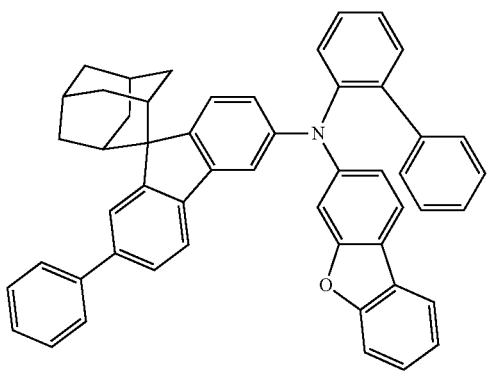

23
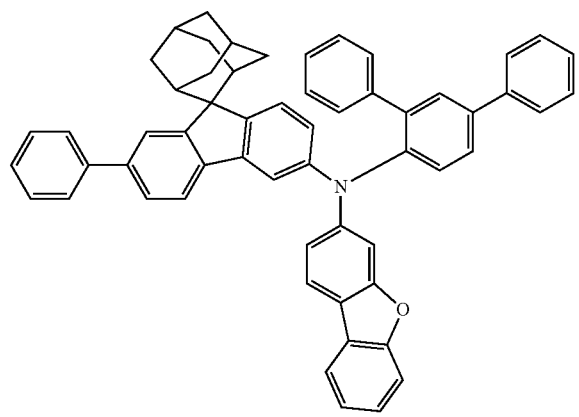
24
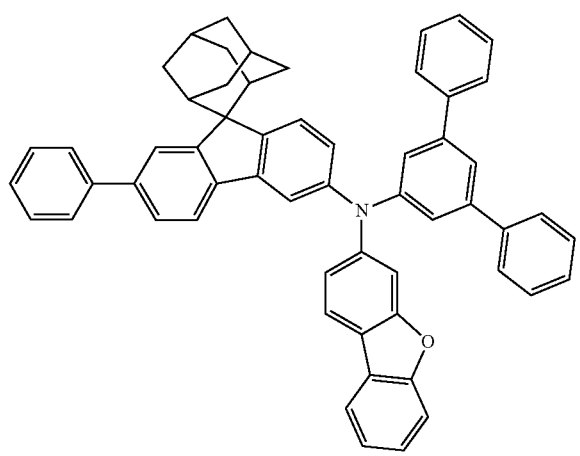
25
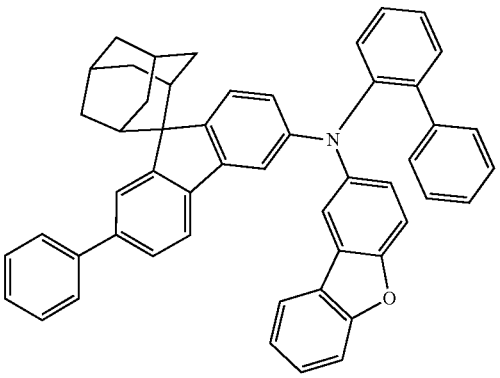
26
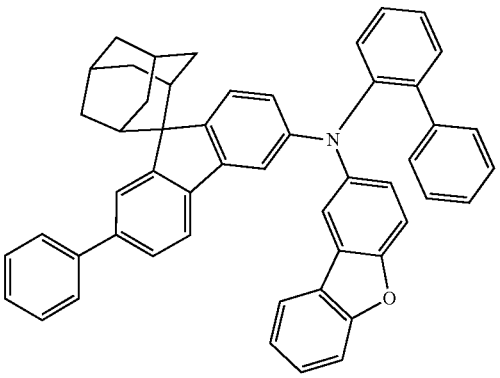
27
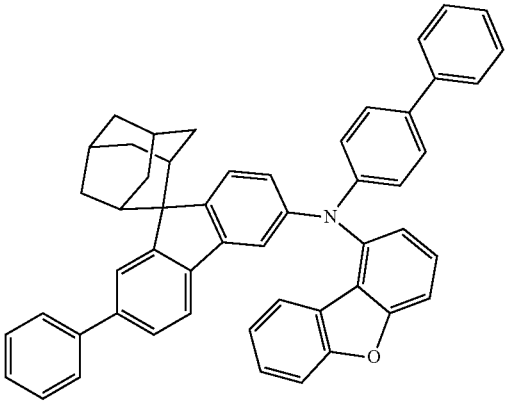
28
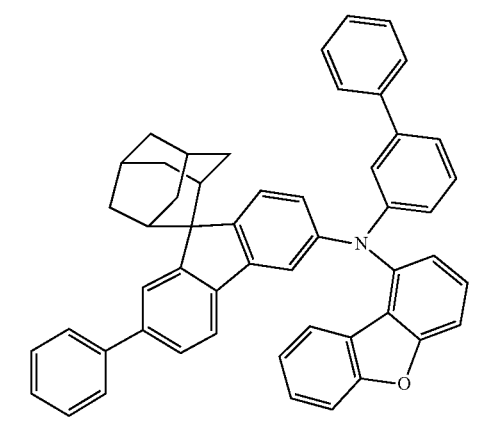
29
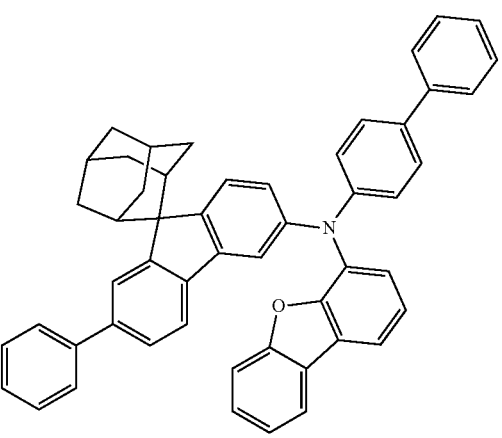

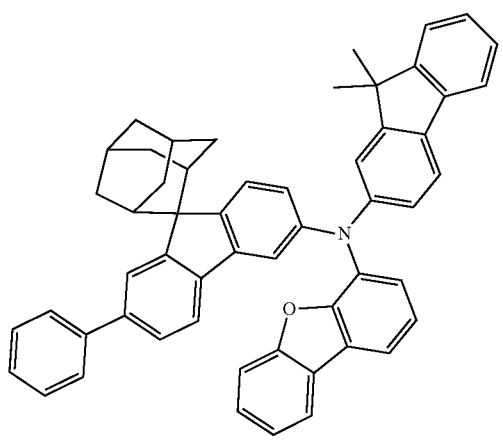
30
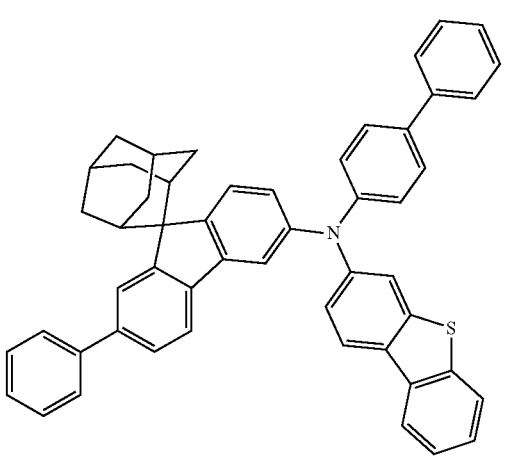
31
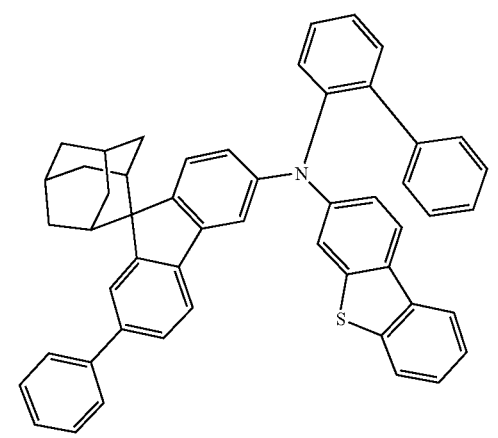
32
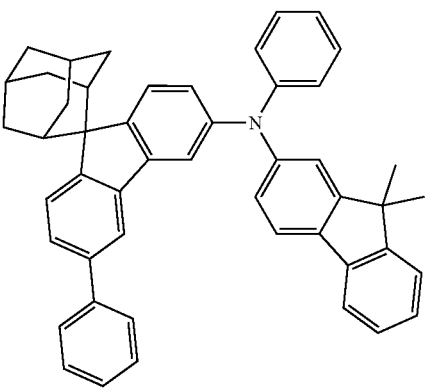
33
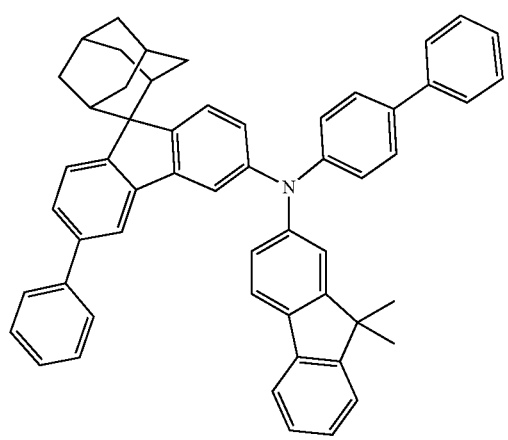
34
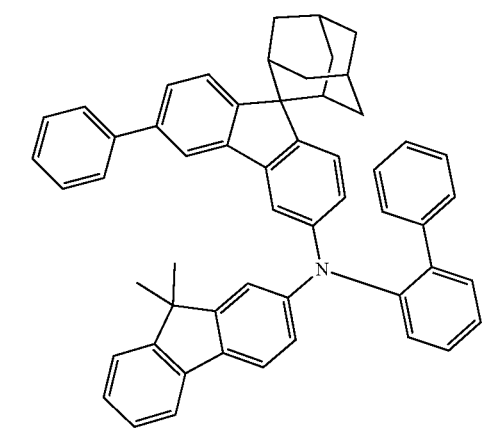
35
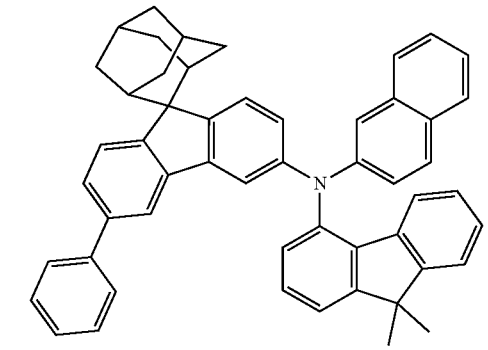
36

37
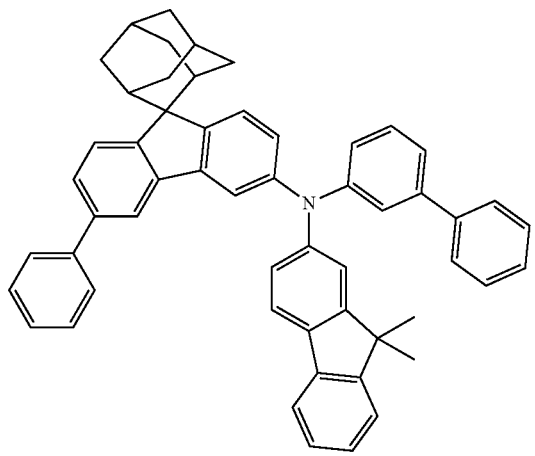
38
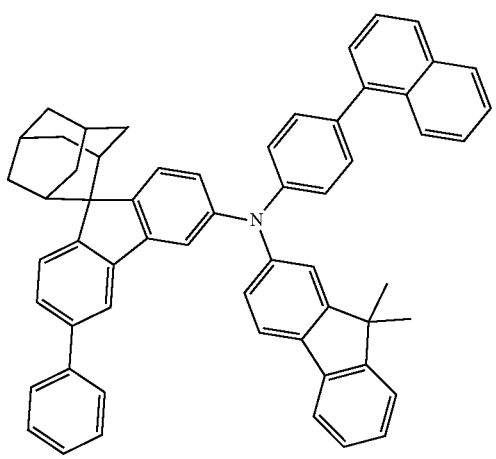
39
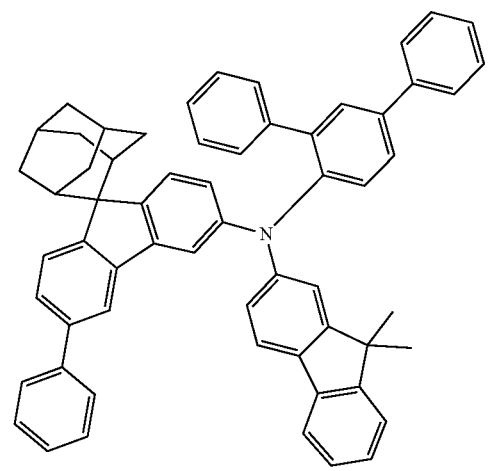
40
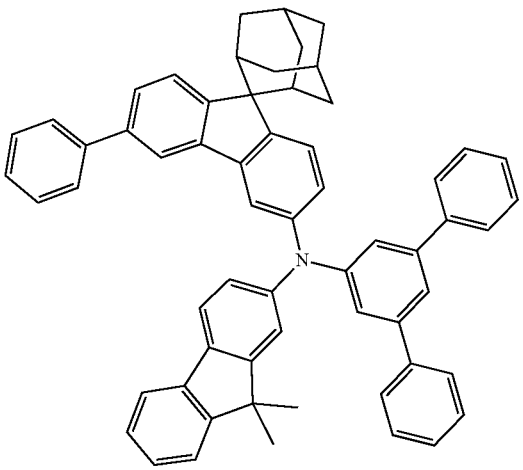
41
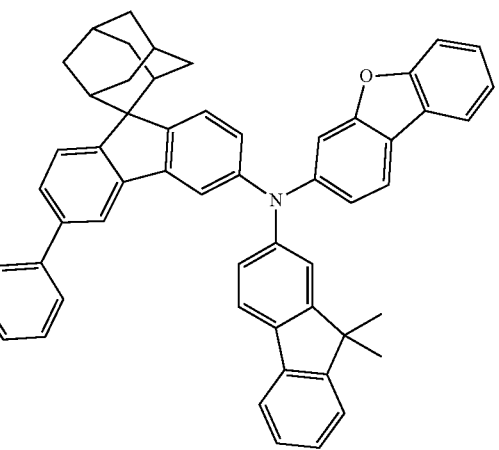
42
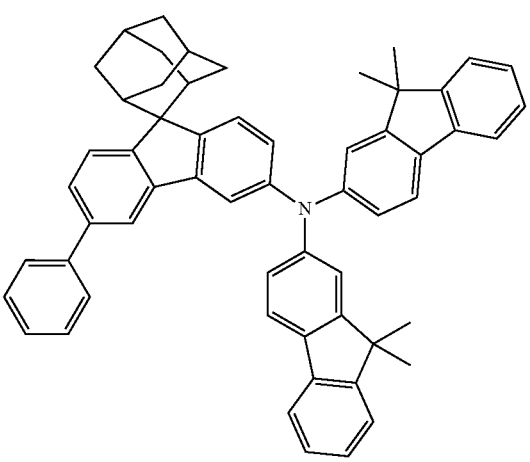

103
-continued
43
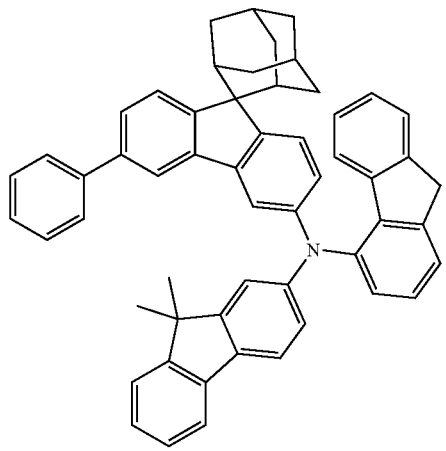
44
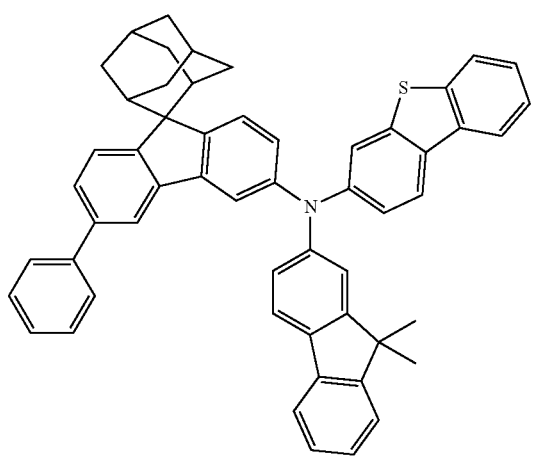
45
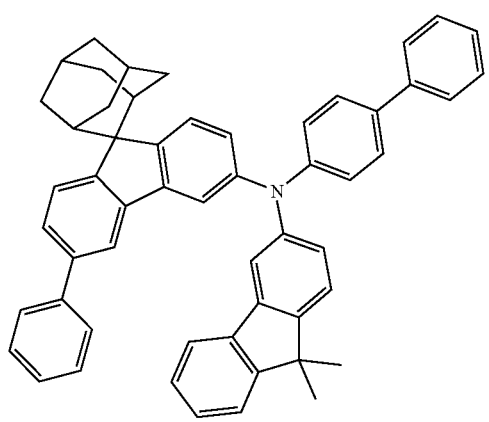
104
-continued
46
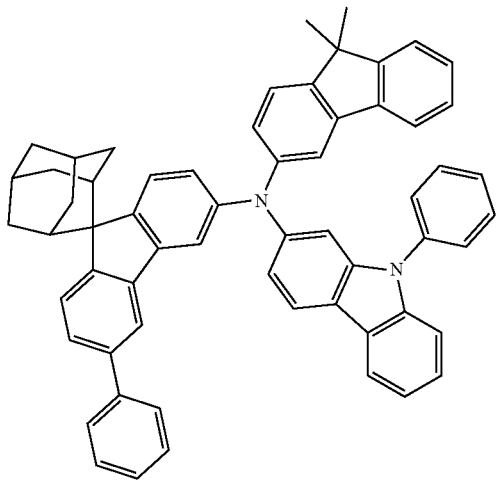
47
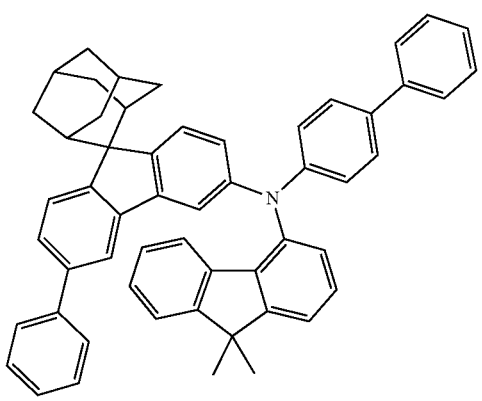
48
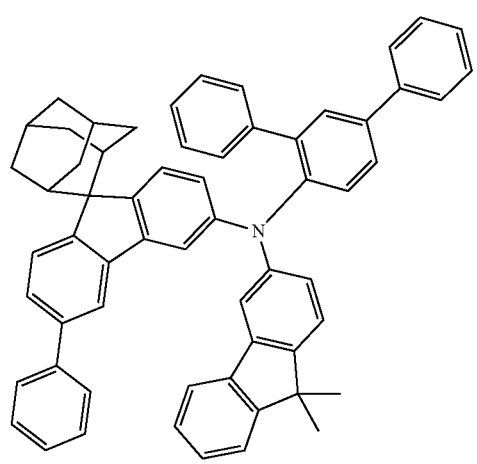

49
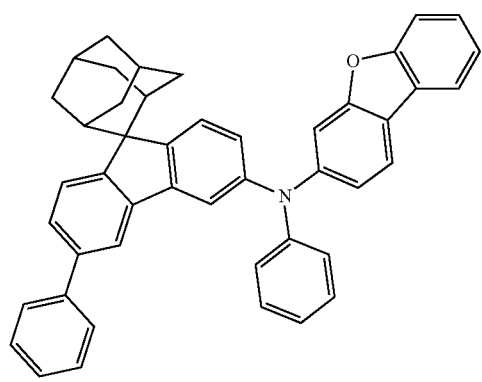
50
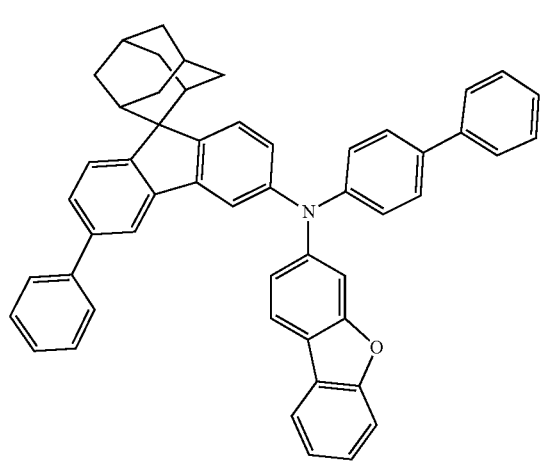
51
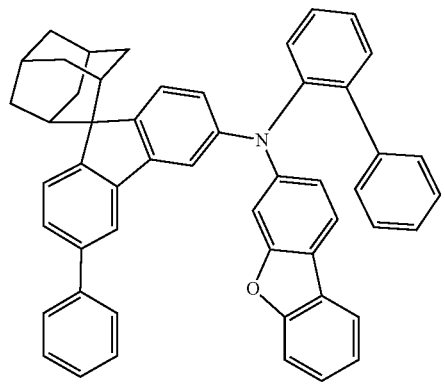
52
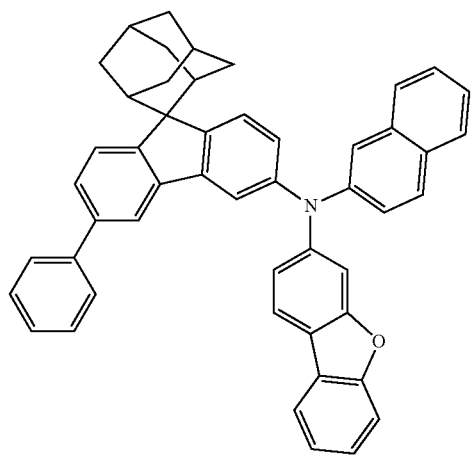
53
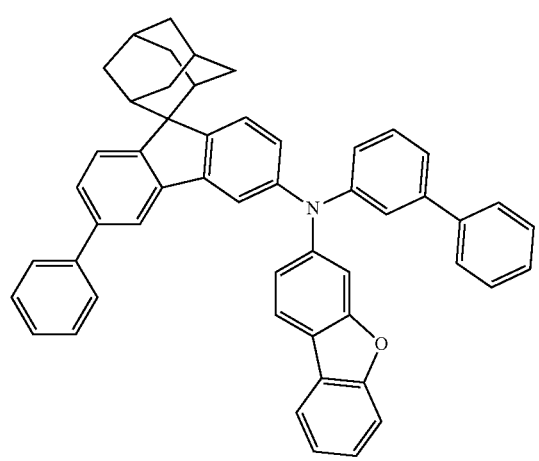
54
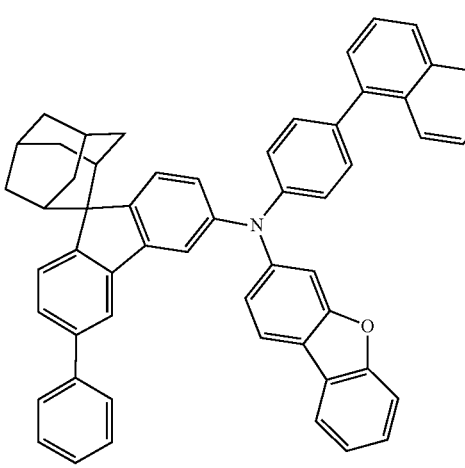

55
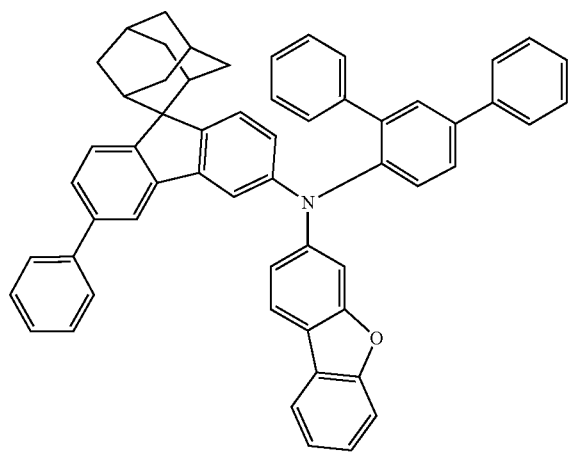
56
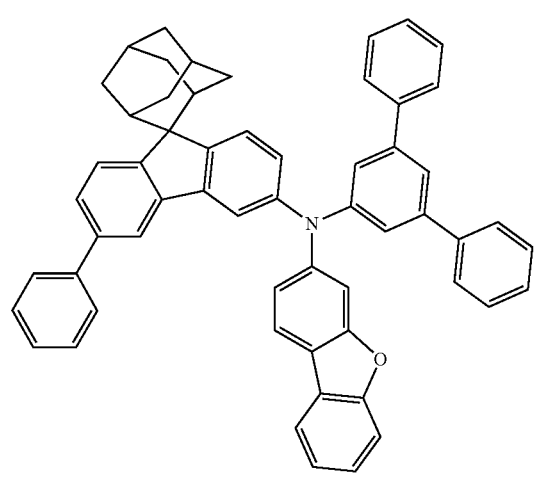
57
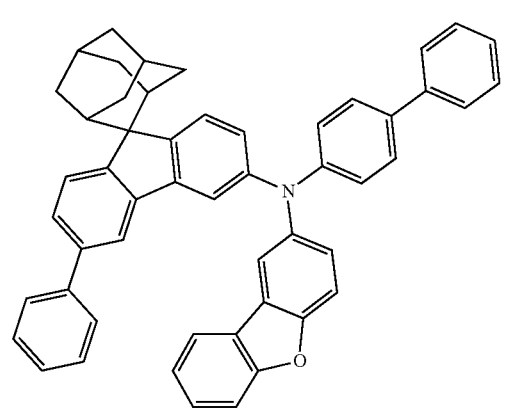
58
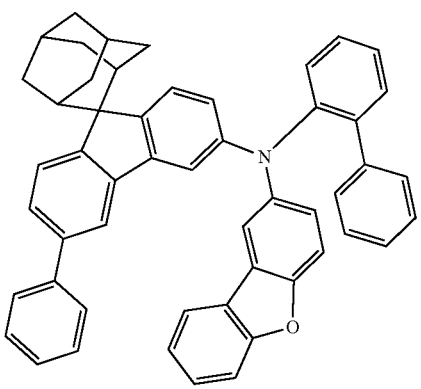
59
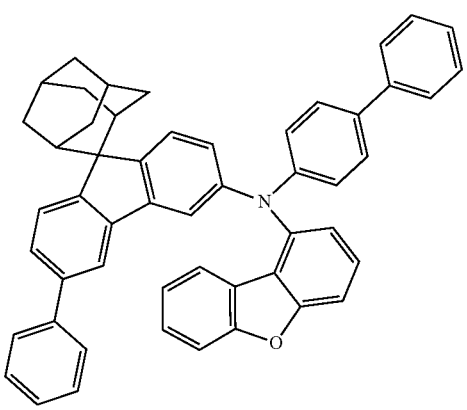
60
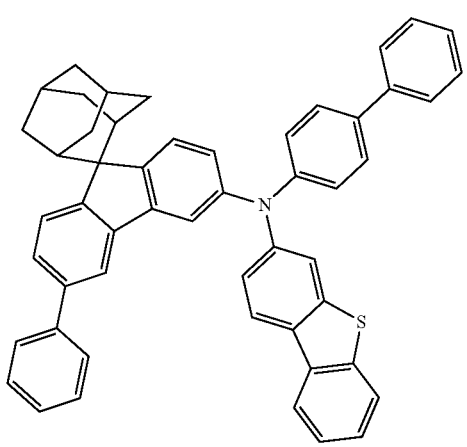
61
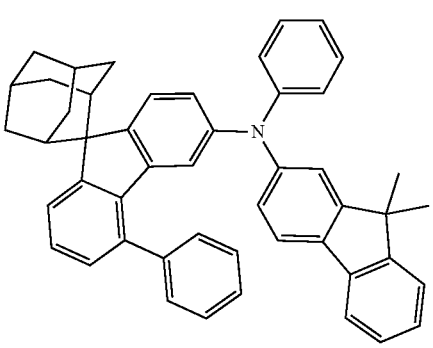

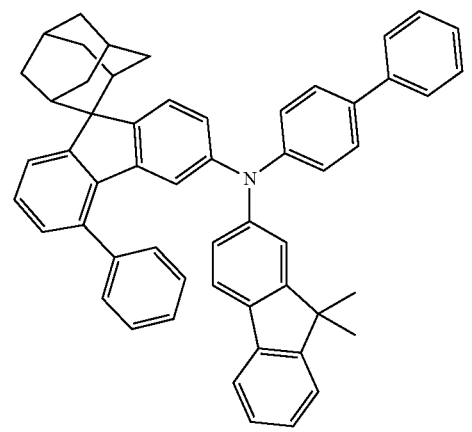
62
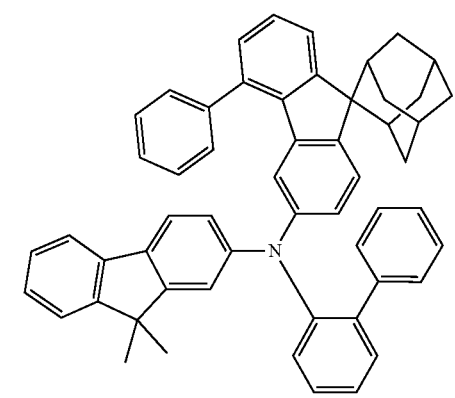
63
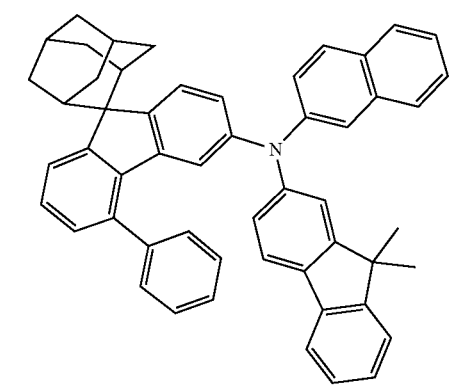
64
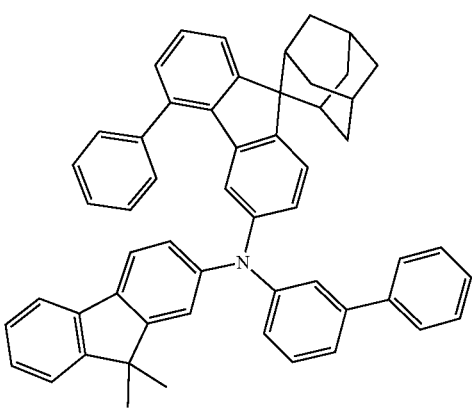
65
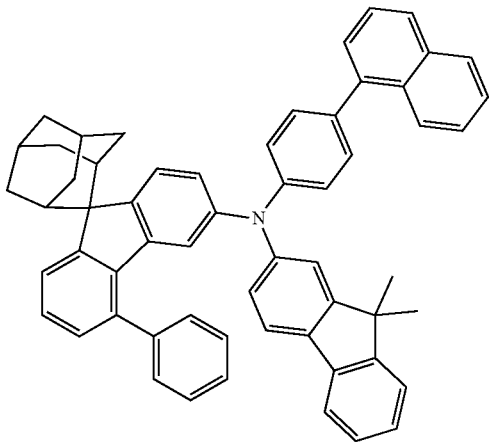
66
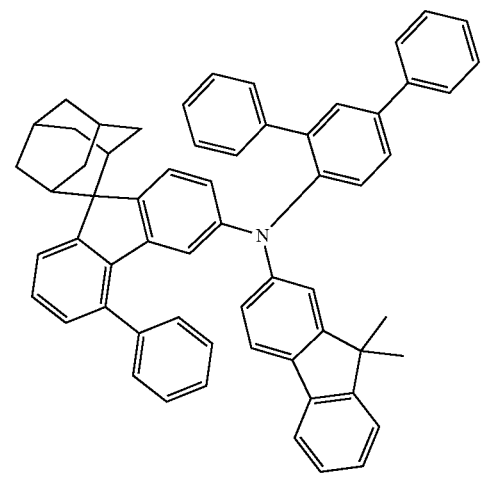
67
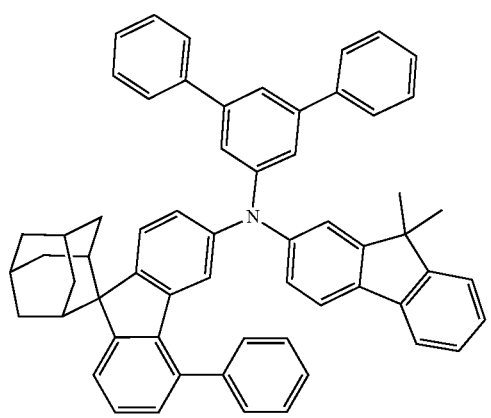
68

69
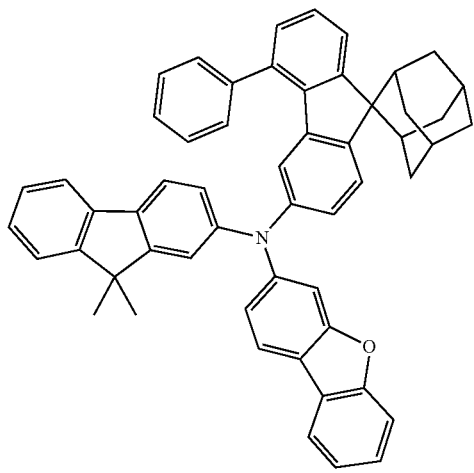
70
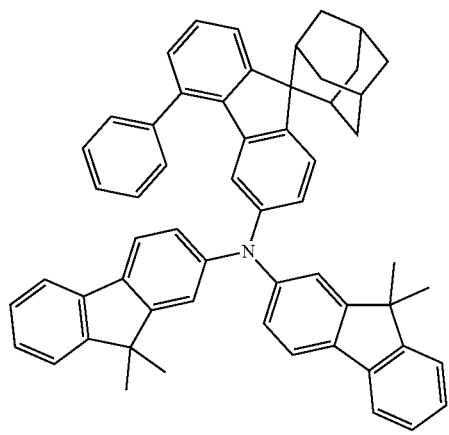
71
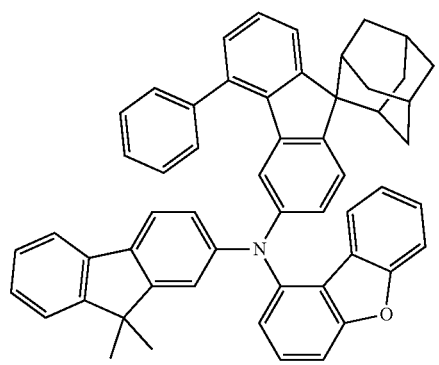
72
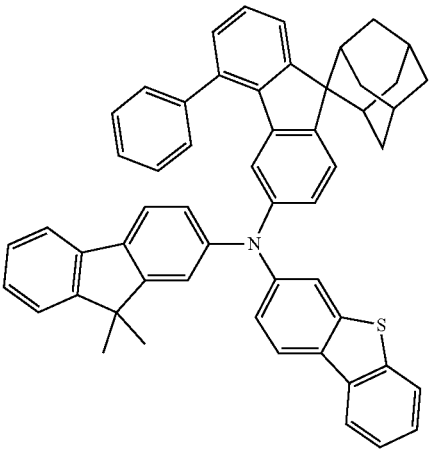
73
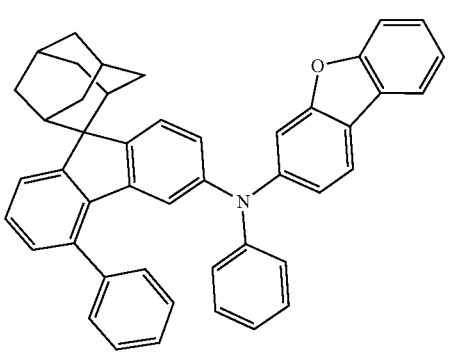
74
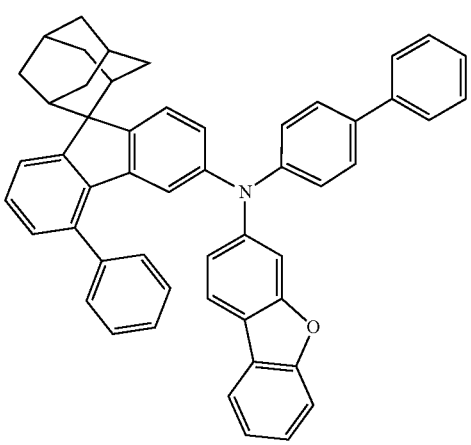
75
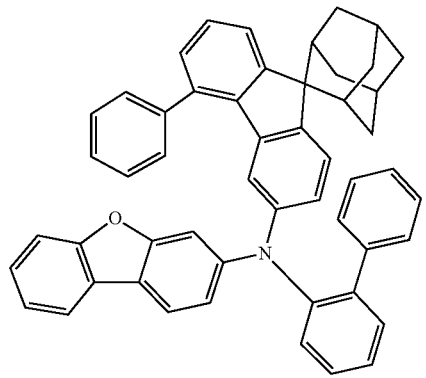

76
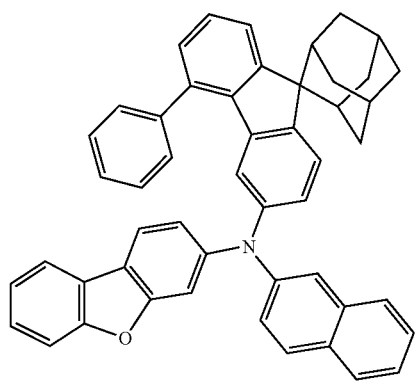
77
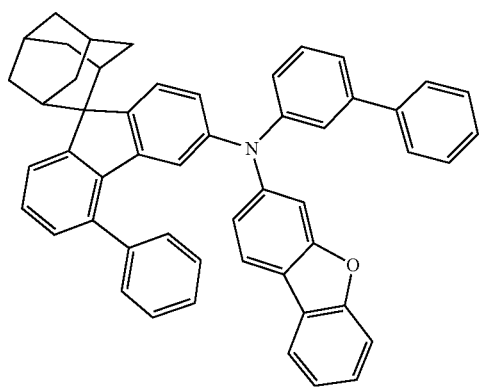
78
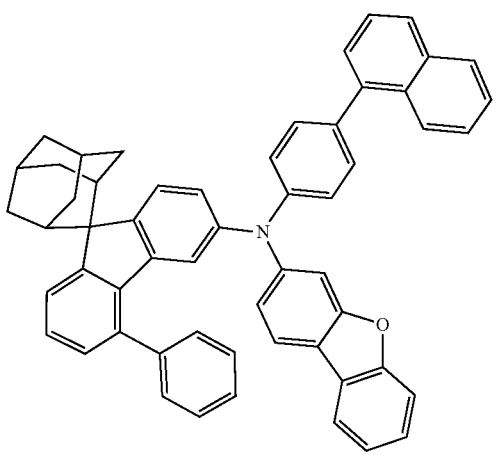
79
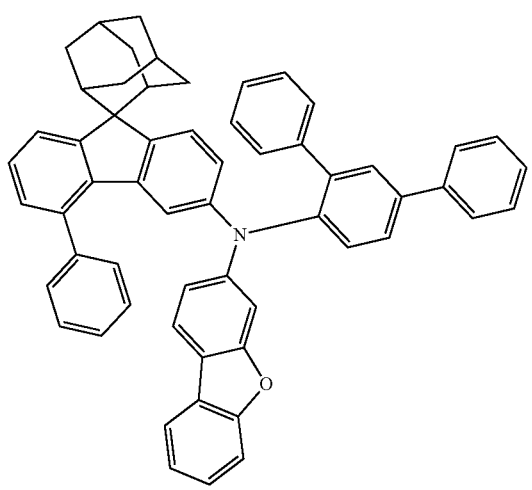
80
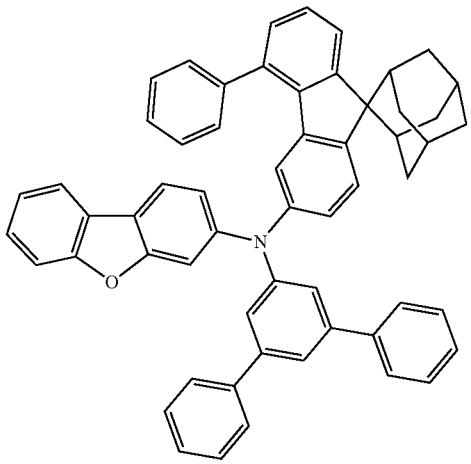
81
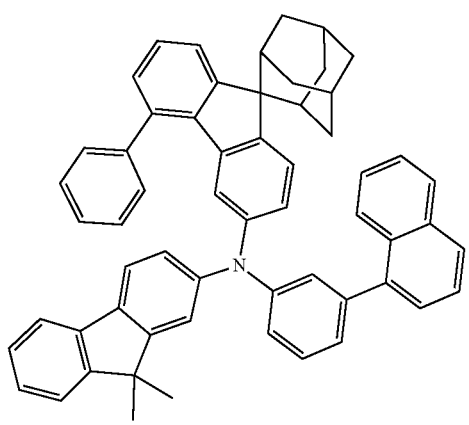

82
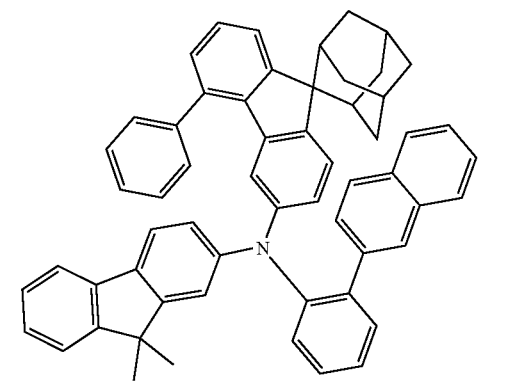
83
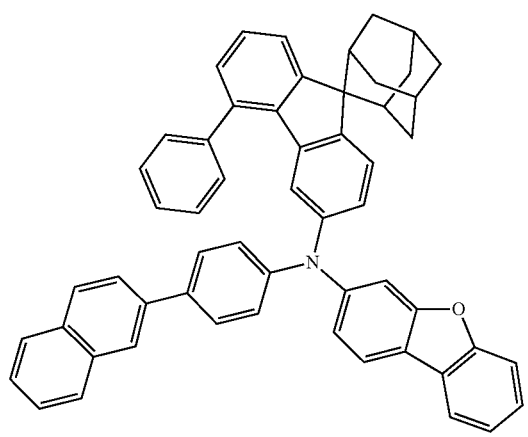
84
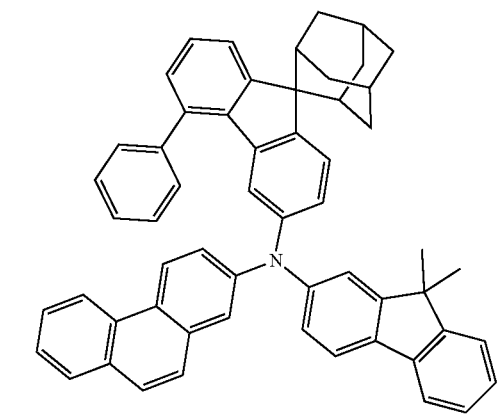
85
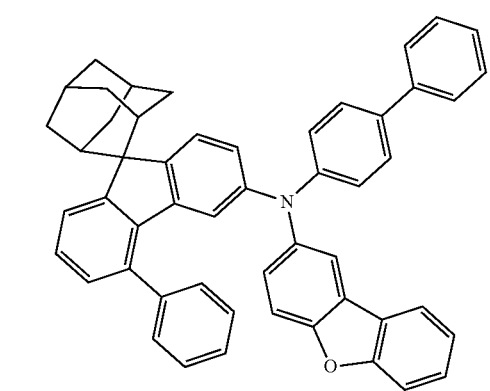
86
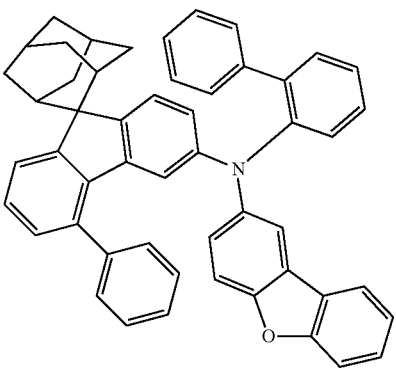
87
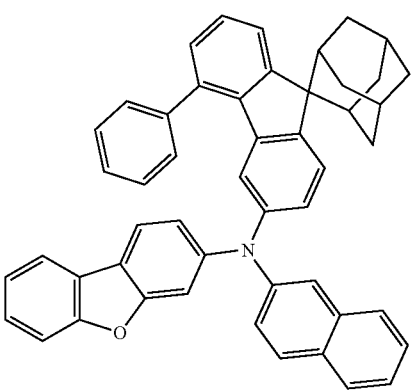
88
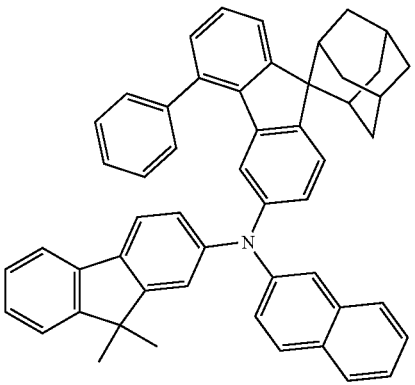
89
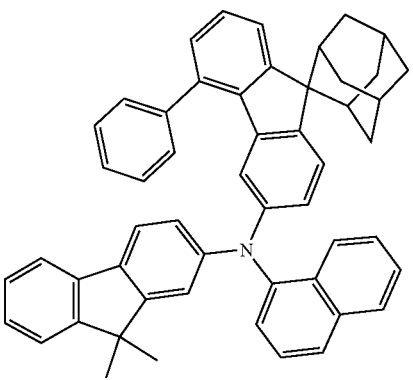

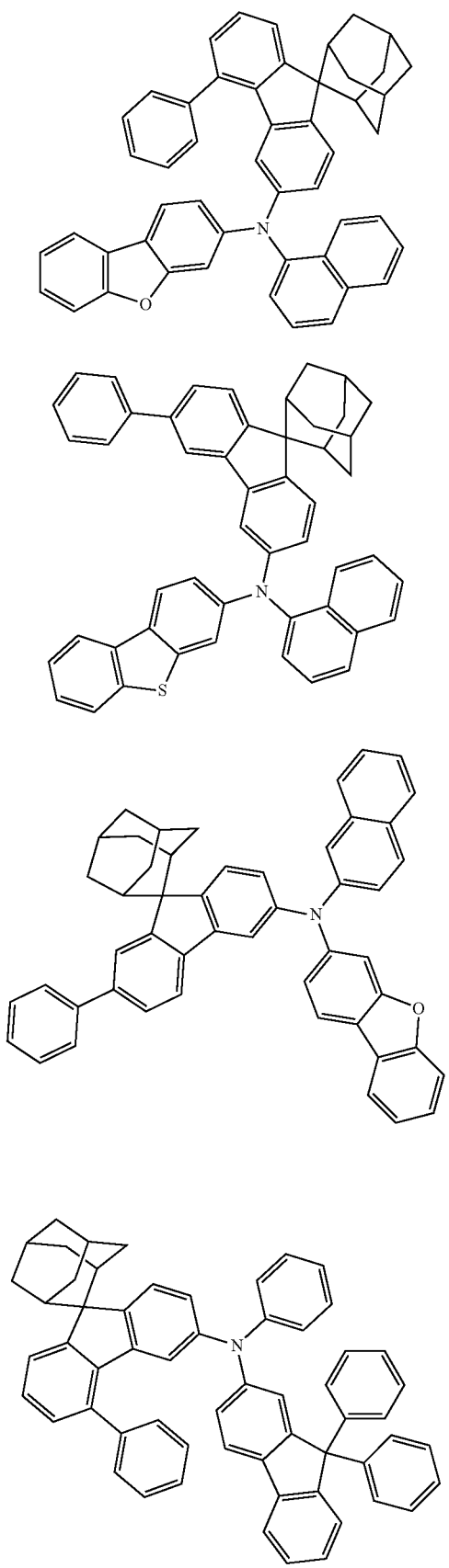
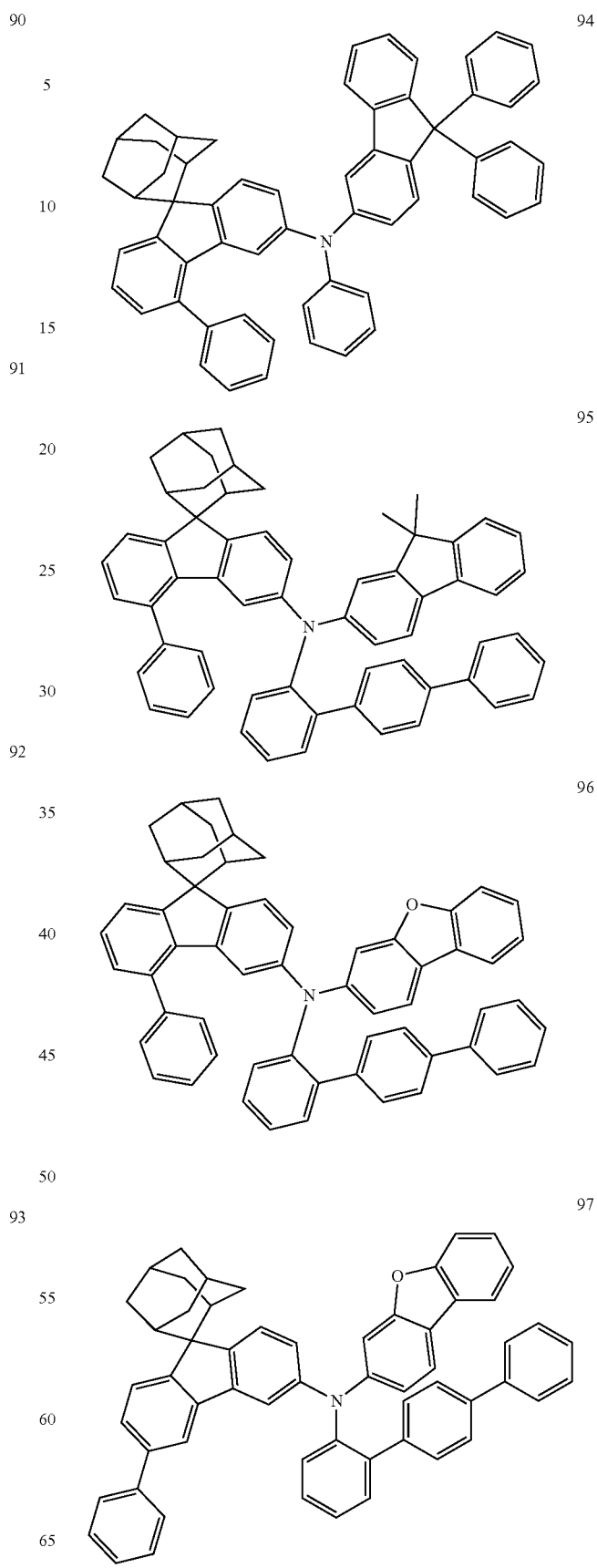

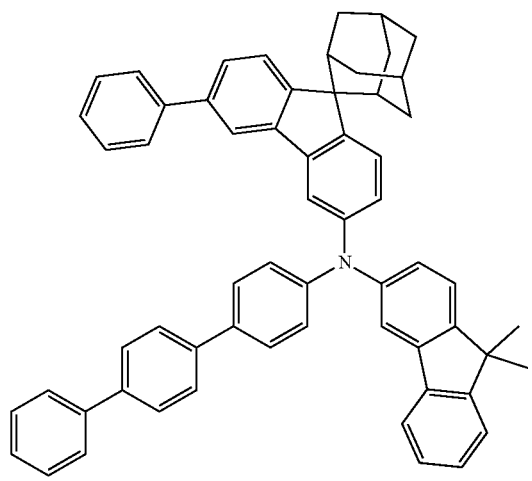
98
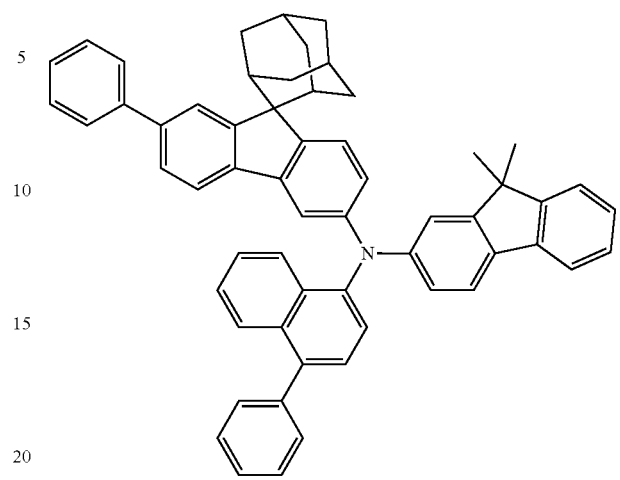
101
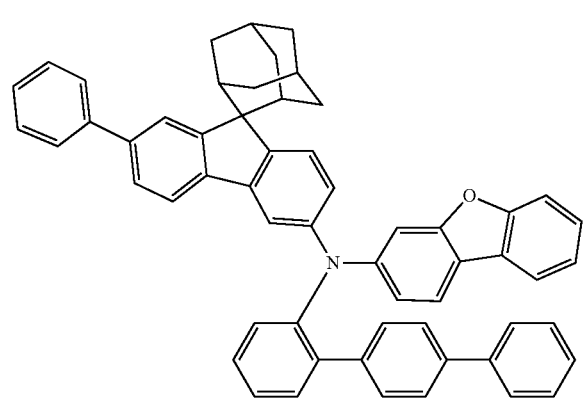
99
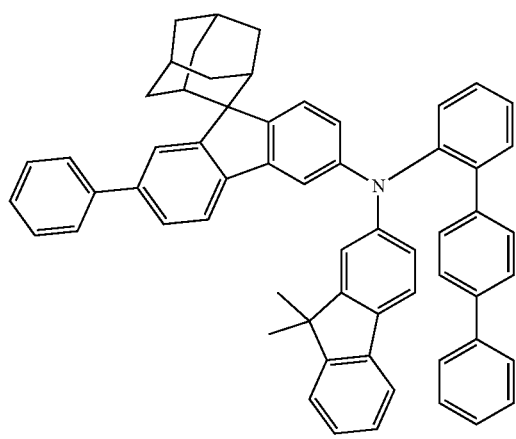
100
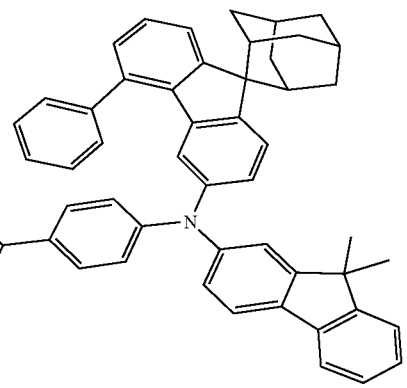
102
103

-continued
104
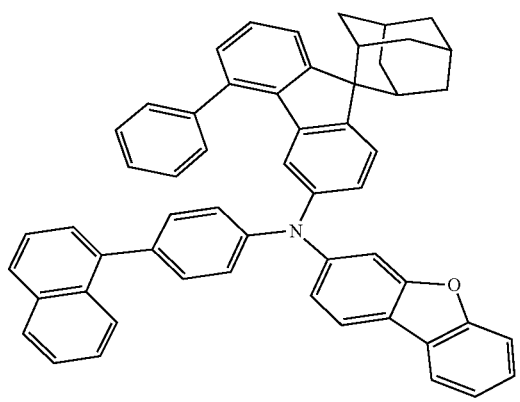
105
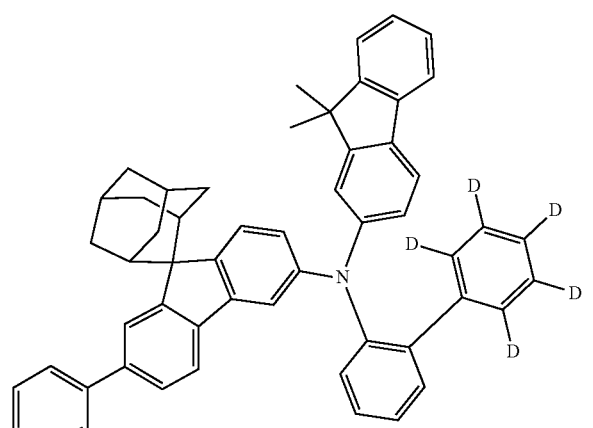
106
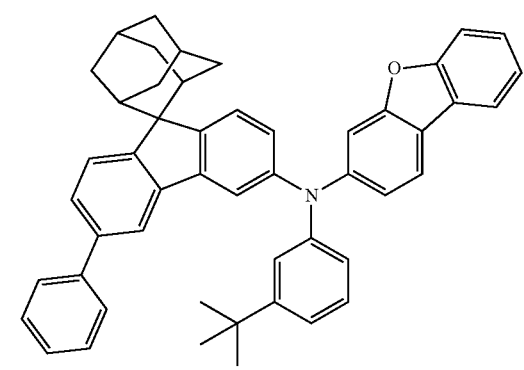
-continued
107
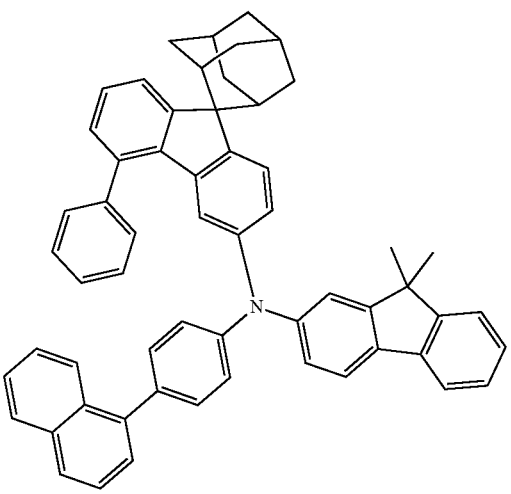
108
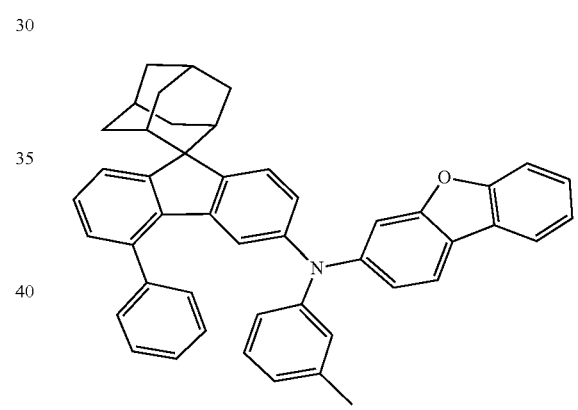
109
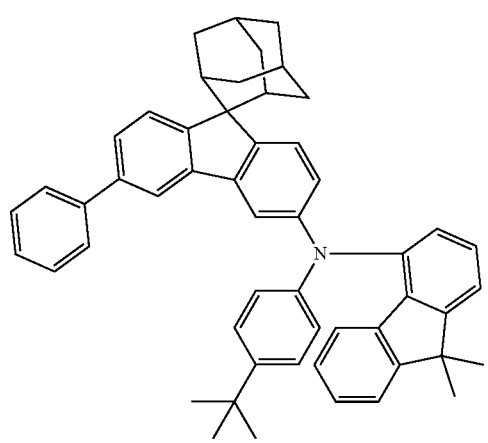

-continued

110
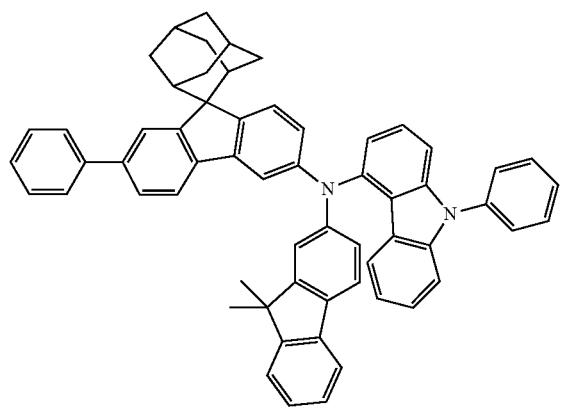

111
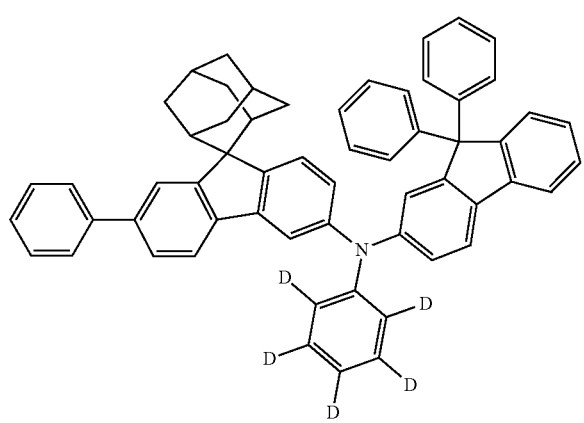

-continued

112
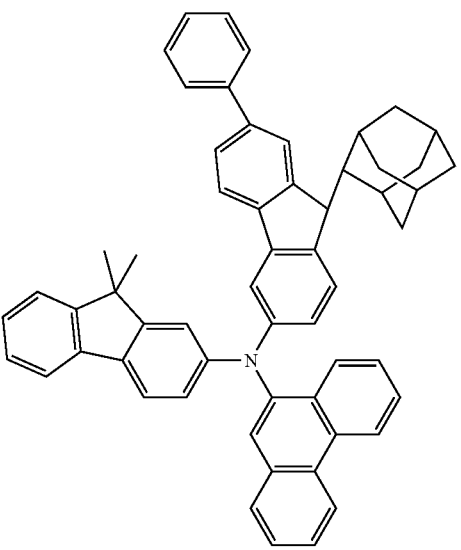

117

4. An electronic component, comprising an anode and a cathode that are disposed oppositely, and a functional layer disposed between the anode and the cathode, wherein the functional layer comprises the organic compound of claim 1; the functional layer comprises a hole transport layer, and the hole transport layer comprises the organic compound of claim 1.

5. The electronic component of claim 4, wherein the electronic component is an organic electroluminescent device or a photoelectric conversion device.

6. An electronic apparatus, comprising the electronic component of claim 4.

7. The electronic component of claim 4, wherein the electronic component is an organic electroluminescent device, and the hole transport layer comprises a first hole transport layer and a second hole transport layer that are stacked in layers, wherein the first hole transport layer is closer to the anode than the second hole transport layer, and the second hole transport layer comprises the organic compound.

* * * * *